United States Patent
Walker et al.

(10) Patent No.: US 11,026,481 B2
(45) Date of Patent: *Jun. 8, 2021

(54) FOOT PRESENCE SIGNAL PROCESSING USING VELOCITY

(71) Applicant: NIKE, Inc., Beaverton, OR (US)

(72) Inventors: Steven H. Walker, Camas, WA (US); Phillip Meneau, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/311,813

(22) PCT Filed: Mar. 14, 2018

(86) PCT No.: PCT/US2018/022466
§ 371 (c)(1),
(2) Date: Dec. 20, 2018

(87) PCT Pub. No.: WO2018/170148
PCT Pub. Date: Sep. 20, 2018

(65) Prior Publication Data
US 2019/0387840 A1    Dec. 26, 2019

Related U.S. Application Data

(63) Continuation-in-part of application No. 15/610,179, filed on May 31, 2017, now Pat. No. 10,448,707.
(Continued)

(30) Foreign Application Priority Data

Mar. 15, 2017    (TW) .................................. 106108511

(51) Int. Cl.
*A43C 11/16* (2006.01)
*A61B 5/00* (2006.01)
(Continued)

(52) U.S. Cl.
CPC .......... *A43C 11/165* (2013.01); *A43B 1/0054* (2013.01); *A43B 3/001* (2013.01);
(Continued)

(58) Field of Classification Search
None
See application file for complete search history.

(56) References Cited

U.S. PATENT DOCUMENTS

| 4,152,748 A | 5/1979 | Arkans |
| 4,922,634 A | 5/1990 | Seidel |

(Continued)

FOREIGN PATENT DOCUMENTS

| CN | 1813603 | | 8/2006 | |
| CN | 101217894 | * | 7/2008 | ........... A61B 5/1038 |

(Continued)

OTHER PUBLICATIONS

Clara Sanz Morère (MEMS Technology Sensors as a More Advantageous Technique for Measuring Foot Plantar Pressure and Balance in Humans, Jan. 2016, 9 pages) (Year: 2016).*

(Continued)

*Primary Examiner* — Tung S Lau
(74) *Attorney, Agent, or Firm* — Schwegman Lundberg & Woessner, P.A.

(57) ABSTRACT

A foot presence sensor system for an active article of footwear can include a sensor housing configured to be disposed at or in an insole of the article, and a controller circuit, disposed within the sensor housing, configured to trigger one or more automated functions of the footwear based on a foot presence indication. In an example, the sensor system includes a capacitive sensor, and the sensor is configured to sense changes in a foot proximity to the sensor in footwear. Information about the sensed proximity can be used to determine a foot velocity characteristic, which in
(Continued)

turn can be used to update an automated footwear function, such as an automatic lacing function, or can be used to determine a step count, foot strike force, a rate of travel, or other information about a foot, about an activity, or about the footwear.

15 Claims, 30 Drawing Sheets

Related U.S. Application Data which is a continuation of application No. 15/458,625, filed on Mar. 14, 2017, now Pat. No. 10,499,711, application No. 16/311,813, which is a continuation-in-part of application No. PCT/US2017/022342, filed on Mar. 14, 2017, which is a continuation-in-part of application No. 15/460,060, filed on Mar. 15, 2017, and a continuation-in-part of application No. PCT/US2017/022576, filed on Mar. 15, 2017, and a continuation-in-part of application No. 15/459,889, filed on Mar. 15, 2017, now Pat. No. 10,172,423, and a continuation-in-part of application No. PCT/US2017/022533, filed on Mar. 15, 2017, and a continuation-in-part of application No. 15/459,897, filed on Mar. 15, 2017, and a continuation-in-part of application No. PCT/US2017/022548, filed on Mar. 15, 2017, and a continuation-in-part of application No. 15/459,402, filed on Mar. 15, 2017, and a continuation-in-part of application No. PCT/US2017/022489, filed on Mar. 15, 2017.

(60) Provisional application No. 62/556,103, filed on Sep. 8, 2017.

(51) Int. Cl.

| | | |
|---|---|---|
| *G01L 5/12* | (2006.01) | |
| *G01L 1/14* | (2006.01) | |
| *A43B 1/00* | (2006.01) | |
| *A43B 3/00* | (2006.01) | |
| *A43B 13/14* | (2006.01) | |
| *A43B 17/00* | (2006.01) | |
| *A43C 1/00* | (2006.01) | |
| *G01L 5/24* | (2006.01) | |
| *G05B 15/02* | (2006.01) | |
| *A43C 7/00* | (2006.01) | |
| *G01L 1/12* | (2006.01) | |
| *G05B 19/048* | (2006.01) | |
| *A43C 11/00* | (2006.01) | |
| *G01D 5/14* | (2006.01) | |
| *G01D 5/24* | (2006.01) | |
| *G01D 5/34* | (2006.01) | |

(52) U.S. Cl.
CPC .......... *A43B 3/0005* (2013.01); *A43B 3/0031* (2013.01); *A43B 13/14* (2013.01); *A43B 17/00* (2013.01); *A43C 1/00* (2013.01); *A43C 7/00* (2013.01); *A43C 11/008* (2013.01); *A61B 5/6807* (2013.01); *G01L 1/12* (2013.01); *G01L 1/144* (2013.01); *G01L 5/12* (2013.01); *G01L 5/24* (2013.01); *G05B 15/02* (2013.01); *G05B 19/048* (2013.01); *G01D 5/145* (2013.01); *G01D 5/2405* (2013.01); *G01D 5/34* (2013.01); *G05B 2219/24015* (2013.01)

(56) References Cited

U.S. PATENT DOCUMENTS

| | | |
|---|---|---|
| 5,343,190 A | 8/1994 | Rodgers |
| 5,662,123 A | 9/1997 | Goldman |
| 5,791,068 A | 8/1998 | Bernier et al. |
| 5,929,332 A | 7/1999 | Brown |
| 6,032,387 A | 3/2000 | Johnson |
| 6,033,370 A | 3/2000 | Reinbold et al. |
| 6,195,921 B1 | 3/2001 | Truong |
| 6,199,303 B1 | 3/2001 | Luthi et al. |
| 6,301,964 B1 | 10/2001 | Fyfe et al. |
| 6,305,221 B1 | 10/2001 | Hutchings |
| 6,427,361 B1 | 8/2002 | Chou |
| 6,513,381 B2 | 2/2003 | Fyfe et al. |
| 6,643,954 B2 | 11/2003 | Voswinkel |
| 6,691,433 B2 | 2/2004 | Liu |
| 6,896,128 B1 | 5/2005 | Johnson |
| 6,898,299 B1 | 5/2005 | Brooks |
| 7,032,448 B2 | 4/2006 | Hamamoto |
| 7,310,895 B2 | 12/2007 | Whittlesey et al. |
| 7,331,126 B2 | 2/2008 | Johnson |
| 7,355,519 B2 | 4/2008 | Grold et al. |
| 7,487,606 B2 | 2/2009 | Koo et al. |
| 7,506,460 B2 | 3/2009 | Dibenedetto et al. |
| 7,552,549 B2 | 6/2009 | Whittlesey et al. |
| 7,614,166 B2 | 11/2009 | Vick et al. |
| 7,676,957 B2 | 3/2010 | Johnson |
| 7,712,373 B2 | 5/2010 | Nagle et al. |
| 7,752,774 B2 | 7/2010 | Ussher |
| 7,793,430 B2 | 9/2010 | Ellis |
| 7,827,000 B2 | 11/2010 | Stirling et al. |
| 7,911,339 B2 | 3/2011 | Vock et al. |
| 7,912,672 B2 | 3/2011 | Feichtinger et al. |
| 8,028,443 B2 | 10/2011 | Case, Jr. |
| 8,046,937 B2 | 11/2011 | Beers et al. |
| 8,480,541 B1 | 7/2013 | Brunts |
| 8,522,456 B2 | 9/2013 | Beers et al. |
| 8,581,731 B2 | 11/2013 | Purks et al. |
| 8,676,541 B2 | 3/2014 | Schrock et al. |
| 8,739,639 B2 | 6/2014 | Owings et al. |
| 8,752,200 B2 | 6/2014 | Varshavsky et al. |
| 8,769,844 B2 | 7/2014 | Beers et al. |
| 8,904,673 B2 | 12/2014 | Johnson et al. |
| 8,935,860 B2 | 1/2015 | Torres |
| 9,063,182 B2 | 6/2015 | Lombardi et al. |
| 9,095,251 B2 | 8/2015 | Purks et al. |
| 9,322,121 B2 | 4/2016 | Dunne et al. |
| 9,591,891 B1 | 3/2017 | Baucom et al. |
| 9,907,359 B2 | 3/2018 | Beers et al. |
| 10,172,423 B2 | 1/2019 | Walker et al. |
| 10,448,707 B2* | 10/2019 | Walker .................. A43B 3/001 |
| 10,477,923 B2 | 11/2019 | Walker et al. |
| 10,499,711 B2 | 12/2019 | Walker et al. |
| 10,722,000 B2 | 7/2020 | Walker et al. |
| 10,758,012 B2 | 9/2020 | Walker et al. |
| 2004/0182153 A1 | 9/2004 | Hamamoto |
| 2005/0183292 A1 | 8/2005 | Dibenedetto et al. |
| 2005/0198867 A1 | 9/2005 | Labbe |
| 2006/0230642 A1 | 10/2006 | Vick et al. |
| 2007/0000154 A1 | 1/2007 | Dibenedetto et al. |
| 2007/0006489 A1 | 1/2007 | Case et al. |
| 2007/0011919 A1 | 1/2007 | Case, Jr. |
| 2007/0180736 A1 | 8/2007 | Dibenedetto et al. |
| 2007/0209234 A1 | 9/2007 | Chou |
| 2007/0240334 A1 | 10/2007 | Johnson |
| 2008/0060224 A1 | 3/2008 | Whittlesey et al. |
| 2008/0086911 A1 | 4/2008 | Labbe |
| 2009/0071805 A1 | 3/2009 | Horning et al. |
| 2009/0102669 A1 | 4/2009 | Lin |
| 2009/0113762 A1 | 5/2009 | Leimer et al. |
| 2009/0272007 A1* | 11/2009 | Beers .................... A43C 11/14 36/50.1 |
| 2010/0004566 A1 | 1/2010 | Son et al. |
| 2010/0063778 A1* | 3/2010 | Schrock ............ A61B 5/6807 702/188 |
| 2010/0184563 A1* | 7/2010 | Molyneux ............ A43B 1/0054 482/1 |

(56) References Cited

U.S. PATENT DOCUMENTS

| | | |
|---|---|---|
| 2010/0199524 A1 | 8/2010 | Grun et al. |
| 2010/0201650 A1 | 8/2010 | Son |
| 2010/0253645 A1 | 10/2010 | Bolender |
| 2011/0050251 A1 | 3/2011 | Franke et al. |
| 2011/0054359 A1 | 3/2011 | Sazonov et al. |
| 2011/0276112 A1 | 11/2011 | Simon et al. |
| 2011/0304497 A1* | 12/2011 | Molyneux ............ H01Q 1/273 342/42 |
| 2012/0041767 A1 | 2/2012 | Hoffman et al. |
| 2012/0062248 A1 | 3/2012 | Lee et al. |
| 2012/0068760 A1 | 3/2012 | Caldwell et al. |
| 2012/0217982 A1 | 8/2012 | Narayanasamy et al. |
| 2012/0247919 A1 | 10/2012 | Soldner et al. |
| 2012/0291563 A1 | 11/2012 | Schrock et al. |
| 2012/0291564 A1 | 11/2012 | Amos et al. |
| 2012/0304500 A1 | 12/2012 | Bove |
| 2013/0019503 A1 | 1/2013 | Vogt |
| 2013/0086997 A1 | 4/2013 | Tanhua et al. |
| 2013/0147752 A1 | 6/2013 | Simmons et al. |
| 2013/0185961 A1 | 7/2013 | Tseng et al. |
| 2013/0190903 A1 | 7/2013 | Balakrishnan et al. |
| 2013/0213144 A1 | 8/2013 | Rice et al. |
| 2013/0293244 A1 | 11/2013 | Leek |
| 2014/0062703 A1 | 3/2014 | Purks et al. |
| 2014/0135954 A1 | 5/2014 | Vranish |
| 2014/0165427 A1 | 6/2014 | Molyneux et al. |
| 2014/0213843 A1 | 7/2014 | Pilla et al. |
| 2014/0221726 A1 | 8/2014 | Pilla et al. |
| 2014/0260689 A1 | 9/2014 | Walker |
| 2014/0360047 A1 | 12/2014 | Beers et al. |
| 2015/0018721 A1 | 1/2015 | Wang et al. |
| 2015/0100245 A1 | 4/2015 | Huang et al. |
| 2015/0237183 A1 | 8/2015 | Novet |
| 2015/0257679 A1 | 9/2015 | Ross |
| 2015/0272264 A1 | 10/2015 | Lee |
| 2015/0276963 A1 | 10/2015 | Casimiro et al. |
| 2015/0289594 A1 | 10/2015 | Rushbrook et al. |
| 2015/0290496 A1 | 10/2015 | Purks et al. |
| 2015/0296922 A1 | 10/2015 | Rushbrook et al. |
| 2015/0309563 A1 | 10/2015 | Connor |
| 2015/0359457 A1 | 12/2015 | Blumenthal et al. |
| 2016/0074547 A1 | 3/2016 | Dobrinsky et al. |
| 2016/0084487 A1 | 3/2016 | Chacon et al. |
| 2016/0106177 A1 | 4/2016 | De Laurentis |
| 2016/0124573 A1 | 5/2016 | Rouaissia et al. |
| 2017/0002254 A1 | 1/2017 | Haque et al. |
| 2017/0049190 A1 | 2/2017 | Maussen |
| 2017/0176266 A1 | 6/2017 | Mathieu et al. |
| 2017/0265582 A1* | 9/2017 | Walker ...................... G01L 5/24 |
| 2017/0265583 A1 | 9/2017 | Schneider et al. |
| 2017/0265584 A1 | 9/2017 | Walker et al. |
| 2017/0265587 A1 | 9/2017 | Walker et al. |
| 2017/0265588 A1 | 9/2017 | Walker et al. |
| 2017/0265589 A1 | 9/2017 | Walker et al. |
| 2017/0265594 A1 | 9/2017 | Walker et al. |
| 2017/0273849 A1 | 9/2017 | Oleson et al. |
| 2018/0199674 A1* | 7/2018 | Walker ...................... G01D 5/24 |
| 2018/0256071 A1 | 9/2018 | Mathieu et al. |
| 2018/0289110 A1 | 10/2018 | Bock et al. |
| 2018/0368526 A1 | 12/2018 | Bock et al. |
| 2019/0166954 A1 | 6/2019 | Walker et al. |
| 2019/0174871 A1 | 6/2019 | Walker et al. |
| 2019/0208865 A1 | 7/2019 | Walker et al. |
| 2019/0373986 A1 | 12/2019 | Walker et al. |
| 2019/0387840 A1* | 12/2019 | Walker ................ A43B 3/0005 |
| 2020/0046081 A1 | 2/2020 | Walker et al. |
| 2020/0077749 A1 | 3/2020 | Walker et al. |
| 2020/0352284 A1 | 11/2020 | Walker et al. |

FOREIGN PATENT DOCUMENTS

| | | | | |
|---|---|---|---|---|
| CN | 101217894 A | 7/2008 | | |
| CN | 101951798 A | 1/2011 | | |
| CN | 102014682 A | 4/2011 | | |
| CN | 102308270 | * 1/2012 | ............ | G06F 3/0447 |
| CN | 102308270 A | 1/2012 | | |
| CN | 102972100 | 3/2013 | | |
| CN | 103476283 | 12/2013 | | |
| CN | 103476284 A | 12/2013 | | |
| CN | 103608752 | 2/2014 | | |
| CN | 203505737 U | 4/2014 | | |
| CN | 104582519 A | 4/2015 | | |
| CN | 104619207 | * 5/2015 | ............. | A41D 1/002 |
| CN | 104619207 A | 5/2015 | | |
| CN | 205568006 | 9/2016 | | |
| CN | 106455747 A | 2/2017 | | |
| CN | 109152445 A | 1/2019 | | |
| CN | 109152446 A | 1/2019 | | |
| CN | 109152447 A | 1/2019 | | |
| CN | 109152448 | * 1/2019 | ............. | A43C 11/16 |
| CN | 109152448 A | 1/2019 | | |
| CN | 109414092 A | 3/2019 | | |
| CN | 110621186 | * 12/2019 | ............ | G05B 19/048 |
| CN | 110621186 A | 12/2019 | | |
| CN | 109152445 B | 10/2020 | | |
| CN | 112471685 | 3/2021 | | |
| DE | 3900777 A1 | 7/1990 | | |
| EP | 1447653 A1 | 8/2004 | | |
| EP | 1457128 A2 | 9/2004 | | |
| EP | 3429416 A1 | 1/2019 | | |
| JP | 2004267784 A | 9/2004 | | |
| JP | 2005279281 A | 10/2005 | | |
| JP | 2006349478 | 12/2006 | | |
| JP | 2008229372 A | 10/2008 | | |
| JP | 2008546500 | 12/2008 | | |
| JP | 2009500141 A | 1/2009 | | |
| JP | 201450760 U | 5/2010 | | |
| JP | 2011509710 | 3/2011 | | |
| JP | 2011519611 A | 7/2011 | | |
| JP | 2015057598 | 3/2015 | | |
| JP | 2019508168 A | 3/2019 | | |
| JP | 2019508178 A | 3/2019 | | |
| JP | 2019512322 | 5/2019 | | |
| JP | 2019512323 | 5/2019 | | |
| JP | 2019512325 | 5/2019 | | |
| JP | 2020509875 A | 4/2020 | | |
| JP | 2020203115 A | 12/2020 | | |
| KR | 20190131515 A | 11/2019 | | |
| KR | 20200075904 A | 6/2020 | | |
| KR | 102141214 B1 | 8/2020 | | |
| TW | 521593 U | 2/2003 | | |
| TW | 201739371 A | 11/2017 | | |
| TW | 201902382 A | 1/2019 | | |
| WO | WO-2007008352 A1 | 1/2007 | | |
| WO | WO-2009071652 A1 | 6/2009 | | |
| WO | WO-2014100045 A1 | 6/2014 | | |
| WO | WO-2014188350 A1 | 11/2014 | | |
| WO | WO-2015163982 A1 | 10/2015 | | |
| WO | WO-2017160865 A1 | 9/2017 | | |
| WO | WO-2017160969 A1 | 9/2017 | | |
| WO | WO-2017161000 A2 | 9/2017 | | |
| WO | WO-2017161014 A1 | 9/2017 | | |
| WO | WO-2017161037 A1 | 9/2017 | | |
| WO | WO 2018/170148 | * 5/2018 | | |
| WO | WO-2017161000 A3 | 8/2018 | | |
| WO | WO 2018170148 | * 9/2018 | ............... | A43B 3/00 |
| WO | WO-2018170148 A2 | 9/2018 | | |
| WO | WO-2020186171 A1 | 9/2020 | | |

OTHER PUBLICATIONS

"U.S. Appl. No. 15/458,625, Examiner Interview Summary dated Mar. 27, 2019", 3 pgs.

"U.S. Appl. No. 15/458,625, Final Office Action dated Feb. 8, 2019", 16 pgs.

"U.S. Appl. No. 15/460,060, Non Final Office Action dated Apr. 18, 2019", 32 pgs.

"U.S. Appl. No. 15/460,060, Response filed Feb. 1, 2019 to Restriction Requirement dated Dec. 3, 2018", 8 pgs.

"U.S. Appl. No. 16/197,905, Preliminary Amendment dated Feb. 19, 2019", 6 pgs.

(56) References Cited

OTHER PUBLICATIONS

"U.S. Appl. No. 16/280,732, Non Final Office Action dated Mar. 27, 2019", 7 pgs.
"European Application Serial No. 17767420.7, Response Filed Feb. 1, 2019 to Communication pursuant to Rules 161(2) and 162 EPC dated Nov. 2, 2019", 13 pgs.
"U.S. Appl. No. 15/458,625, Non Final Office Action dated Jul. 27, 2018", 15 pgs.
"U.S. Appl. No. 15/458,625, Response filed Oct. 26, 2018 to Non Final Office Action dated Jul. 27, 2018", 11 pgs.
"U.S. Appl. No. 15/458,625, Response Filed May 29, 2018 to Restriction Requirement dated Apr. 5, 2018", 8 pgs.
"U.S. Appl. No. 15/458,625, Restriction Requirement dated Apr. 5, 2018", 5 pgs.
"U.S. Appl. No. 15/459,889, Examiner Interview Summary dated Oct. 9, 2018", 3 pgs.
"U.S. Appl. No. 15/459,889, Non Final Office Action dated Jun. 26, 2018", 12 pgs.
"U.S. Appl. No. 15/459,889, Notice of Allowance dated Nov. 15, 2018", 5 pgs.
"U.S. Appl. No. 15/459,889, Response filed Oct. 9, 2018 to Non Final Office Action dated Jun. 26, 2018", 17 pgs.
"U.S. Appl. No. 15/459,897, Response filed Nov. 9, 2018 to Restriction Requirement dated Sep. 10, 2018", 8 pgs.
"U.S. Appl. No. 15/459,897, Restriction Requirement dated Sep. 10, 2018", 6 pgs.
"U.S. Appl. No. 15/460,060, Restriction Requirement dated Dec. 3, 2018", 7 pgs.
"U.S. Appl. No. 15/610,179, Advisory Action dated Oct. 12, 2018", 3 pgs.
"U.S. Appl. No. 15/610,179, Final Office Action dated Aug. 6, 2018", 32 pgs.
"U.S. Appl. No. 15/610,179, Non Final Office Action dated Feb. 15, 2018", 38 pgs.
"U.S. Appl. No. 15/610,179, Response filed Oct. 4, 2018 to Final Office Action dated Aug. 6, 2018", 15 pgs.
"U.S. Appl. No. 15/610,179, Response filed Nov. 9, 2017 to Restriction Requirement dated Sep. 11, 2017", 9 pgs.
"Application U.S. Appl. No. 15/610,179, Response filed May 15, 2018 to Non Final Office Action dated Feb. 15, 2018", 19 pgs.
"U.S. Appl. No. 15/610,179, Restriction Requirement dated Sep. 11, 2017", 10 pgs.
"Chinese Application Serial No. 201780028316.3, Office Action dated Nov. 21, 2018", W/O English Translation, 1 pg.
"International Application Serial No. PCT/US2017/022342, International Preliminary Report on Patentability dated Jul. 3, 2018", 8 pgs.
"International Application Serial No. PCT/US2017/022342, International Search Report dated Jun. 20, 2017", 4 pgs.
"International Application Serial No. PCT/US2017/022342, Written Opinion dated Jun. 20, 2017", 9 pgs.
"International Application Serial No. PCT/US2017/022489, International Preliminary Report on Patentability dated Sep. 27, 2018", 10 pgs.
"International Application Serial No. PCT/U52017/022489, International Search Report dated Jun. 20, 2017", 4 pgs.
"International Application Serial No. PCT/US2017/022489, Written Opinion dated Jun. 20, 2017", 8 pgs.
"International Application Serial No. PCT/US2017/022533, International Preliminary Report on Patentability dated Jul. 3, 2018", 7 pgs.
"International Application Serial No. PCT/US2017/022533, International Search Report dated Jun. 26, 2017", 4 pgs.
"International Application Serial No. PCT/US2017/022533, Written Opinion dated Jun. 26, 2017", 9 pgs.
"International Application Serial No. PCT/US2017/022548, International Preliminary Report on Patentability dated Sep. 27, 2018", 11 pgs.
"International Application Serial No. PCT/US2017/022548, International Search Report dated Jun. 28, 2017", 3 pgs.
"International Application Serial No. PCT/US2017/022548, Written Opinion dated Jun. 28, 2017", 9 pgs.
"International Application Serial No. PCT/US2017/022576, International Preliminary Report on Patentability dated Sep. 27, 2017", 9 pgs.
"International Application Serial No. PCT/US2017/022576, International Search Report dated Jun. 28, 2017", 3 pgs.
"International Application Serial No. PCT/US2017/022576, Written Opinion dated Jun. 28, 2017", 7 pgs.
"International Application Serial No. PCT/US2018/022466, International Search Report dated Oct. 16, 2018", 6 pgs.
"International Application Serial No. PCT/US2018/022466, Written Opinion dated Oct. 16, 2018", 6 pgs.
"Taiwanese Application Serial No. 106108511, Decision of Rejection dated Jul. 20, 2018", W/ English Translation, 5 pgs.
"Taiwanese Application Serial No. 106108511, Office Action dated Dec. 5, 2017", w/ English translation, 16 pgs.
"Taiwanese Application Serial No. 106108511, Request for Reexamination filed Sep. 21, 2018 to Decision of Rejection dated Jul. 20, 2018", w/ English claims, Claims not amended in Reexamination brief, current claims included in attachment, 236 pgs.
"Taiwanese Application Serial No. 106108511, Response filed Mar. 5, 2018 to Office Action dated Dec. 5, 2017", w/ claims in English, 110 pgs.
"U.S. Appl. No. 15/458,625, Respnse filed May 8, 2019 to Final Office Action dated Feb. 8, 2019", 13 pgs.
"European Application Serial No. 17767355.5, Response filed Apr. 24, 2019 to Communication Pursuant to Rules 161 and 162 dated Oct. 30, 2018", 10 pgs.
"European Application Serial No. 17767469.4, Response filed Apr. 24, 2019 to Communication Pursuant to Rules 161 and 162 dated Nov. 5, 2018", 12 pgs.
"U.S. Appl. No. 15/610,179, Notice of Allowance dated May 15, 2019", 12 pgs.
"European Application Serial No. 17767442.1, Response filed Apr. 26, 2019 to Communication Pursuant to Rules 161 and 162 dated Oct. 24, 2018", 11 pgs.
"European Application Serial No. 17767453.8, Response filed Apr. 26, 2019 to Communication Pursuant to Rules 161 and 162 dated Oct. 24, 2018", 13 pgs.
"U.S. Appl. No. 16/280,732, Examiner Interview Summary dated Jun. 7, 2019", 3 pgs.
"U.S. Appl. No. 15/458,625, Response filed Jun. 21, 2019 to Final Office Action dated Feb. 8, 2019", 14 pgs.
"U.S. Appl. No. 15/458,625, Advisory Action dated Jun. 26, 2019", 4 pgs.
"U.S. Appl. No. 16/280,732, Response Filed Jun. 26, 2019 to Non Final Office Action dated Mar. 27, 2019", 11 pgs.
"Chinese Application Serial No. 201780029822.4, Voluntary Amendment dated Jul. 4, 2019", w English claims, 11 pgs.
"U.S. Appl. No. 16/280,732, Notice of Allowance dated Jul. 17, 2019", 5 pgs.
"U.S. Appl. No. 15 458,625, Notice of Allowance dated Aug. 7, 2019", 12 pgs.
"Chinese Application Serial No. 201780029824.3, Voluntary Amendment mailed Jul. 4, 2019", w English claims, 15 pgs.
"U.S. Appl. No. 15/610,179, 312 Amendment dated Aug. 15, 2019", 6 pgs.
Bamberg, Stacy J, "Development of a Quantitative In-Show Measurement System for Assessing Balance: Sixteen-Sensor Insoles", (2006).
Kothari, M, "Capacitive Sensors for Measuring the Pressure between the Foot and Shoe", IEEE, (1988).
Morris, Stacy J, "A Shoe-Integrated Sensor System for Wireless Gait Analysis and Real-Time Therapeutic Feedback, dissertation", Massachusetts Institute of Technology, MA, (2004), 1-314.
Sumiya, Tadashi, "Sensing Stability and Dynamic Response of the F-Scan in-Shoe Sensing System: A Technical Note", (1988).
Takahashi, Youhei, "Six-axis Force Sensing Footwear for National Walking Analysis", (2004).
Zhou, Chenming, "A Shoe-Embedded RF Sensor for Motion Detection", IEEE, (2011).

(56) References Cited

OTHER PUBLICATIONS

"International Application Serial No. PCT US2018 022466, International Preliminary Report on Patentability dated Sep. 26, 2019", 8 pgs.
"U.S. Appl. No. 15/459,402, Restriction Requirement dated Sep. 30, 2019", 7 pgs.
"U.S. Appl. No. 15/459,897, Non Final Office Action dated Oct. 3, 2019", 46 pgs.
"U.S. Appl. No. 15/459,402, Non Final Office Action dated Apr. 15, 2020", 12 pgs.
"U.S. Appl. No. 15/459,402, Response filed Dec. 30, 2019 to Restriction Requirement dated Sep. 30, 2019", 8 pgs.
"U.S. Appl. No. 15/459,897, Examiner Interview Summary dated Nov. 6, 2019", 3 pgs.
"U.S. Appl. No. 15/459,897, Final Office Action dated Apr. 14, 2020", 49 pgs.
"U.S. Appl. No. 15/459,897, Response filed Jan. 3, 2020 to Non Final Office Action dated Oct. 3, 2019", 15 pgs.
"U.S. Appl. No. 15/460,060, Examiner Interview Summary dated Nov. 26, 2019", 4 pgs.
"U.S. Appl. No. 15/460,060, Final Office Action dated May 6, 2020", 42 pgs.
"U.S. Appl. No. 15/460,060, Non Final Office Action dated Oct. 30, 2019", 43 pgs.
"U.S. Appl. No. 15/460,060, Response filed Jan. 30, 2020 to Non Final Office Action dated Oct. 30, 2019", 15 pgs.
"U.S. Appl. No. 15/921,414, Non Final Office Action dated Apr. 16, 2020", 51 pgs.
"U.S. Appl. No. 16/197,905, Non Final Office Action dated Jan. 6, 2020", 6 pgs.
"U.S. Appl. No. 16/197,905, Response filed May 6, 2020 to Non Final Office Action dated Jan. 6, 2020", 7 pgs.
"U.S. Appl. No. 16/685,081, Examiner Interview Summary dated Feb. 18, 2020".
"U.S. Appl. No. 16/685,081, Non Final Office Action dated Jan. 3, 2020", 7 pgs.
"U.S. Appl. No. 16/685,081, Notice of Allowance dated Apr. 15, 2020", 6 pgs.
"Chinese Application Serial No. 201780029822.4, Office Action dated Feb. 14, 2020", w/ English Translation, 10 pgs.
"Chinese Application Serial No. 201780029824.3, Office Action dated Oct. 24, 2019", w/ English Translation, 13 pgs.
"Chinese Application Serial No. 201780029824.3, Response filed Mar. 9, 2020 to Office Action dated Oct. 24, 2019", w/ English claims, 66 pgs.
"European Application Serial No. 17767355.5, Extended European Search Report dated Nov. 7, 2019", 7 pgs.
"European Application Serial No. 17767355.5, Response filed Apr. 30, 2020 to Extended European Search Report dated Nov. 7, 2019", 16 pgs.
"European Application Serial No. 17767420.7, Extended European Search Report dated Mar. 11, 2020", 7 pgs.
"European Application Serial No. 17767453.8, Extended European Search Report dated Nov 18, 2019", 9 pgs.
"European Application Serial No. 17767469.4, Extended European Search Report dated Nov. 12, 2019", 8 pgs.
"European Application Serial No. 18768014.5, Extended European Search Report dated Mar. 18, 2020", 7 pgs.
"Japanese Application Serial No. 2019-550628, Notification of Reasons for Refusal dated Apr. 21, 2020", w/ English translation, 4 pgs.
"Japanese Application Serial No. 2019-550628, Voluntary Amendment dated Nov. 7, 2019", w/ English claims, voluntary amendment and PPH Request, 88 pgs.
"Korean Application Serial No. 10-2019-7030148, Office Action dated Dec. 20, 2019", w/ English translation, 6 pgs.
"Korean Application Serial No. 10-2019-7030148, Response filed Mar. 10, 2020 to Office Action dated Dec. 20, 2019", w/ English claims, 18 pgs.

"Korean Application Serial No. 10-2019-7030148, Voluntary Amendment filed Nov. 18, 2019", w/ English claims, PPH Request / Voluntary Amendment, 13 pgs.
"Taiwanese Application Serial No. 106108511, Office Action dated Feb. 12, 2020", w/ English Translation, 5 pgs.
"Taiwanese Application Serial No. 107134260, Office Action dated Feb. 17, 2020", w/English Translation, 4 pgs.
"U.S. Appl. No. 15/459,402, Response filed Nov. 2, 2020 to Final Office Action dated Sep. 2, 2020", 12 pgs.
"U.S. Appl. No. 15/459,897, Advisory Action dated Jun. 24, 2020", 3 pgs.
"U.S. Appl. No. 15/459,897, Response filed Jun. 15, 2020 to Final Office Action dated Apr. 14, 2020", 14 pgs.
"U.S. Appl. No. 15/460,060, Advisory Action dated Jul. 15, 2020", 3 pgs.
"U.S. Appl. No. 15/460,060. Response filed Jul. 6, 2020 to Final Office Action dated May 6, 2020", 16 pgs.
"U.S. Appl. No. 15/921,414, Advisory Action dated Nov. 19, 2020", 5 pgs.
"U.S. Appl. No. 15/921,414, Final Office Action dated Sep. 3, 2020", 54 pgs.
"U.S. Appl. No. 15/921,414, Response filed Jul. 16, 2020 to Non Final Office Action dated Apr. 16, 2020", 13 pgs.
"U.S. Appl. No. 15/921,414, Response filed Nov. 3, 2020 to Final Office Action dated Sep. 3, 2020", 14 pgs.
"U.S. Appl. No. 15/921,414. Response filed Dec. 3, 2020 to Advisory Action dated Nov. 19, 2020", 14 pgs.
"U.S. Appl. No. 16/197,905, Notice of Allowance dated May 22, 3020", 5 pgs.
"U.S. Appl. No. 16/353,739, Non Final Office Action dated Aug. 27, 2020", 29 pgs.
"Chinese Application Serial No. 201780028316.3, Response filed Nov. 12, 2020 to Office Action dated Jul. 14, 2020", w/ English claims, 20 pgs.
"Chinese Application Serial No. 201780029822.4, Response filed Jul. 6, 2020 to Office Action dated Feb. 14, 2020", w/ English claims, 11 pgs.
"Chinese Application Serial 201780029823.9, Office Action dated Jul. 9, 2020", w/ English Translation, 24 pgs.
"Chinese Application Serial No. 201780029824.3, Office Action dated May 12, 2020", w/ English translation, 8 pgs.
"Chinese Application Serial No. 201780029824.3, Response filed Sep. 25, 2020 to Office Action dated May 12, 2020", w/ English claims, 61 pgs.
"Chinese Application Serial No. 201780029841.7, Office Action dated Jul. 17, 2020", w/ English translation, 24 pgs.
"European Application Serial No. 17767453.8, Response filed May 13, 2020 to Extended European Search Report dated Nov. 18, 2019", 21 pgs.
"European Application Serial No. 17767469.4, Response filed May 22, 2020 to Extended European Search Report dated Nov. 12, 2019", 14 pgs.
"European Application Serial No. 18768014.5, Response filed Oct. 5, 2020 to Extended European Search Report dated Mar. 18, 2020", 14 pgs.
"International Application Serial No. PCT/US2020/022653, International Search Report dated Jul. 16, 2020", 4 pgs.
"International Application Serial No. PCT/US2020/022653, Written Opinion dated Jul. 16, 2020", 8 pgs.
"Japanese Application Serial No. 2019-550628, Response filed Jun. 18, 2020 to Notification of Reasons for Refusal dated Apr. 21, 2020", w/ English claims, 15 pgs.
"Japanese Application Serial No. 2020-148942, Voluntary Amendment filed Oct. 1, 2020", w/ English claims, 14 pgs.
"Taiwanese Application Serial No. 106108511, Response filed Aug. 7, 2020 to Office Action dated Feb. 12, 2020", w/ English translation of replacement pages, 185 pgs.
"Taiwanese Application Serial No. 107134260, Response filed Aug. 7, 2020 to Office Action dated Feb. 17, 2020", w/English translation of replacement pages of Specification, 166 pgs.
"Korean Application Serial No. 10-2018-7029439, Notice of Preliminary Rejection dated Jan. 5, 2021", w English translation, 5 pgs.

(56) References Cited

OTHER PUBLICATIONS

"U.S. Appl. No. 16/353,739, Response filed Jan. 22, 2021 to Non Final Office Action dated Aug. 27, 2020", 15 pgs.

"Korean Application Serial No. 10-2018-7029261, Notice of Preliminary Rejection dated Jan. 1, 2021", w English translation, 19 pgs.

"Japanese Application Serial No. 2018-548842, Notification of Reasons for Refusal dated Mar. 16, 2021", w English Translation, 8 pgs.

"Chinese Application Serial No. 201880031338.X, Office Action dated Feb. 23, 2021", w English Translation, 13 pgs.

"European Application Serial No. 17767442.1, Extended European Search Report dated Mar. 25, 2021", 8 pgs.

"Chinese Application Serial No. 201780029841.7, Office Action dated Mar. 31, 2021", w English Translation, 23 pgs.

"Chinese Application Serial No. 201780029823.9, Office Action dated Apr. 8, 2021", w English Translation, 8 pgs.

\* cited by examiner

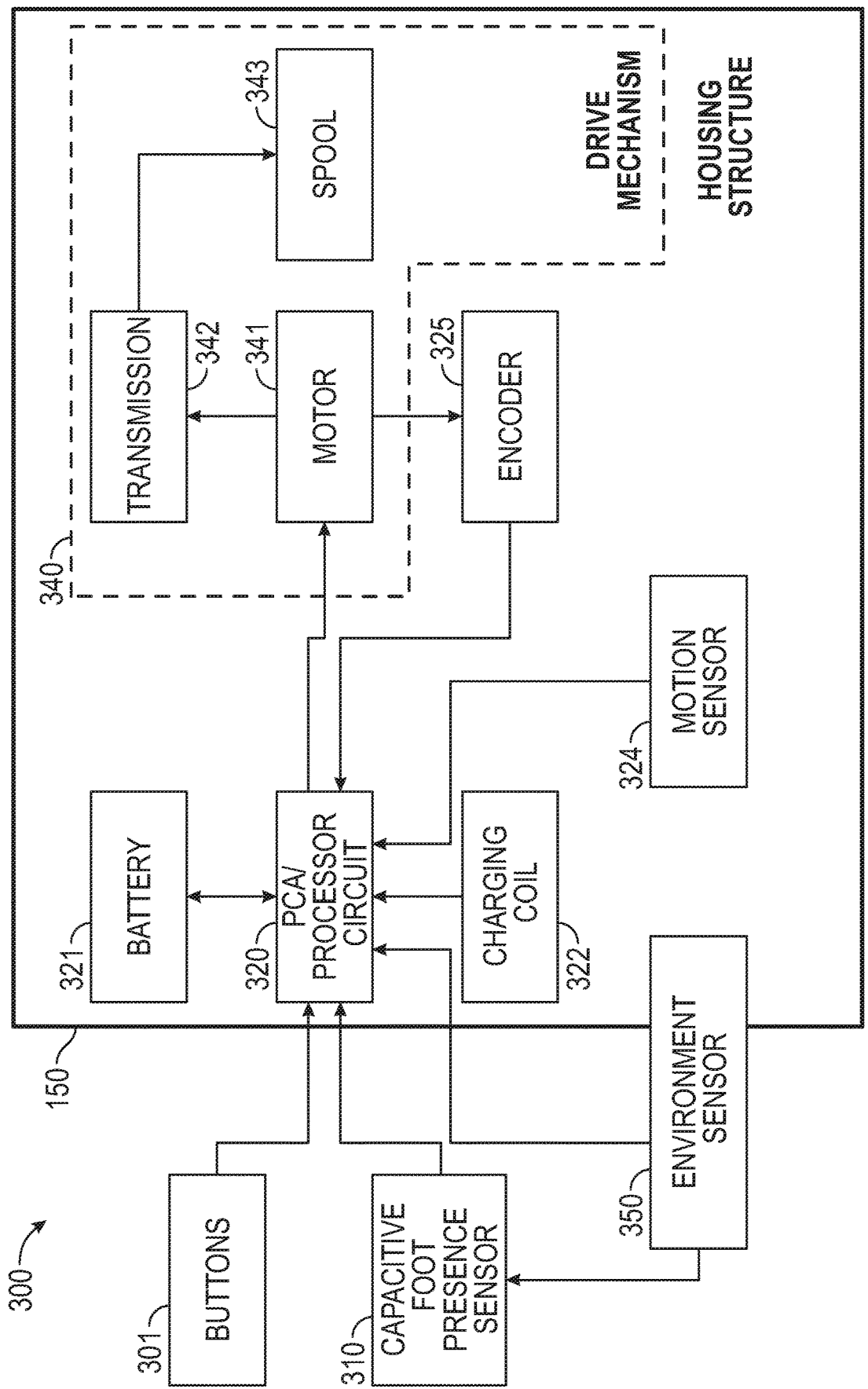

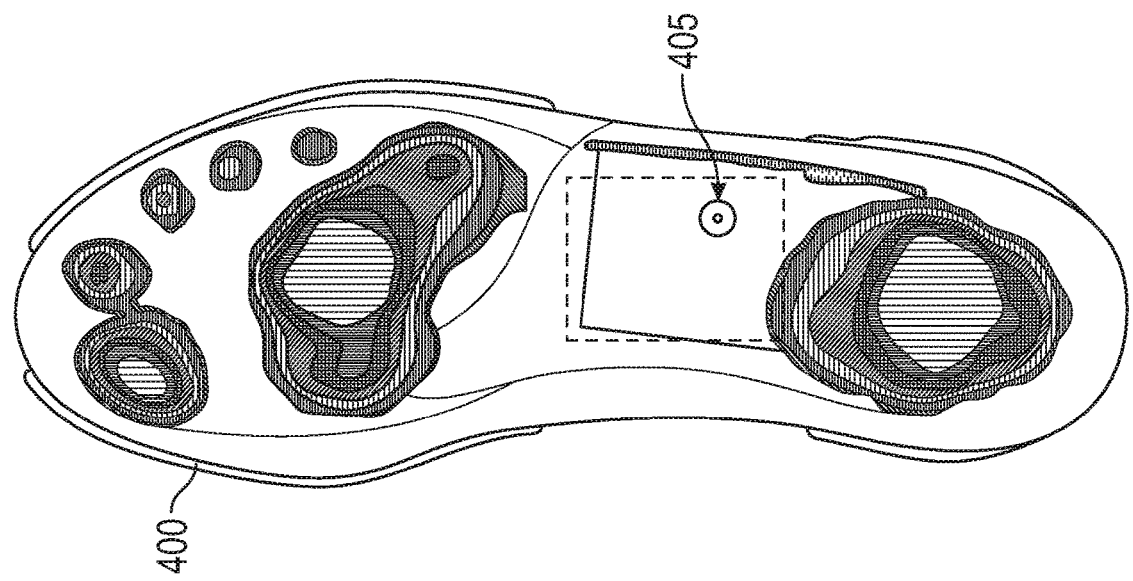
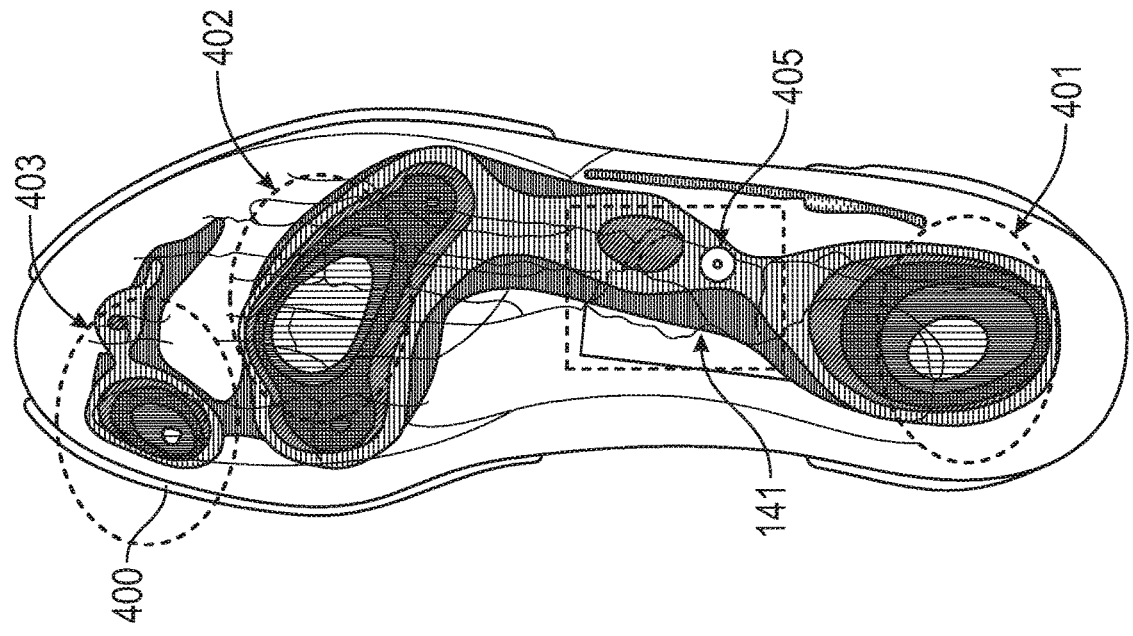
FIG. 4

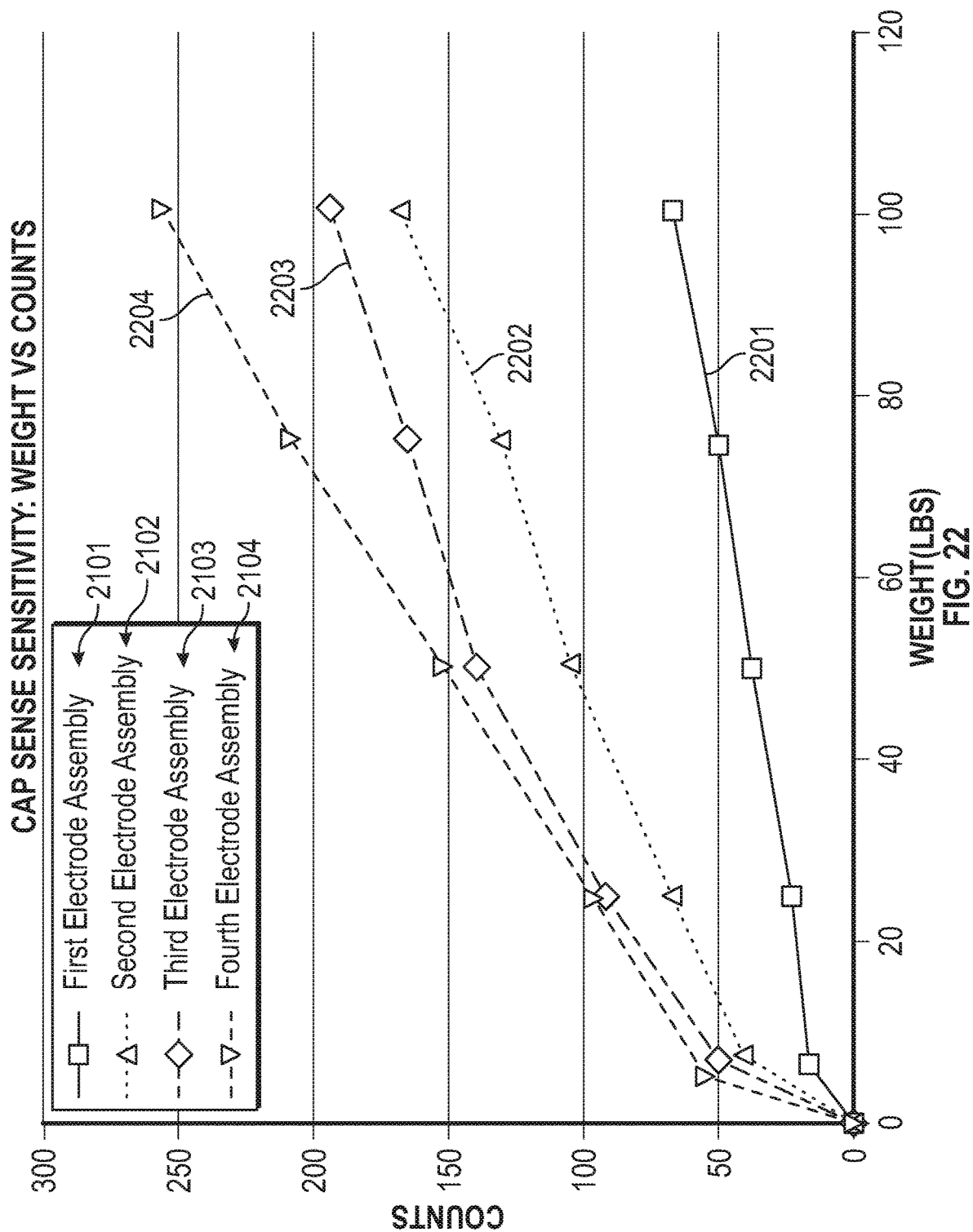

FOOT PRESENCE SIGNAL PROCESSING USING VELOCITY

CLAIM OF PRIORITY

This application is a U.S. National Stage Application under 35 U.S.C. 371 from International Application No. PCT/US2018/022466, filed Mar. 14, 2018, which application claims the benefit of priority of U.S. Provisional Patent Application Ser. No. 62/556,103, filed on Sep. 8, 2017, and this application is a Continuation-in-part of U.S. patent application Ser. No. 15/610,179, filed on May 31, 2017, which is a Continuation of U.S. patent application Ser. No. 15/458,625, filed on Mar. 14, 2017, and this application is a Continuation-in-part of PCT Patent Application Number PCT/US2017/022342, filed on Mar. 14, 2017, and this application is a Continuation-in-part of U.S. patent application Ser. No. 15/460,060, filed on Mar. 15, 2017, and this application is a Continuation-in-part of PCT Patent Application Number PCT/US2017/022576, filed on Mar. 15, 2017, and this application is a Continuation-in-part of U.S. patent application Ser. No. 15/459,889, filed on Mar. 15, 2017, and this application is a Continuation-in-part of PCT Patent Application Number PCT/US2017/022533, filed on Mar. 15, 2017, and this application is a Continuation-in-part of U.S. patent application Ser. No. 15/459,897, filed on Mar. 15, 2017, and this application is a Continuation-in-part of PCT Patent Application Number PCT/US2017/022548, filed on Mar. 15, 2017, and this application is a Continuation-in-part of Taiwan Patent Application Number 106108511, filed on Mar. 15, 2017, and this application is a Continuation-in-part of U.S. patent application Ser. No. 15/459,402, filed on Mar. 15, 2017, and this application is a Continuation-in-part of PCT Patent Application Number PCT/US2017/022489, filed on Mar. 15, 2017, each of which is herein incorporated by reference in its entirety.

BACKGROUND

Various shoe-based sensors have been proposed to monitor various conditions. For example, Brown, in U.S. Pat. No. 5,929,332, titled "Sensor shoe for monitoring the condition of a foot", provides several examples of shoe-based sensors. Brown mentions a foot force sensor can include an insole made of layers of relatively thin, planar, flexible, resilient, dielectric material. The foot force sensor can include electrically conductive interconnecting means that can have an electrical resistance that changes based on an applied compressive force.

Brown further discusses a shoe to be worn by diabetic persons, or persons afflicted with various types of foot maladies, where excess pressure exerted upon a portion of the foot tends to give rise to ulceration. The shoe body can include a force sensing resistor (FSR), and a switching circuit coupled to the resistor can activate an alarm unit to warn a wearer that a threshold pressure level is reached or exceeded.

Devices for automatically tightening an article of footwear have been previously proposed. Liu, in U.S. Pat. No. 6,691,433, titled "Automatic tightening shoe", provides a first fastener mounted on a shoe's upper portion, and a second fastener connected to a closure member and capable of removable engagement with the first fastener to retain the closure member at a tightened state. Liu teaches a drive unit mounted in the heel portion of the sole. The drive unit includes a housing, a spool rotatably mounted in the housing, a pair of pull strings and a motor unit. Each string has a first end connected to the spool and a second end corresponding to a string hole in the second fastener. The motor unit is coupled to the spool. Liu teaches that the motor unit is operable to drive rotation of the spool in the housing to wind the pull strings on the spool for pulling the second fastener towards the first fastener. Liu also teaches a guide tube unit that the pull strings can extend through.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 3 illustrates generally a block diagram of components of a motorized lacing system, according to an example embodiment.

FIG. 4 is a diagram illustrating pressure distribution data for a nominal or average foot (left) and for a high arch foot (right) in a footwear article when a user of a footwear article is standing.

FIG. 22 illustrates generally an example of a chart that shows a relationship between sensor sensitivity and sensor shape.

DETAILED DESCRIPTION

Figure 1:
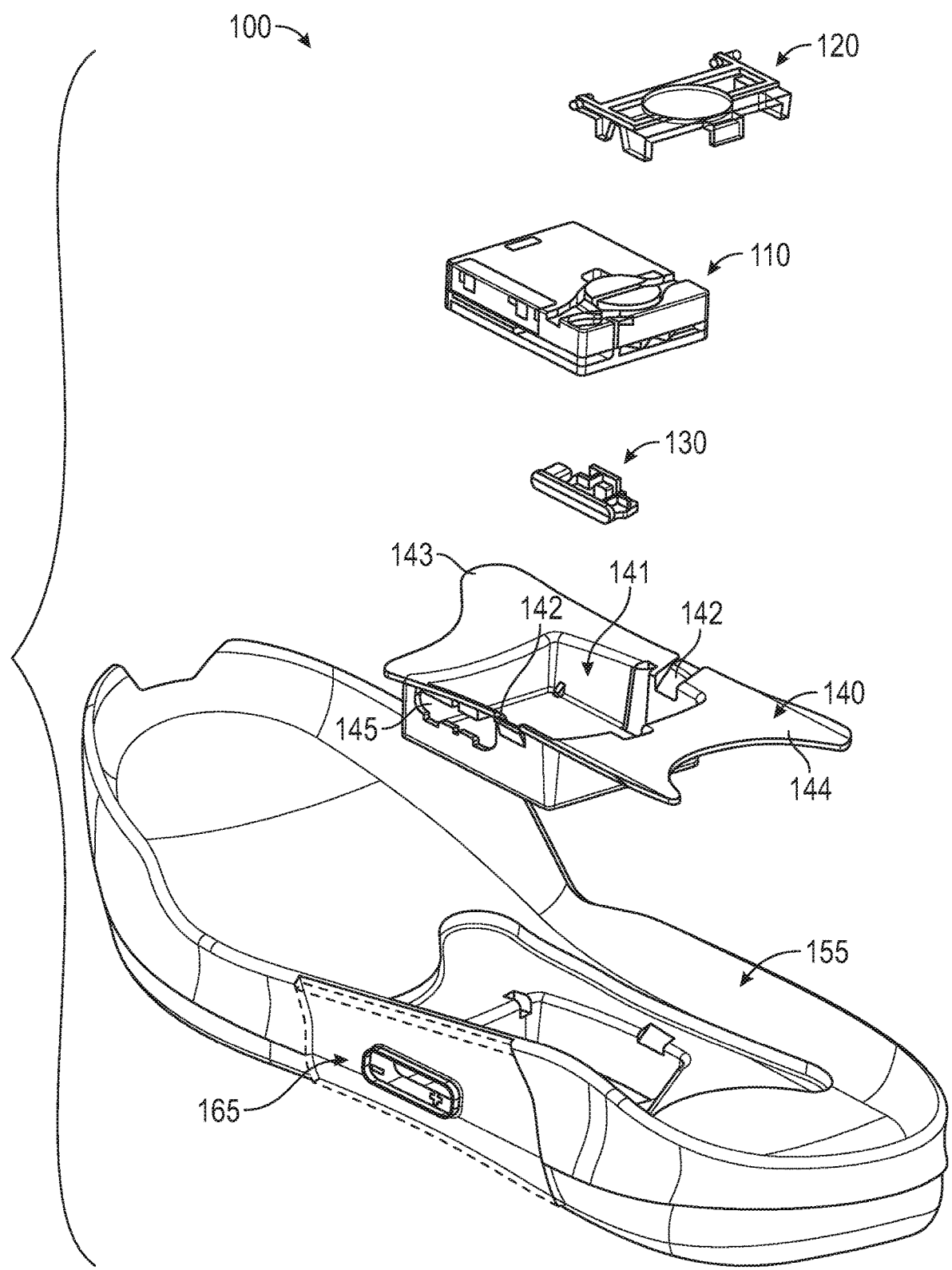
FIG. 1 illustrates generally an exploded view of components of an active footwear article, according to an example embodiment.

The concept of self-tightening shoelaces was first widely popularized by the fictitious power-laced Nike® sneakers worn by Marty McFly in the movie Back to the Future II, which was released back in 1989. While Nike® has since released at least one version of power-laced sneakers similar in appearance to the movie prop version from Back to the Future II, the internal mechanical systems and surround footwear platform employed do not necessarily lend themselves to mass production or daily use. Additionally, previous designs for motorized lacing systems comparatively suffered from problems such as high cost of manufacture, complexity, assembly challenges, lack of serviceability, and weak or fragile mechanical mechanisms, to highlight just a few of the many issues. The present inventors have developed a modular footwear platform to accommodate motorized and non-motorized lacing engines that solves some or all of the problems discussed above, among others. The components discussed below provide various benefits including, but not limited to, serviceable components, interchangeable automated lacing engines, robust mechanical design, robust control algorithms, reliable operation, streamlined assembly processes, and retail-level customization. Various other benefits of the components described below will be evident to persons of skill in the relevant arts.

In an example, a modular automated lacing footwear platform includes a mid-sole plate secured to a mid-sole in a footwear article for receiving a lacing engine. The design of the mid-sole plate allows a lacing engine to be added to the footwear platform as late as at a point of purchase. The mid-sole plate, and other aspects of the modular automated footwear platform, allow for different types of lacing engines to be used interchangeably. For example, the motorized lacing engine discussed below could be changed out for a human-powered lacing engine. Alternatively, a fully-automatic motorized lacing engine with foot presence sensing or other features can be accommodated within the standard mid-sole plate.

The automated footwear platform discussed herein can include an outsole actuator interface to provide tightening control to the end user as well as visual feedback, for example, using LED lighting projected through translucent protective outsole materials. The actuator can provide tactile and visual feedback to the user to indicate status of the lacing engine or other automated footwear platform components.

In an example, the footwear platform includes a foot presence sensor configured to detect when a foot is present in the shoe. When a foot is detected, then one or more footwear functions or processes can be initiated, such as automatically and without a further user input or command. For example, upon detection that a foot is properly seated in the footwear against an insole, a control circuit can automatically initiate lace tightening, data collection, footwear diagnostics, or other processes.

Prematurely activating or initiating an automated lacing or footwear tightening mechanism can detract from a user's experience with the footwear. For example, if a lacing engine is activated before a foot is completely seated against an insole, then the user may have a difficult time getting a remainder of his or her foot into the footwear, or the user may have to manually adjust a lacing tension. The present inventors have thus recognized that a problem to be solved includes determining whether a foot is seated properly or fully in a footwear article, such as with toe, mid-sole, and heel portions properly aligned with corresponding portions of an insole. The inventors have further recognized that the problem includes accurately determining a foot location or foot orientation using as few sensors as possible, such as to reduce sensor costs and assembly costs, and to reduce device complexity.

A solution to these problems includes providing a sensor in an arch and/or heel region of the footwear. In an example, the sensor is a capacitive sensor that is configured to sense changes in a nearby electric field. Changes in the electric field, or capacitance changes, can be realized as a foot enters or exits the footwear, including while some portions of the foot are at a greater distance from the sensor than other portions of the foot. In an example, the capacitive sensor is integrated with or housed within a lacing engine enclosure. In an example, at least a portion of the capacitive sensor is provided outside of the lacing engine enclosure and includes one or more conductive interconnects to power or processing circuitry inside the enclosure.

A capacitive sensor suitable for use in foot presence detection can have various configurations. The capacitive sensor can include a plate capacitor wherein one plate is configured to move relative to another, such as in response to pressure or to a change of pressure exerted on one or more of the plates. In an example, the capacitive sensor includes multiple traces, such as arranged substantially in a plane that is parallel to or coincident with an upper surface of an insole. Such traces can be laterally separated by an air gap (or other material, such as Styrofoam) and can be driven selectively or periodically by an AC drive signal provided by an excitation circuit. In an example, the electrodes can have an interleaved, comb configuration. Such a capacitive sensor can provide a changing capacitance signal that is based on movement of the electrodes themselves relative to one another and based on interference of the electric field near the electrodes due to presence or absence or movement of a foot or other object.

In an example, a capacitance-based sensor can be more reliable than a mechanical sensor, for example, because the capacitance-based sensor need not include moving parts. Electrodes of a capacitance-based sensor can be coated or covered by a durable, electric field-permeable material, and thus the electrodes can be protected from direct exposure to environmental changes, wetness, spillages, dirt, or other contaminating agents, and humans or other materials are not in direct contact with the sensor's electrodes.

In an example, the capacitive sensor provides an analog output signal indicative of a magnitude of a capacitance, or indicative of a change of capacitance, that is detected by the sensor. The output signal can have a first value (e.g., corresponding to a low capacitance) when a foot is present near the sensor, and the output signal have a different second value (e.g., corresponding to a high capacitance) when a foot is absent.

In an example, the output signal when the foot is present can provide further information. For example, there can be a detectable variation in the capacitance signal that correlates to step events. In addition, there can be a detectable long-term drift in the capacitance signal that can indicate wear-and-tear and/or remaining life in shoe components like insoles, orthotics, or other components.

In an example, the capacitive sensor includes or is coupled to a capacitance-to-digital converter circuit configured to provide a digital signal indicative of a magnitude of a capacitance sensed by the sensor. In an example, the capacitive sensor includes a processor circuit configured to provide an interrupt signal or logic signal that indicates whether a sensed capacitance value meets a specified threshold capacitance condition. In an example, the capacitive sensor measures a capacitance characteristic relative to a baseline or reference capacitance value, and the baseline or reference can be updated or adjusted such as to accommodate environment changes or other changes that can influence sensed capacitance values.

In an example, a capacitive sensor is provided under-foot near an arch or heel region of an insole of a shoe. The capacitive sensor can be substantially planar or flat. The capacitive sensor can be rigid or flexible and configured to conform to contours of a foot. In some cases, an air gap, such as can have a relatively low dielectric constant or low relative permittivity, can exist between a portion of the capacitive sensor and the foot when the shoe is worn. A gap filler, such as can have a relatively high dielectric constant or greater relative permittivity than air, can be provided above the capacitive sensor in order to bridge any airspace between the capacitive sensor and a foot surface. The gap filler can be compressible or incompressible. In an example, the gap filler is selected to provide a suitable compromise between dielectric value and suitability for use in footwear in order to provide a sensor with adequate sensitivity and user comfort under foot.

The following discusses various components of an automated footwear platform including a motorized lacing engine, a foot presence sensor, a mid-sole plate, and various other components of the platform. While much of this disclosure focuses on foot presence sensing as a trigger for a motorized lacing engine, many aspects of the discussed designs are applicable to a human-powered lacing engine, or other circuits or features that can interface with a foot presence sensor, such as to automate other footwear functions like data collection or physiologic monitoring. The term "automated," such as used in "automated footwear platform," is not intended to cover only a system that operates without a specified user input. Rather, the term "automated footwear platform" can include various electrically powered and human-powered, automatically activated and human activated, mechanisms for tightening a lacing or retention system of the footwear, or for controlling other aspects of active footwear.

FIG. 1 illustrates generally an exploded view of components of an active footwear article, according to an example embodiment. The example of FIG. 1 includes a motorized lacing system 100 with a lacing engine 110, a lid 120, an actuator 130, a mid-sole plate 140, a mid-sole 155, and an outsole 165. The lacing engine 110 can include a user-replaceable component in the system 100, and can include or can be coupled to one or more foot presence sensors. In an example, the lacing engine 110 includes, or is coupled to, a capacitive foot presence sensor. The capacitive foot presence sensor, not shown in the example of FIG. 1, can include multiple electrodes arranged on a foot-facing side of the lacing engine 110. In an example, the electrodes of the capacitive foot presence sensor can be housed within the lacing engine 110, can be integrated with the housing of the lacing engine 110, or can be disposed elsewhere near the lacing engine 110 and coupled to power or processing circuitry inside of the lacing engine 110 using one or more electrical conductors.

Assembling the motorized lacing system 100 in the example of FIG. 1 starts with securing the mid-sole plate 140 within the mid-sole 155. Next, the actuator 130 can be inserted into an opening in a lateral side of the mid-sole plate 140, such as opposite to interface buttons that can be embedded in the outsole 165. Next, the lacing engine 110 can be inserted into the mid-sole plate 140. In an example, the lacing engine 110 can be coupled with one or more sensors that are disposed elsewhere in the footwear. Other assembly methods can be similarly performed to construct the motorized lacing system 100.

In an example, the lacing system 100 is inserted under a continuous loop of lacing cable and the lacing cable is aligned with a spool in the lacing engine 110. To complete the assembly, the lid 120 can be inserted into securing means in the mid-sole plate 140, secured into a closed position, and latched into a recess in the mid-sole plate 140. The lid 120 can capture the lacing engine 110 and can assist in maintaining alignment of a lacing cable during operation.

The mid-sole plate 140 includes a lacing engine cavity 141, medial and lateral lace guides 142, an anterior flange 143, a posterior flange 144, superior (top) and inferior (bottom) surfaces, and an actuator cutout 145. The lacing engine cavity 141 is configured to receive the lacing engine 110. In this example, the lacing engine cavity 141 retains the lacing engine 110 in lateral and anterior/posterior directions, but does not include a feature to lock the lacing engine 110 into the cavity 141. Optionally, the lacing engine cavity 141 includes detents, tabs, or other mechanical features along one or more sidewalls to more positively retain the lacing engine 110 within the lacing engine cavity 141.

The lace guides 142 can assist in guiding a lacing cable into position with the lacing engine 110. The lace guides 142 can include chamfered edges and inferiorly slated ramps to assist in guiding a lacing cable into a desired position with respect to the lacing engine 110. In this example, the lace guides 142 include openings in the sides of the mid-sole plate 140 that are many times wider than a typical lacing cable diameter, however other dimensions can be used.

In the example of FIG. 1, the mid-sole plate 140 includes a sculpted or contoured anterior flange 143 that extends further on a medial side of the mid-sole plate 140. The example anterior flange 143 is designed to provide additional support under the arch of the footwear platform. However, in other examples the anterior flange 143 may be less pronounced on the medial side. In this example, the posterior flange 144 includes a contour with extended portions on both medial and lateral sides. The illustrated posterior flange 144 can provide enhanced lateral stability for the lacing engine 110.

In an example, one or more electrodes can be embedded in or disposed on the mid-sole plate 140, and can form a portion of a foot presence sensor, such as a portion of a capacitive foot presence sensor. In an example, the lacing engine 110 includes a sensor circuit that is electrically coupled to the one or more electrodes on the mid-sole plate 140. The sensor circuit can be configured to use electric field or capacitance information sensed from the electrodes to determine whether a foot is present or absent in a region adjacent to the mid-sole plate 140. In an example, the electrodes extend from an anterior-most edge of the anterior flange 143 to a posterior-most edge of the posterior flange 144, and in other examples the electrodes extend over only part of one or both of the flanges.

In an example, the footwear or the motorized lacing system 100 includes or interfaces with one or more sensors that can monitor or determine a foot presence in the footwear, foot absence from the footwear, or foot position characteristic within the footwear. Based on information from one or more such foot presence sensors, the footwear including the motorized lacing system 100 can be configured to perform various functions. For example, a foot presence sensor can be configured to provide binary information about whether a foot is present or not present in the footwear. In an example, a processor circuit coupled to the foot presence sensor receives and interprets digital or analog signal information and provides the binary information about whether a foot is present or not present in the footwear. If a binary signal from the foot presence sensor indicates that a foot is present, then the lacing engine 110 in the motorized lacing system 100 can be activated, such as to automatically increase or decrease a tension on a lacing cable, or other footwear constricting means, such as to tighten or relax the footwear about a foot. In an example, the lacing engine 110, or other portion of a footwear article, includes a processor circuit that can receive or interpret signals from a foot presence sensor.

In an example, a foot presence sensor can be configured to provide information about a location of a foot as it enters footwear. The motorized lacing system 100 can generally be activated, such as to tighten a lacing cable, only when a foot is appropriately positioned or seated in the footwear, such as against all or a portion of the footwear article's insole. A foot presence sensor that senses information about a foot travel or location can provide information about whether a foot is fully or partially seated such as relative to an insole or relative to some other feature of the footwear article. Automated lacing procedures can be interrupted or delayed until information from the sensor indicates that a foot is in a proper position.

In an example, a foot presence sensor can be configured to provide information about a relative location of a foot inside of footwear. For example, the foot presence sensor can be configured to sense whether the footwear is a good "fit" for a given foot, such as by determining a relative position of one or more of a foot's arch, heel, toe, or other component, such as relative to the corresponding portions of the footwear that are configured to receive such foot components. In an example, the foot presence sensor can be configured to sense whether a position of a foot or a foot component changes over time relative to a specified or previously-recorded reference position, such as due to loosening of a lacing cable over time, or due to natural expansion and contraction of a foot itself.

In an example, a foot presence sensor can include an electrical, magnetic, thermal, capacitive, pressure, optical, or other sensor device that can be configured to sense or receive information about a presence of a body. For example, an electrical sensor can include an impedance sensor that is configured to measure an impedance characteristic between at least two electrodes. When a body such as a foot is located proximal or adjacent to the electrodes, the electrical sensor can provide a sensor signal having a first value, and when a body is located remotely from the electrodes, the electrical sensor can provide a sensor signal having a different second value. For example, a first impedance value can be associated with an empty footwear condition, and a lesser second impedance value can be associated with an occupied footwear condition.

An electrical sensor can include an AC signal generator circuit and an antenna that is configured to emit or receive high frequency signal information, such as including radio frequency information. Based on proximity of a body relative to the antenna, one or more electrical signal characteristics, such as impedance, frequency, or signal amplitude, can be received and analyzed to determine whether a body is present. In an example, a received signal strength indicator (RSSI) provides information about a power level in a received radio signal. Changes in the RSSI, such as relative to some baseline or reference value, can be used to identify a presence or absence of a body. In an example, WiFi frequencies can be used, for example in one or more of 2.4 GHz, 3.6 GHz, 4.9 GHz, 5 GHz, and 5.9 GHz bands. In an example, frequencies in the kilohertz range can be used, for example, around 400 kHz. In an example, power signal changes can be detected in milliwatt or microwatt ranges.

A foot presence sensor can include a magnetic sensor. A first magnetic sensor can include a magnet and a magnetometer. In an example, a magnetometer can be positioned in or near the lacing engine 110. A magnet can be located remotely from the lacing engine 110, such as in a secondary sole, or insole, that is configured to be worn above the outsole 165. In an example, the magnet is embedded in foam or in another compressible material of the secondary sole. As a user depresses the secondary sole such as when standing or walking, corresponding changes in the location of the magnet relative to the magnetometer can be sensed and reported via a sensor signal.

A second magnetic sensor can include a magnetic field sensor that is configured to sense changes or interruptions (e.g., via the Hall effect) in a magnetic field. When a body is proximal to the second magnetic sensor, the sensor can generate a signal that indicates a change to an ambient magnetic field. For example, the second magnetic sensor can include a Hall effect sensor that varies a voltage output signal in response to variations in a detected magnetic field. Voltage changes at the output signal can be due to production of a voltage difference across an electric signal conductor, such as transverse to an electric current in the conductor and a magnetic field perpendicular to the current.

In an example, the second magnetic sensor is configured to receive an electromagnetic field signal from a body. For example, Varshavsky et al., in U.S. Pat. No. 8,752,200, titled "Devices, systems and methods for security using magnetic field based identification", teaches using a body's unique electromagnetic signature for authentication. In an example, a magnetic sensor in a footwear article can be used to authenticate or verify that a present user is a shoe's owner via a detected electromagnetic signature, and that the article should lace automatically, such as according to one or more specified lacing preferences (e.g., tightness profile) of the owner.

In an example, a foot presence sensor includes a thermal sensor that is configured to sense a change in temperature in or near a portion of the footwear. When a wearer's foot enters a footwear article, the article's internal temperature changes when the wearer's own body temperature differs from an ambient temperature of the footwear article. Thus the thermal sensor can provide an indication that a foot is likely to be present or not based on a temperature change.

In an example, a foot presence sensor includes a capacitive sensor that is configured to sense a change in capacitance. The capacitive sensor can include a single plate or electrode, or the capacitive sensor can include a multiple-plate or multiple-electrode configuration. Various examples of capacitive-type foot presence sensors are further described herein.

In an example, a foot presence sensor includes an optical sensor. The optical sensor can be configured to determine whether a line-of-sight is interrupted, such as between opposite sides of a footwear cavity. In an example, the optical sensor includes a light sensor that can be covered by a foot when the foot is inserted into the footwear. When the sensor indicates a change in a sensed light or brightness condition, an indication of a foot presence or position can be provided.

Any of the different types of foot presence sensors discussed herein can be used independently, or information from two or more different sensors or sensor types can be used together to provide more information about a foot presence, absence, orientation, goodness-of-fit with the footwear, or other information about a foot and/or its relationship with the footwear.

Figure 2A:
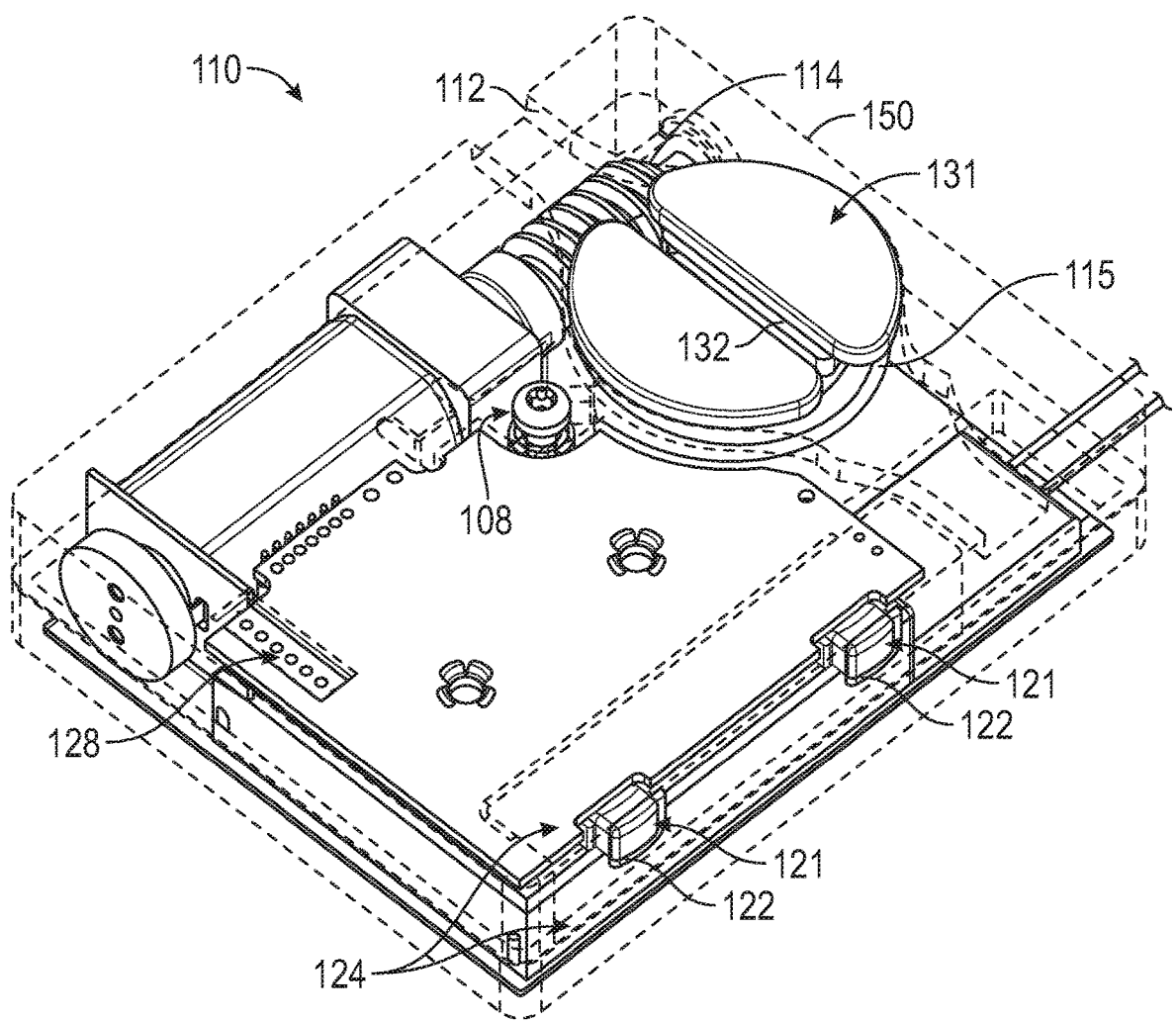
FIGS. 2A-2C illustrate generally a sensor system and motorized lacing engine, according to some example embodiments.
Figure 2B:
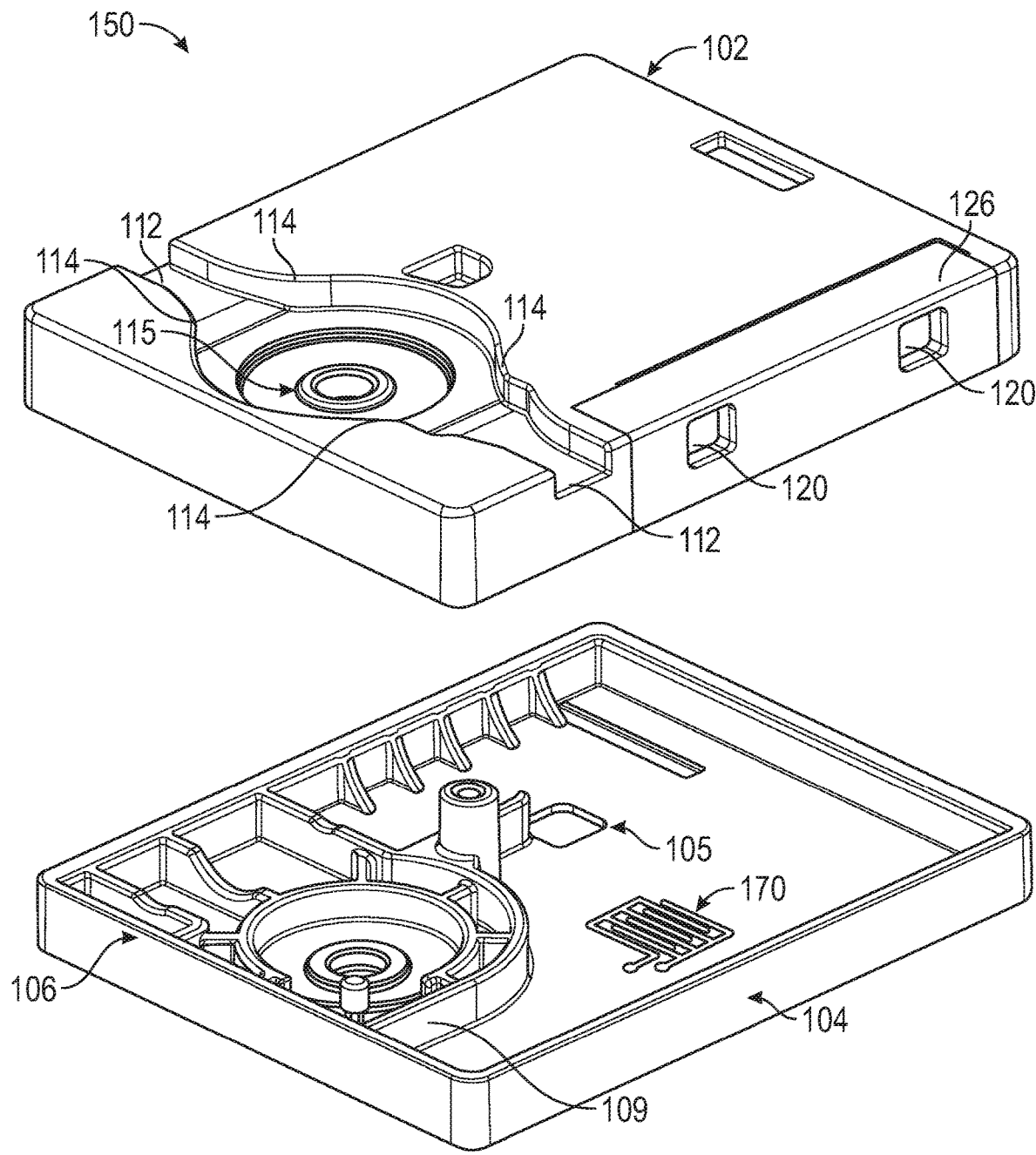
Figure 2C:
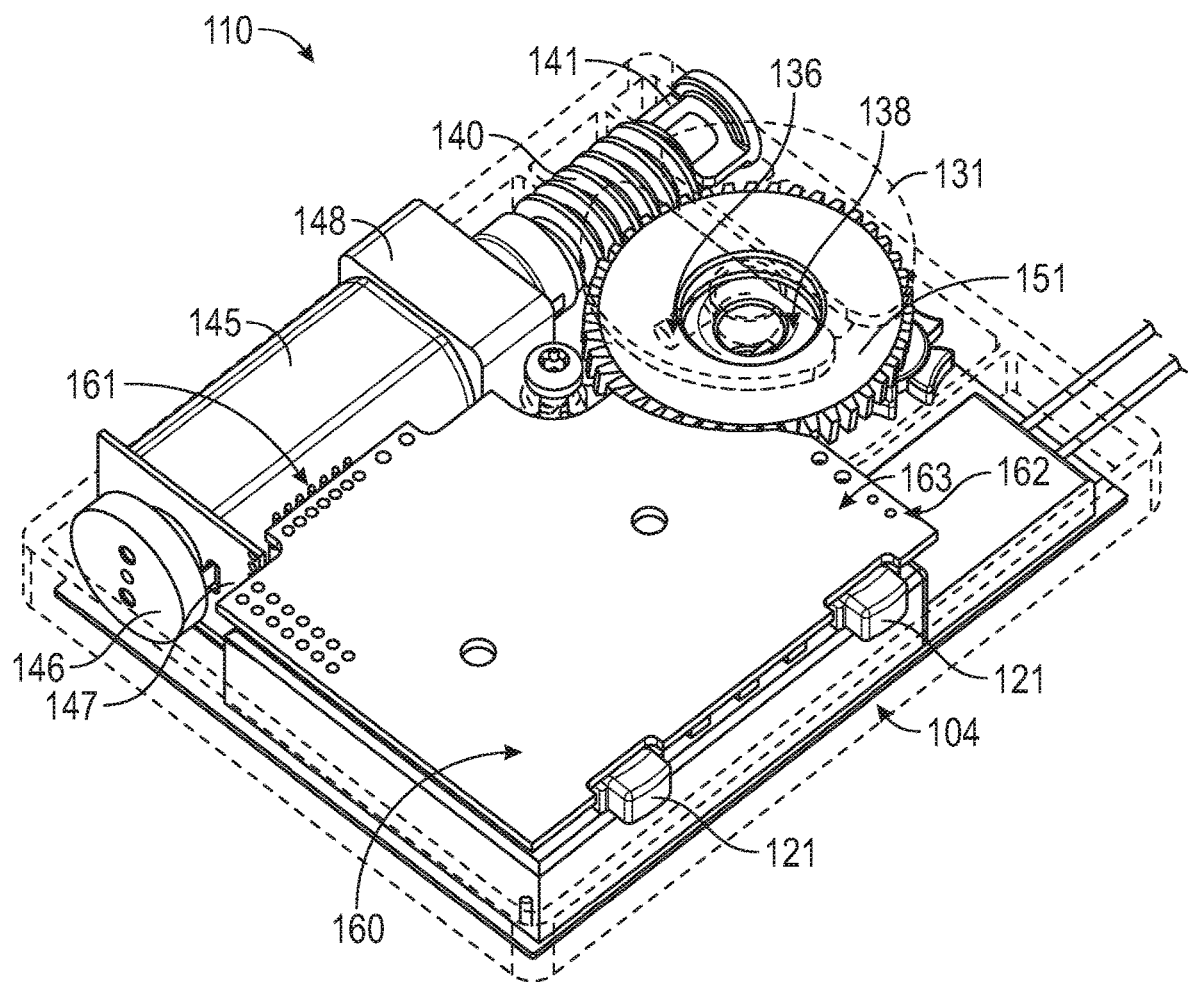

FIGS. 2A-2C illustrate generally a sensor system and motorized lacing engine, according to some example embodiments. FIG. 2A introduces various external features of an example lacing engine 110, including a housing structure 150, case screw 108, lace channel 112 (also referred to as lace guide relief 112), lace channel transition 114, spool recess 115, button openings 122, buttons 121, button membrane seal 124, programming header 128, spool 131, and lace groove 132 in the spool 131. Other designs can similarly be used. For example, other switch types can be used, such as sealed dome switches, or the membrane seal 124 can be eliminated, etc. In an example, the lacing engine 110 can include one or more interconnects or electrical contacts for interfacing circuitry internal to the lacing engine 110 with circuitry outside of the lacing engine 110, such as an external foot presence sensor (or component thereof), an external actuator like a switch or button, or other devices or components.

The lacing engine 110 can be held together by one or more screws, such as the case screw 108. The case screw 108 can be positioned near the primary drive mechanisms to enhance structural integrity of the lacing engine 110. The case screw 108 also functions to assist the assembly process, such as holding the housing structure 150 together for ultra-sonic welding of exterior seams.

In the example of FIG. 2A, the lacing engine 110 includes the lace channel 112 to receive a lace or lace cable once the engine is assembled into the automated footwear platform. The lace channel 112 can include a channel wall with chamfered edges to provide a smooth guiding surface against or within which a lace cable can travel during operation. Part of the smooth guiding surface of the lace channel 112 can include a channel transition 114, which can be a widened portion of the lace channel 112 leading into the spool recess 115. The spool recess 115 transitions from the channel transition 114 into generally circular sections that conform closely to a profile of the spool 131. The spool recess 115 can assist in retaining a spooled lace cable, as well as in retaining a position of the spool 131. Other aspects of the design can provide other means to retain the spool 131. In the example of FIG. 2A, the spool 131 is shaped similarly to half of a yo-yo with a lace groove 132 running through a flat top surface and a spool shaft (not shown in FIG. 2A) extending inferiorly from the opposite side.

A lateral side of the lacing engine 110 includes button openings 122 that house buttons 121 that can be configured to activate or adjust one or more features of the automated footwear platform. The buttons 121 can provide an external interface for activation of various switches included in the lacing engine 110. In some examples, the housing structure 150 includes a button membrane seal 124 to provide protection from dirt and water. In this example, the button membrane seal 124 is up to a few mils (thousandths of an inch) thick clear plastic (or similar material) that can be adhered from a superior surface of the housing structure 150, such as over a corner and down a lateral side. In another example, the button membrane seal 124 is an approximately 2-mil thick vinyl adhesive backed membrane covering the buttons 121 and button openings 122. Other types of buttons and sealants can be similarly used.

FIG. 2B is an illustration of housing structure 150 including a top section 102 and a bottom section 104. In this example, the top section 102 includes features such as the case screw 108, lace channel 112, lace channel transition 114, spool recess 115, button openings 122, and a button seal recess 126. In an example, the button seal recess 126 is a portion of the top section 102 that is relieved to provide an inset for the button membrane seal 124.

In the example of FIG. 2B, the bottom section 104 includes features such as a wireless charger access 105, a joint 106, and a grease isolation wall 109. Also illustrated, but not specifically identified, is the case screw base for receiving case screw 108, as well as various features within the grease isolation wall 109 for holding portions of a drive mechanism. The grease isolation wall 109 is designed to retain grease, or similar compounds surrounding the drive mechanism, away from various electrical components of the lacing engine 110.

The housing structure 150 can include, in one or both of the top and bottom sections 102 and 104, one or more electrodes 170 embedded in or applied on a structure surface. The electrodes 170 in the example of FIG. 2B are shown coupled to the bottom section 104. In an example, the electrodes 170 comprise a portion of a capacitance-based foot presence sensor circuit (see, e.g., the foot presence sensor 310 discussed herein). Additionally or alternatively, the electrodes 170 can be coupled to the top section 102. Electrodes 170 coupled to the top or bottom sections 102 or 104 can be used for wireless power transfer and/or as a portion of a capacitance-based foot presence sensor circuit. In an example, the electrodes 170 include one or more portions that are disposed on an outside surface of the housing structure 150, and in another example the electrodes 170 include one or more portions that are disposed on an inside surface of the housing structure 150.

FIG. 2C is an illustration of various internal components of lacing engine 110, according to an example embodiment. In this example, the lacing engine 110 further includes a spool magnet 136, O-ring seal 138, worm drive 140, bushing 141, worm drive key, gear box 148, gear motor 145, motor encoder 146, motor circuit board 147, worm gear 151, circuit board 160, motor header 161, battery connection 162, and wired charging header 163. The spool magnet 136 assists in tracking movement of the spool 131 though detection by a magnetometer (not shown in FIG. 2C). The o-ring seal 138 functions to seal out dirt and moisture that could migrate into the lacing engine 110 around the spool shaft. The circuit board 160 can include one or more interfaces or interconnects for a foot presence sensor, such as the capacitive foot presence sensor 310 described below. In an example, the circuit board 160 includes one or more traces or conductive planes that provide a portion of the foot presence sensor 310.

In this example, major drive components of the lacing engine 110 include the worm drive 140, worm gear 151, gear motor 145 and gear box 148. The worm gear 151 is designed to inhibit back driving of the worm drive 140 and gear motor 145, which means the major input forces coming in from the lacing cable via the spool 131 can be resolved on the comparatively large worm gear and worm drive teeth. This arrangement protects the gear box 148 from needing to include gears of sufficient strength to withstand both the dynamic loading from active use of the footwear platform or tightening loading from tightening the lacing system. The worm drive 140 includes additional features to assist in protecting various fragile portions of the drive system, such as the worm drive key. In this example, the worm drive key is a radial slot in the motor end of the worm drive 140 that interfaces with a pin through the drive shaft coming out of the gear box 148. This arrangement prevents the worm drive 140 from imparting undue axial forces on the gear box 148 or gear motor 145 by allowing the worm drive 140 to move freely in an axial direction (away from the gear box 148), transferring those axial loads onto bushing 141 and the housing structure 150.

FIG. 3 illustrates generally a block diagram of components of a motorized lacing system 300, according to an example embodiment. The system 300 includes some, but not necessarily all, components of a motorized lacing system such as including interface buttons 301, a capacitive foot presence sensor 310, and the housing structure 150 enclosing a printed circuit board assembly (PCA) with a processor circuit 320, a battery 321, a charging coil 322, an encoder 325, a motion sensor 324, and a drive mechanism 340. The drive mechanism 340 can include, among other things, a motor 341, a transmission 342, and a lace spool 343. The motion sensor 324 can include, among other things, a single or multiple axis accelerometer, a magnetometer, a gyrometer, or other sensor or device configured to sense motion of the housing structure 150, or of one or more components within or coupled to the housing structure 150.

In the example of FIG. 3, the processor circuit 320 is in data or power signal communication with one or more of the interface buttons 301, foot presence sensor 310, battery 321, charging coil 322, and drive mechanism 340. The transmission 342 couples the motor 341 to the spool 343 to form the drive mechanism 340. In the example of FIG. 3, the buttons 301, foot presence sensor 310, and environment sensor 350 are shown outside of, or partially outside of, the housing structure 150.

In alternative embodiments, one or more of the buttons 301, foot presence sensor 310, and environment sensor 350 can be enclosed in the housing structure 150. In an example, the foot presence sensor 310 is disposed inside of the housing structure 150 to protect the sensor from perspiration and dirt or debris. Minimizing or eliminating connections through the walls of the housing structure 150 can help increase durability and reliability of the assembly.

In an example, the processor circuit 320 controls one or more aspects of the drive mechanism 340. For example, the processor circuit 320 can be configured to receive information from the buttons 301 and/or from the foot presence sensor 310 and/or from the motion sensor 324 and, in response, control the drive mechanism 340, such as to tighten or loosen footwear about a foot. In an example, the processor circuit 320 is additionally or alternatively configured to issue commands to obtain or record sensor information, from the foot presence sensor 310 or other sensor, among other functions. In an example, the processor circuit 320 conditions operation of the drive mechanism 340 on one or more of detecting a foot presence using the foot presence sensor 310, detecting a foot orientation or location using the foot presence sensor 310, or detecting a specified gesture using the motion sensor 324.

In an example, the system 300 includes an environment sensor 350. Information from the environment sensor 350 can be used to update or adjust a baseline or reference value for the foot presence sensor 310. As further explained below, capacitance values measured by a capacitive foot presence sensor can vary over time, such as in response to ambient conditions near the sensor. Using information from the environment sensor 350, the processor circuit 320 and/or the foot presence sensor 310 can therefore be configured to update or adjust a measured or sensed capacitance value.

FIG. 4 is a diagram illustrating pressure distribution data for a nominal or average foot (left) and for a high arch foot (right) in a footwear article 400 when a user of a footwear article is standing. In this example, it can be seen that the relatively greater areas of pressure underfoot include at a heel region 401, at a ball region 402 (e.g., between the arch and toes), and at a hallux region 403 (e.g., a "big toe" region). As discussed above, however, it can be advantageous to include various active components (e.g., including the foot presence sensor 310) in a centralized region, such as at or near an arch region. In an example, in the arch region, the housing structure 150 can be generally less noticeable or intrusive to a user when a footwear article that includes the housing structure 150 is worn.

In the example of FIG. 4, the lacing engine cavity 141 can be provided in an arch region. One or more electrodes corresponding to the foot presence sensor 310 can be positioned at or near a first location 405. Capacitance values measured using the electrodes positioned at the first location 405 can be different depending on the proximity of a foot relative to the first location 405. For example, different capacitance values would be obtained for the average foot and the high arch foot because a surface of the foot itself resides at a different distance from the first location 405. In an example, a location of the foot presence sensor 310 and/or the lacing engine 110 can be adjusted relative to footwear (e.g., by a user or by a technician at a point of sale), such as to accommodate different foot characteristics of different users and to enhance a signal quality obtained from the foot presence sensor 310. In an example, a sensitivity of the foot presence sensor 310 can be adjusted, such as by increasing a drive signal level or by changing a dielectric material positioned between the foot presence sensor 310 and the foot.

Figure 5A:
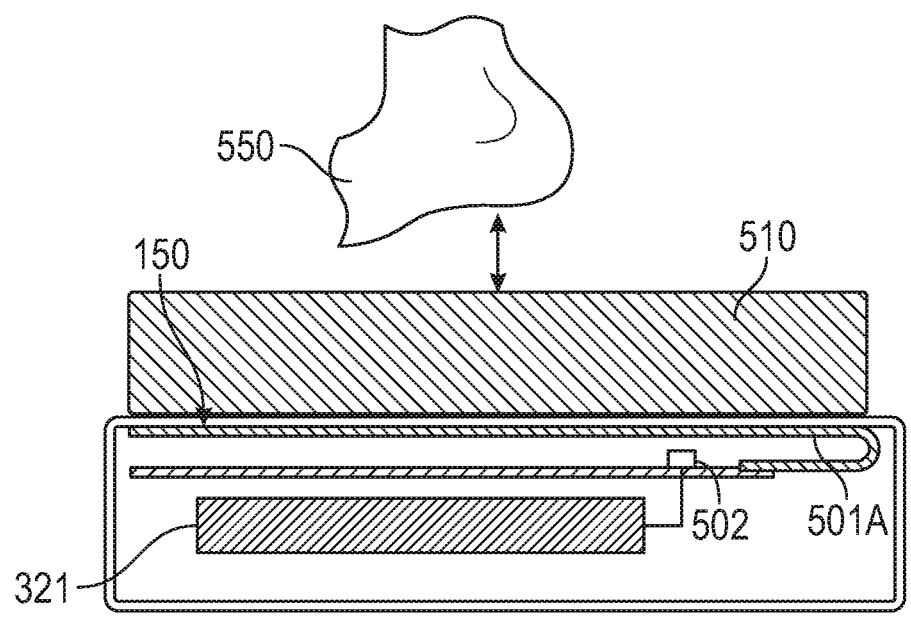
FIGS. 5A and 5B illustrate generally diagrams of a capacitance-based foot presence sensor in an insole of a footwear article, according to example embodiments.
Figure 5B:
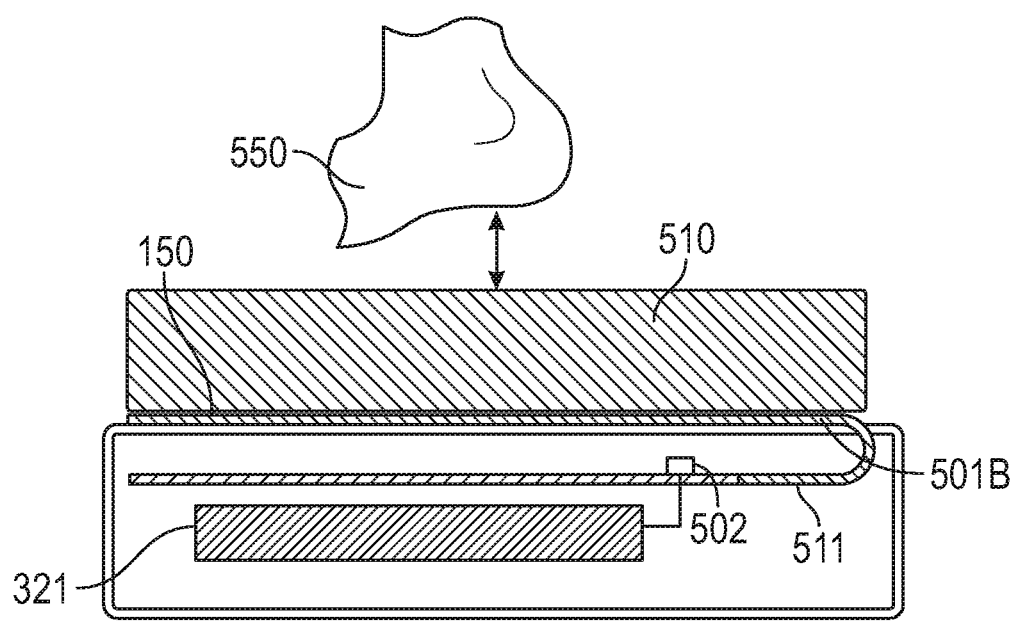

FIGS. 5A and 5B illustrate generally diagrams of a capacitance-based foot presence sensor in an insole of a footwear article, according to example embodiments. The capacitance-based foot presence sensor can be provided below a surface of an object or body 550, such as a foot, when the article incorporating the sensor is worn.

In FIG. 5A, the capacitance-based foot presence sensor can include a first electrode assembly 501A coupled to a capacitive sensing controller circuit 502. In an example, the controller circuit 502 is included in or includes functions performed by the processor circuit 320. In the example of FIG. 5A, the first electrode assembly 501A and/or the controller circuit 502 can be included in or mounted to an inner portion of the housing structure 150, or can be coupled to the PCA inside of the housing structure 150. In an example, the first electrode assembly 501A can be disposed at or adjacent to a foot-facing surface of the housing structure 150. In an example, the first electrode assembly 501A includes multiple traces distributed across an internal, upper surface region of the housing structure 150.

In FIG. 5B, the capacitance-based foot presence sensor can include a second electrode assembly 501B coupled to the capacitive sensing controller circuit 502. The second electrode assembly 501B can be mounted to or near an outer portion of the housing structure 150, and can be electrically coupled to the PCA inside of the housing structure 150, such as using a flexible connector 511. In an example, the second electrode assembly 501B can be disposed at or adjacent to a foot-facing surface of the housing structure 150. In an example, the second electrode assembly 501B includes a flexible circuit that is secured to an inner or outer surface of the housing structure 150, and coupled to the processor circuit 320 via one or more conductors.

In an example, the controller circuit 502 includes an Atmel ATSAML21E18B-MU, ST Microelectronics STM32L476M, or other similar device. The controller circuit 502 can be configured to, among other things, provide an AC drive signal to at least a pair of electrodes in the first or second electrode assembly 501A or 501B and, in response, sense changes in an electric field based on corresponding changes in proximity of the object or body 550 to the pair of electrodes, as explained in greater detail below. In an example, the controller circuit 502 includes or uses the foot presence sensor 310 or the processor circuit 320.

Various materials can be provided between the electrode assembly 501 and the object or body 550 to be sensed. For example, electrode insulation, a material of the housing structure 150, an insole material, an insert material 510, a sock or other foot cover, body tape, kinesiology tape, or other materials can be interposed between the body 550 and the electrode assembly 501, such as to change a dielectric characteristic of the footwear and thereby influence a capacitance detection sensitivity of a sensor that includes or uses the electrode assembly 501. The controller circuit 502 can be configured to update or adjust an excitation or sensing parameter based on the number or type of interposed materials, such as to enhance a sensitivity or signal-to-noise ratio of capacitance values sensed using the electrode assembly 501.

In the examples of FIGS. 5A/B, the first and/or second electrode assembly 501A and/or 501B can be excited by a signal generator in the controller circuit 502, and as a result an electric field can project from a top, foot-facing side of the electrode assembly. In an example, an electric field below the electrode assembly can be blocked at least in part using a driven shield positioned below the sensing electrode. The driven shield and electrode assembly can be electrically insulated from each other. For example, if the first electrode assembly 501A is on one surface of the PCA then the driven shield can be on the bottom layer of the PCA, or on any one of multiple inner layers on a multi-layer PCA. In an example, the driven shield can be of equal or greater surface area of the first electrode assembly 501A, and can be centered directly below the first electrode assembly 501A.

The driven shield can receive a drive signal and, in response, generate an electric field. The field generated by the driven shield can have substantially the same polarity, phase and/or amplitude of the field generated by the first electrode assembly 501A. The driven shield's field can repel the electric field of the first electrode assembly 501A, thereby isolating the sensor field from various parasitic effects, such as undesired coupling to a ground plane of the PCA. The field generated by the driven shield can help direct and focus detection to a particular area, can help reduce environmental effects, and can help reduce parasitic capacitance effects. In an example, including a driven shield and can help reduce effects of temperature variation on the sensor assembly. Temperature can influence a parasitic offset characteristic, and temperature changes, for example, can cause a parasitic ground plane capacitance to change. Using a shield, such as inserted between the sensor electrode and ground, can help mitigate an influence of a parasitic ground plane capacitance from sensor measurements.

A driven shield can be similarly provided for use with the second electrode assembly 501B. For example, the second electrode assembly 501B can be provided above or adjacent to the housing structure 150 as shown in the example of FIG. 5B. In an example, a portion of the housing structure 150 can include or can be covered in part with a conductive film that is used as a driven shield. Additionally or alternatively, the driven shield can be provided elsewhere in the footwear article when the second electrode assembly 501B is provided at a location other than atop or adjacent to the housing structure 150.

A preferred position in which to locate the housing structure 150 is in an arch area of footwear because it is an area less likely to be felt by a wearer and is less likely to cause discomfort to a wearer. One advantage of using capacitive sensing for detecting foot presence in footwear includes that a capacitive sensor can function well even when a capacitive sensor is placed in an arch region and a user has a relatively or unusually high foot arch. For example, a sensor drive signal amplitude or morphology characteristic can be changed or selected based on a detected signal-to-noise ratio of a signal received from a capacitive sensor. In an example, the sensor drive signal can be updated or adjusted each time footwear is used, such as to accommodate changes in one or more materials (e.g., socks, insoles, etc.) disposed between the first or second electrode assembly 501A or 501B and the body 550.

In an example, an electrode assembly of a capacitive sensor, such as the first or second electrode assembly 501A or 501B, can be configured to sense a difference in signals between multiple electrodes, such as between X and Y-axis oriented electrodes. In an example, a suitable sampling frequency can be between about 2 and 50 Hz. In some examples, capacitance-based foot sensing techniques can be relatively invariant to perspiration (wetness) on the insole or in a sock around a foot. The effect of such moisture can be to reduce a dynamic range of the detection since the presence of moisture can increase a measured capacitance. However, in some examples, the dynamic range is sufficient to accommodate this effect within expected levels of moisture in footwear.

Figure 6:
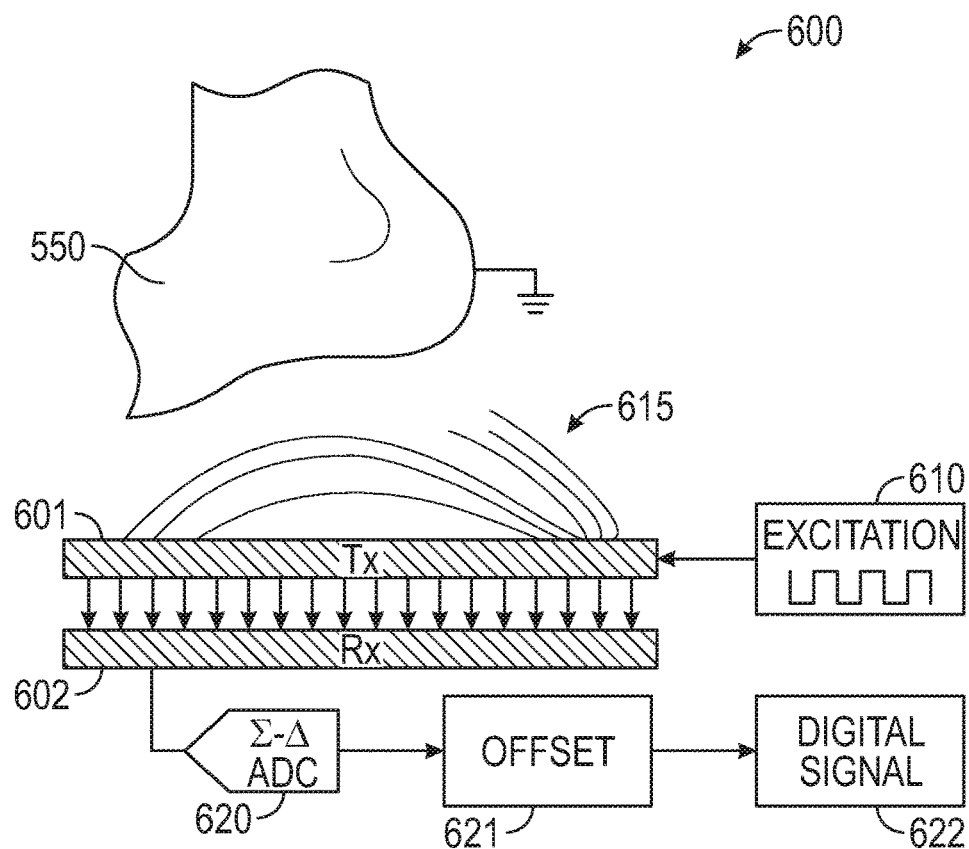
FIG. 6 illustrates generally a capacitive sensor system for foot presence detection, according to an example embodiment.

FIG. 6 illustrates generally a capacitive sensor system 600 for foot presence detection, according to an example embodiment. The system 600 includes the body 550 (e.g., representing a foot in or near an active footwear article) and first and second electrodes 601 and 602. The electrodes 601 and 602 can form all or a portion of the first or second electrode assembly 501A or 501B from the examples of FIGS. 5A/B, such as comprising a portion of the foot presence sensor 310. In the example of FIG. 6, the first and second electrodes 601 and 602 are illustrated as being vertically spaced relative to one another and the body 550, however, the electrodes can similarly be horizontally spaced, for example, as detailed in the example of FIGS. 7-9C. That is, in an example, the electrodes can be disposed in a plane that is parallel to a lower surface of the body 550. In the example of FIG. 6, the first electrode 601 is configured as a transmit electrode and is coupled to a signal generator 610. In an example, the signal generator 610 comprises a portion of the processor circuit 320 from the example of FIG. 3. That is, the processor circuit 320 can be configured to generate a drive signal and apply it to the first electrode 601.

As a result of exciting the first electrode 601 with a drive signal from the signal generator 610, an electric field 615 can be generated primarily between the first and second electrodes 601 and 602. That is, various components of the generated electric field 615 can extend between the first and second electrodes 601 and 602, and other fringe components of the generated electric field 615 can extend in other directions. For example, the fringe components can extend from the transmitter electrode or first electrode 601 away from the housing structure 150 (not pictured in the example of FIG. 6) and terminate back at the receiver electrode or second electrode 602.

Information about the electric field 615, including information about changes in the electric field 615 due to proximity of the body 550, can be sensed or received by the second electrode 602. Signals sensed from the second electrode 602 can be processed using various circuitry and used to provide an analog or digital signal indicative of presence or absence of the body 550.

For example, a field strength of the electric field 615 received by the second electrode 602 and measured using a sigma-delta analog-to-digital converter circuit (ADC) 620 that is configured to convert analog capacitance-indicating signals to digital signals. The electrical environment near the electrodes changes when an object, such as the body 550, invades the electric field 615, including its fringe components. When the body 550 enters the field, a portion of the electric field 615 is shunted to ground instead of being received and terminated at the second electrode 602 or passes through the body 550 (e.g., instead of through air) before being received at the second electrode 602. This can result in a capacitance change that can be detected by the foot presence sensor 310 and/or by the processor circuit 320.

In an example, the second electrode 602 can receive electric field information substantially continuously, and the information can be sampled continuously or periodically by the ADC 620. Information from the ADC 620 can be processed or updated according to an offset 621, and then a digital output signal 622 can be provided. In an example, the offset 621 is a capacitance offset that can be specified or programmed (e.g., internally to the processor circuit 320) or can be based on another capacitor used for tracking environmental changes over time, temperature, and other variable characteristics of an environment.

In an example, the digital output signal 622 can include binary information about a determined presence or absence of the body 550, such as by comparing a measured capacitance value to a specified threshold value. In an example, the digital output signal 622 includes qualitative information about a measured capacitance, such as can be used (e.g., by the processor circuit 320) to provide an indication of a likelihood that the body 550 is or is not present.

Periodically, or whenever the foot presence sensor 310 is not active (e.g., as determined using information from the motion sensor 324), a capacitance value can be measured and stored as a reference value, baseline value, or ambient value. When a foot or body approaches the foot presence sensor 310 and the first and second electrodes 601 and 602, the measured capacitance can decrease or increase, such as relative to the stored reference value. In an example, one or more threshold capacitance levels can be stored, e.g., in on-chip registers with the processor circuit 320. When a measured capacitance value exceeds a specified threshold, then the body 550 can be determined to be present (or absent) from footwear containing the foot presence sensor 310.

The foot presence sensor 310, and the electrodes 601 and 602 comprising a portion of the foot presence sensor 310, can take multiple different forms as illustrated in the several non-limiting examples that follow. In an example, the foot presence sensor 310 is configured to sense or use information about a mutual capacitance among or between multiple electrodes or plates.

In an example, the electrodes 601 and 602 are arranged in an electrode grid. A capacitive sensor that uses the grid can include a variable capacitor at each intersection of each row and each column of the grid. Optionally, the electrode grid includes electrodes arranged in one or multiple rows or columns. A voltage signal can be applied to the rows or columns, and a body or foot near the surface of the sensor can influence a local electric field and, in turn, can reduce a mutual capacitance effect. In an example, a capacitance change at multiple points on the grid can be measured to determine a body location, such as by measuring a voltage in each axis. In an example, mutual capacitance measuring techniques can provide information from multiple locations around the grid at the same time.

In an example, a mutual capacitance measurement uses an orthogonal grid of transmit and receive electrodes. In such a grid-based sensor system, measurements can be detected for each of multiple discrete X-Y coordinate pairs. In an example, capacitance information from multiple capacitors can be used to determine foot presence or foot orientation in footwear. In another example, capacitance information from one or more capacitors can be acquired over time and analyzed to determine a foot presence or foot orientation. In an example, rate of change information about X and/or Y detection coordinates can be used to determine when or if a foot is properly or completely seated with respect to an insole in footwear.

In an example, a self-capacitance based foot presence sensor can have the same X-Y grid as a mutual capacitance sensor, but the columns and rows can operate independently. In a self-capacitance sensor, capacitive loading of a body at each column or row can be detected independently.

Figure 7:
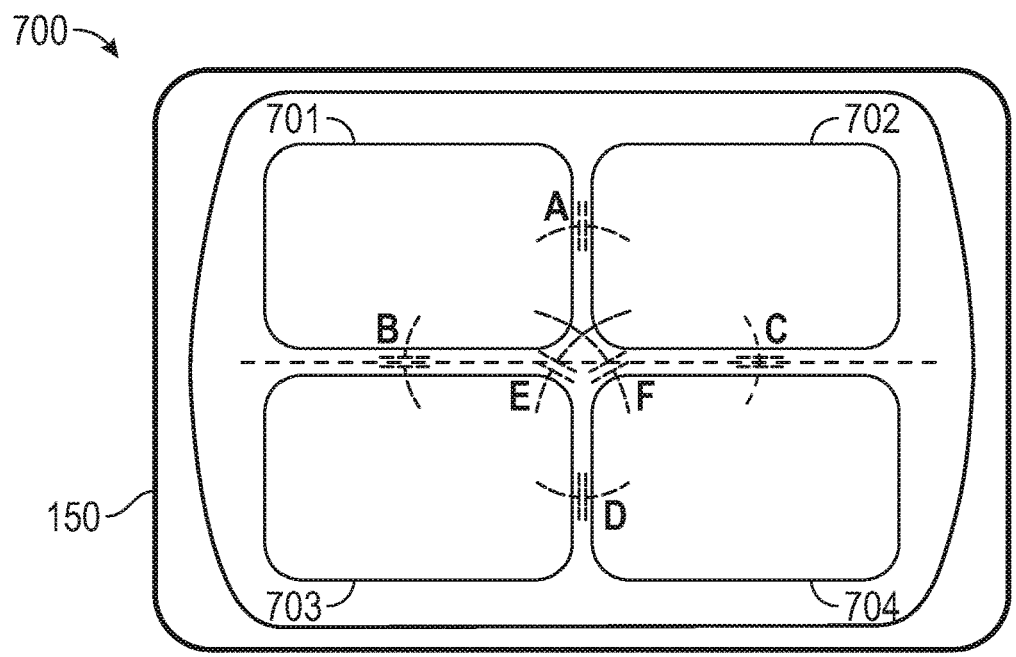
FIG. 7 illustrates generally a schematic of a first capacitance-based foot presence sensor, according to an example embodiment.

FIG. 7 illustrates generally a schematic of a first capacitance-based foot presence sensor, according to an example embodiment. In the example of FIG. 7, a first capacitive sensor 700 includes multiple parallel capacitive plates. The multiple plates can be arranged on or in the housing structure 150, for example, positioned at or near an underside of a foot when the footwear article including the first capacitive sensor 700 is worn. In an example, the capacitive foot presence sensor 310 includes or uses the first capacitive sensor 700.

In the example of FIG. 7, four conductive capacitor plates are illustrated as 701-704. The plates can be made of a conductive material such as a conductive foil. The foil can be flexible and can optionally be embedded into a plastic of the housing structure 150 itself, or can be independent of the housing structure 150. It is to be appreciated that any conductive material could be used, such as films, inks, deposited metals, or other materials. In the example of FIG. 7, the plates 701-704 are arranged in a common plane and are spaced apart from each other to form discrete conductive elements or electrodes.

A capacitance value of a capacitor is functionally related to a dielectric constant of a material between two plates that form a capacitor. Within the first capacitive sensor 700, a capacitor can be formed between each pair of two or more of the capacitor plates 701-704. Accordingly, there are six effective capacitors formed by the six unique combination pairs of the capacitor plates 701-704 as designated in FIG. 7 as capacitors A, B, C, D, E, and F. Optionally, two or more of the plates can be electrically coupled to form a single plate. That is, in an example, a capacitor can be formed using the first and second capacitor plates 701 and 702 electrically coupled to provide a first conductor, and the third and fourth capacitor plates 703 and 704 electrically coupled to provide a second conductor.

In an example, a capacitive effect between the first and second capacitor plates 701 and 702 is represented in FIG. 7 by a phantom capacitor identified by letter A. The capacitive effect between the first and third capacitor plates 701 and 703 is represented by the phantom capacitor identified by letter B. The capacitive effect between the second and fourth capacitor plates 702 and 704 is represented by the phantom capacitor identified by letter C, and so on. A person of ordinary skill in the art will appreciate that each phantom capacitor is representative of an electrostatic field extending between the respective pair of capacitor plates. Hereinafter, for the purpose of easy identification, the capacitor formed by each pair of capacitive plates is referred to by the letter (e.g., "A", "B", etc.) used in FIG. 7 to identify the phantom-drawn capacitors.

For each pair of capacitor plates in the example of FIG. 7, an effective dielectric between the plates includes an airgap (or other material) disposed between the plates. For each pair of capacitor plates, any portion of a body or foot that is proximal to the respective pair of capacitive plates can become part of, or can influence, an effective dielectric for the given pair of capacitive plates. That is, a variable dielectric can be provided between each pair of capacitor plates according to a proximity of a body to the respective pair of plates. For example, the closer a body or foot is to a given pair of plates, the greater the value of the effective dielectric may be. As the dielectric constant value increases, the capacitance value increases. Such a capacitance value change can be received by the processor circuit 320 and used to indicate whether a body is present at or near the first capacitive sensor 700.

In an example of the foot presence sensor 310 that includes the first capacitive sensor 700, a plurality of capacitive sensor drive/monitor circuits can be coupled to the plates 701-704. For example, a separate drive/monitor circuit can be associated with each pair of capacitor plates in the example of FIG. 7. In an example, drive/monitor circuits can provide drive signals (e.g., time-varying electrical excitation signals) to the capacitor plate pairs and, in response, can receive capacitance-indicating values. Each drive/monitor circuit can be configured to measure a variable capacitance value of an associated capacitor (e.g., the capacitor "A" corresponding to the first and second plates 701 and 702), and can be further configured to provide a signal indicative of the measured capacitance value. The drive/monitor circuits can have any suitable structure for measuring the capacitance. In an example, the two or more drive/monitor circuits can be used together, such as to provide an indication of a difference between capacitance values measured using different capacitors.

Figure 8:
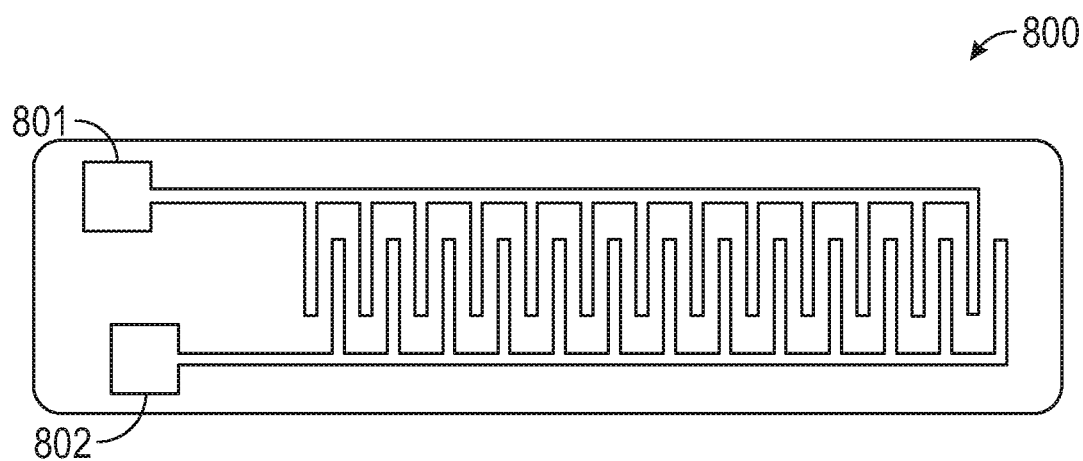
FIG. 8 illustrates generally a schematic of a second capacitance-based foot presence sensor, according to an example embodiment.

FIG. 8 illustrates generally a schematic of a second capacitance-based foot presence sensor, according to an example embodiment. The example of FIG. 8 includes a second capacitive sensor 800 that includes first and second electrodes 801 and 802. The foot presence sensor 310 can include or use the second capacitive sensor 800. In the example of FIG. 8, the first and second electrodes 801 and 802 are arranged along a substantially planar surface, such as in a comb configuration. In an example, a drive circuit, such as the processor circuit 320, can be configured to generate an excitation or stimulus signal to apply to the first and second electrodes 801 and 802. The same or different circuit can be configured to sense a response signal indicative of a change in capacitance between the first and second electrodes 801 and 802. The capacitance can be influenced by the presence of a body or foot relative to the electrodes. For example, the first and second electrodes 801 and 802 can be arranged on or near a surface of the housing structure 150, such as proximal to a foot when the foot is present within footwear that includes the housing structure 150.

In an example, the second capacitive sensor 800 includes an etched conductive layer, such as in an X-Y grid to form a pattern of electrodes. Additionally or alternatively, the electrodes of the second capacitive sensor 800 can be provided by etching multiple separate, parallel layers of conductive material, for example with perpendicular lines or tracks to form a grid. In this and other capacitive sensors, no direct contact between a body or foot and a conductive layer or electrode is needed. For example, the conductive layer or electrode can be embedded in the housing structure 150, or can be coated with a protective or insulating layer. Instead, the body or foot to be detected can interface with or influence an electric field characteristic near the electrodes, and changes in the electric field can be detected.

In an example, separate capacitance values can be measured for the first electrode 801 with respect to ground or to a reference, and for the second electrode 802 with respect to ground or to a reference. A signal for use in foot presence detection can be based on a difference between the separate capacitance values measured for the first and second electrodes 801 and 802. That is, the foot presence or foot detection signal can be based on a difference between discrete capacitance signals that are measured using the first and second electrodes 801 and 802.

Figure 9A:
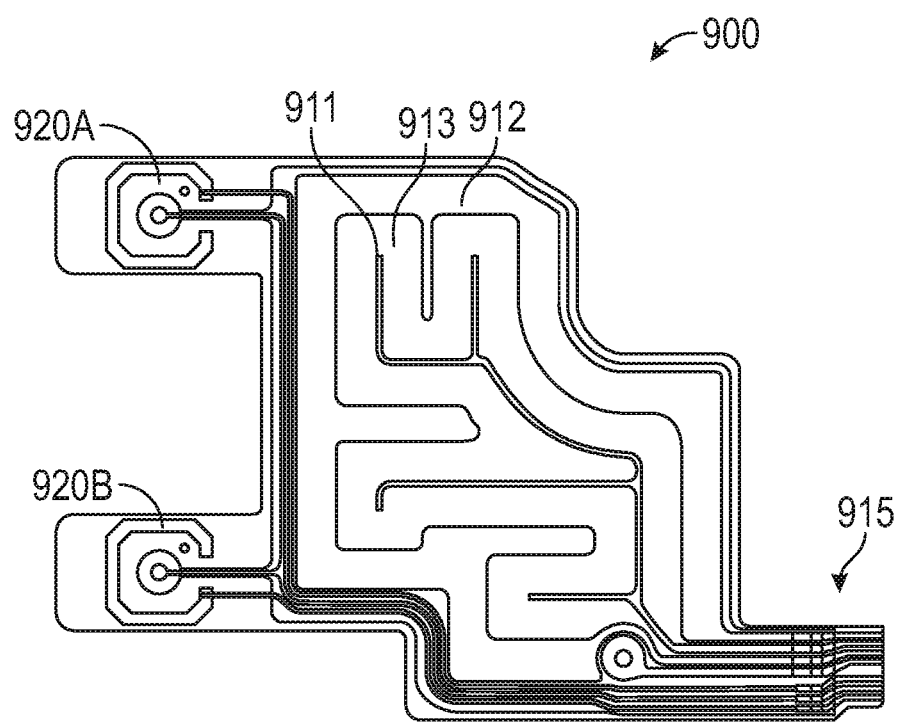
FIGS. 9A, 9B, and 9C illustrate generally examples of capacitance-based foot presence sensor electrodes, according to some example embodiments.
Figure 9B:
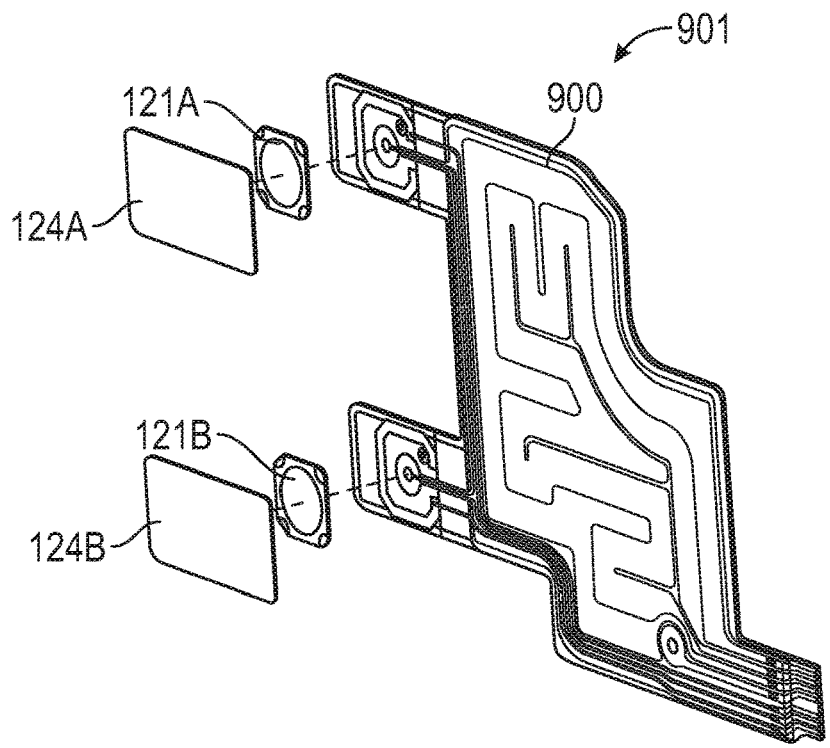
Figure 9C:
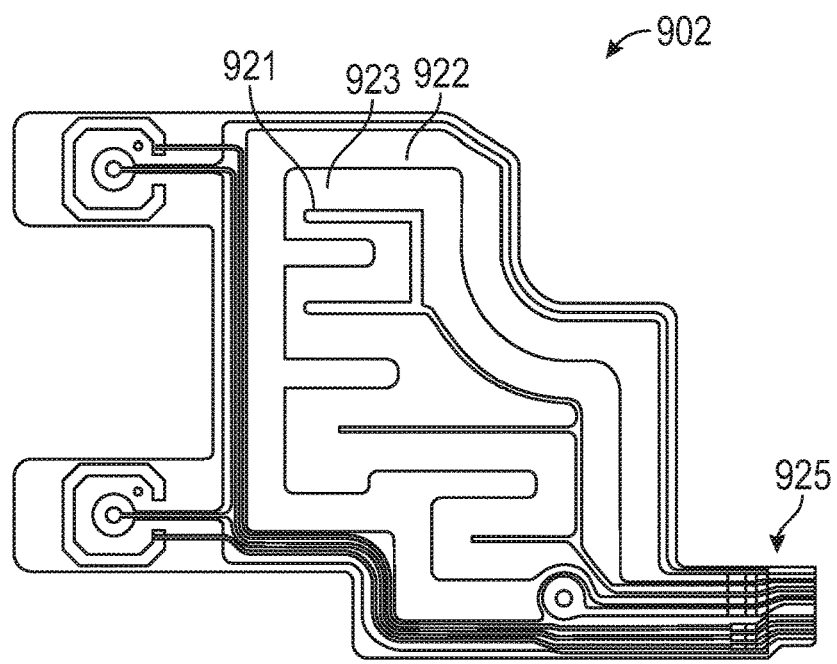

FIGS. 9A and 9B illustrate generally examples of a third capacitive sensor 900, according to some examples. FIG. 9C illustrates generally an example of a fourth capacitive sensor 902. FIG. 9A shows a schematic top view of the third capacitive sensor 900. FIG. 9B shows a perspective view of a sensor assembly 901 that includes the third capacitive sensor 900. FIG. 9C shows a schematic top view of the fourth capacitive sensor 902.

In the example of FIG. 9A, the third capacitive sensor 900 includes an electrode region with a first electrode trace 911 and a second electrode trace 912. The first and second electrode traces 911 and 912 are separated by an insulator trace 913. In an example, the first and second electrode traces 911 and 912 can be copper, carbon, or silver, among other conductive materials, and can be disposed on a substrate made from FR4, Polyimide, PET, among other materials. The substrate and traces of the third capacitive sensor 900 can include one or more flexible portions.

The first and second electrode traces 911 and 912 can be distributed substantially across a surface area of a substrate of the third capacitive sensor 900. The electrode traces can be positioned against an upper or top surface of the housing structure 150 when the third capacitive sensor 900 is installed. In an example, one or both of the first and second electrode traces 911 and 912 can be about 2 mm wide. The insulator trace 913 can be about the same width. In an example, the trace widths can be selected based on, among other things, a footwear size or an insole type. For example, different trace widths can be selected for the first and second electrode traces 911 and 912 and/or for the insulator trace 913 depending on, e.g., a distance between the traces and the body to be sensed, an insole material, a gap filler, housing structure 150 material, or other materials used in the footwear, such as to maximize a signal-to-noise ratio of capacitance values measured using the third capacitive sensor 900.

The third capacitive sensor 900 can include a connector 915. The connector 915 can be coupled with a mating connector, such as coupled to the PCA in the housing structure 150. The mating connector can include one or more conductors to electrically couple the first and second electrode traces 911 and 912 with the processor circuit 320.

In an example, the third capacitive sensor 900 includes input signal conductors 920A and 920B. The input signal conductors 920A and 920B can be configured to be coupled with one or more input devices, such as dome buttons or other switches, such as corresponding to the buttons 121 in the example of FIG. 2A.

FIG. 9B illustrates the sensor assembly 901, including the third capacitive sensor 900, the buttons 121A and 121B, and membrane seals 124A and 124B. In an example, corresponding conductive surfaces of the input signal conductors 920A and 920B couple with buttons 121A and 121B. The membrane seals 124A and 124B are adhered over the buttons 121A and 121B, such as to protect the buttons 121A and 121B from debris and retain them in alignment with the conductor surfaces.

In the example of FIG. 9C, the fourth capacitive sensor 902 includes an electrode region with a first electrode trace 921 and a second electrode trace 922. The first and second electrode traces 921 and 922 are separated by an insulator trace 923. The electrode traces can comprise various conductive materials, and the fourth capacitive sensor 902 can include one or more flexible portions. The fourth capacitive sensor 902 can include a connector 925, and can be coupled with a mating connector, such as coupled to the PCA in the housing structure 150.

The present inventors have recognized that a problem to be solved includes obtaining a suitable sensitivity of or response from a capacitive foot presence sensor, for example, when all or a portion of the foot presence sensor is spaced apart from a foot or body to be detected, such as by an air gap or other intervening material. The present inventors have recognized that a solution can include using multiple electrodes of specified shapes, sizes, and orientations to enhance an orientation and relative strength of an electric field that is produced when the electrodes are energized. That is, the present inventors have identified an optimal electrode configuration for use in capacitive foot presence sensing.

In an example, multiple electrodes of the fourth capacitive sensor 902 include the first and second electrode traces 921 and 922, and each of the first and second electrode traces 921 and 922 includes multiple discrete fingers or traces that extend substantially parallel to one another. For example, the first and second electrode traces 921 and 922 can include multiple interleaved conductive finger portions, as shown in FIG. 9C.

In an example, the second electrode trace 922 can include a shoreline or perimeter portion that extends substantially about the outer perimeter edge or surface portion of the fourth capacitive sensor 902, and substantially surrounds the first electrode trace 921. In the example of FIG. 9C, the shoreline that includes the second electrode trace 922 extends around substantially all of the top surface of the fourth capacitive sensor 902 assembly, however, the shoreline can extend about a lesser portion of the sensor in some other examples. The present inventors have further recognized that an optimal electric field for detecting foot presence is generated when most or all of the fingers of first and second electrode traces 921 and 922 are arranged substantially parallel to one another, such as instead of including one or more traces or finger portions that are non-parallel. For example, in contrast with the fourth capacitive sensor 902, the third capacitive sensor 900 of FIG. 9A includes non-parallel fingers, such as at an upper portion of the first electrode trace 911 that includes vertically extending finger portions and at a lower portion of the first electrode trace 911 that includes horizontally extending finger portions. The relative thickness of the first and second electrode traces 921 and 922 can be adjusted to further enhance sensitivity of the sensor. In an example, the second electrode trace 922 is three or more times thicker than the first electrode trace 921.

In an example, capacitance values measured by the foot presence sensor 310, such as using one or more of the first, second, third, and fourth capacitive sensors 700, 800, 900, and 902, can be provided to a controller or processor circuit, such as the processor circuit 320 of FIG. 3. In response to the measured capacitance, the processor circuit 320 can actuate the drive mechanism 340, such as to adjust a footwear tension about a foot. The adjusting operation can optionally be performed at least in part by discrete, "hard-wired" components, can be performed by a processor executing software, or can be performed be a combination of hard-wired components and software. In an example, actuating the drive mechanism 340 includes (1) monitoring signals from the foot presence sensor 310 using one or more drive/monitor circuits, such as using the processor circuit 320, (2) determining which, if any, of received capacitance signals indicate a capacitance value that meets or exceeds a specified threshold value (e.g., stored in memory registers of the processor circuit 320 and/or in a memory circuit in data communication with the processor circuit 320), (3) characterizing a location, size, orientation, or other characteristic of a body or foot near the foot presence sensor 310, such as based upon various specified threshold values that are exceeded, and (4) permitting, enabling, adjusting, or suppressing actuation of the drive mechanism 340 depending upon the characterization.

Figure 10:
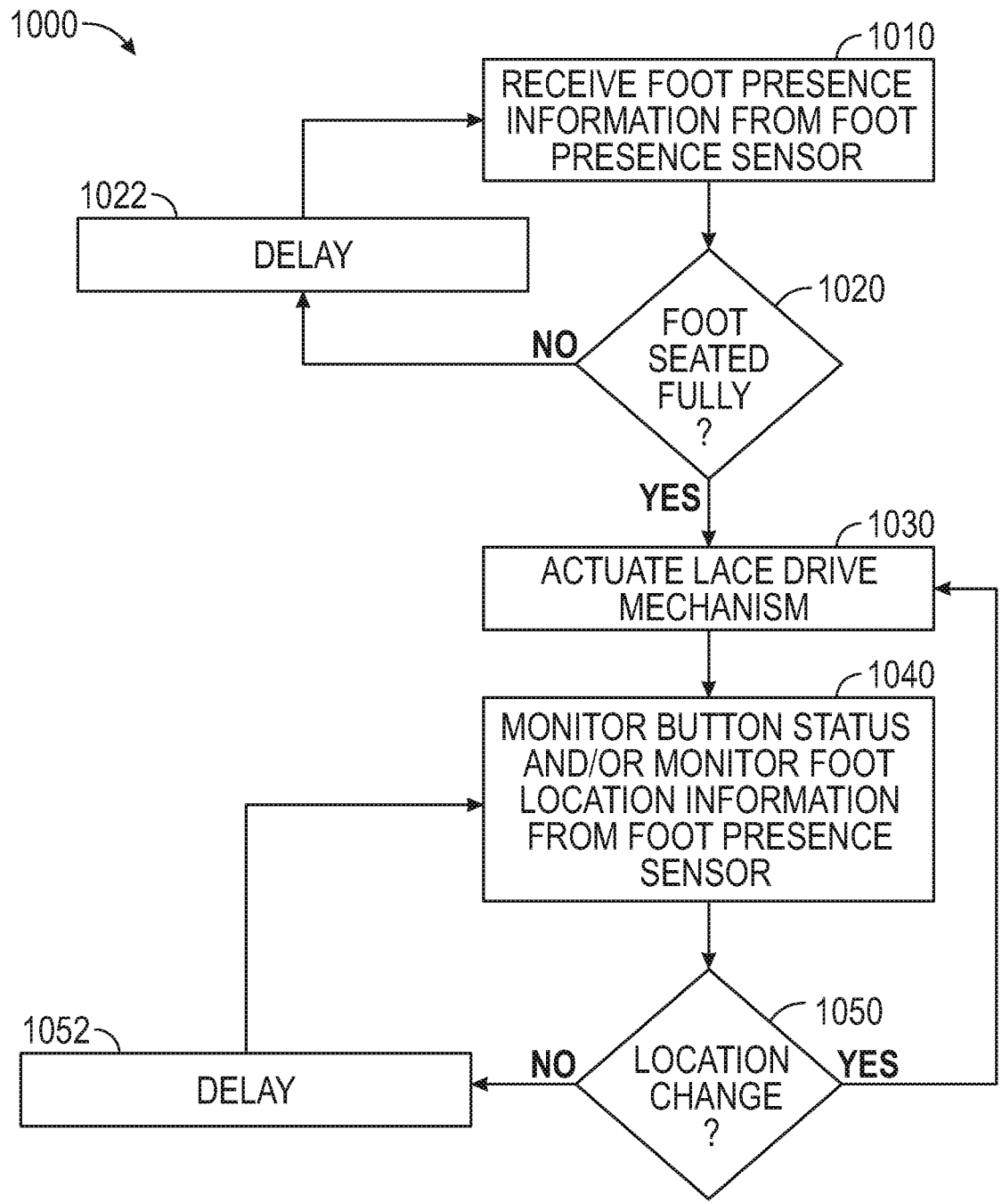
FIG. 10 illustrates a flowchart showing an example of using foot presence information from a footwear sensor.

FIG. 10 illustrates a flowchart showing an example of a method 1000 that includes using foot presence information from a footwear sensor. At operation 1010, the example includes receiving foot presence information from the foot presence sensor 310. The foot presence information can include binary information about whether or not a foot is present in footwear (see, e.g., the interrupt signals discussed in the examples of FIGS. 12-14), or can include an indication of a likelihood that a foot is present in a footwear article. The information can include an electrical signal provided from the foot presence sensor 310 to the processor circuit 320. In an example, the foot presence information includes qualitative information about a location of a foot relative to one or more sensors in the footwear.

At operation 1020, the example includes determining whether a foot is fully seated in the footwear. If the sensor signal indicates that the foot is fully seated, then the example can continue at operation 1030 with actuating the drive mechanism 340. For example, when a foot is determined to be fully seated at operation 1020, such as based on information from the foot presence sensor 310, the drive mechanism 340 can be engaged to tighten footwear laces via the spool 131, as described above. If the sensor signal indicates that the foot is not fully seated, then the example can continue at operation 1022 by delaying or idling for some specified interval (e.g., 1-2 seconds, or more). After the specified delay elapses, the example can return to operation 1010, and the processor circuit can re-sample information from the foot presence sensor 310 to determine again whether the foot is fully seated.

After the drive mechanism 340 is actuated at operation 1030, the processor circuit 320 can be configured to monitor foot location information at operation 1040. For example, the processor circuit can be configured to periodically or intermittently monitor information from the foot presence sensor 310 about an absolute or relative position of a foot in the footwear. In an example, monitoring foot location information at operation 1040 and receiving foot presence information at operation 1010 can include receiving information from the same or different foot presence sensor 310. For example, different electrodes can be used to monitor foot presence or position information at operations 1010 and 1040.

At operation 1040, the example includes monitoring information from one or more buttons associated with the footwear, such as the buttons 121. Based on information from the buttons 121, the drive mechanism 340 can be instructed to disengage or loosen laces, such as when a user wishes to remove the footwear.

In an example, lace tension information can be additionally or alternatively monitored or used as feedback information for actuating the drive mechanism 340, or for tensioning laces. For example, lace tension information can be monitored by measuring a drive current supplied to the motor 341. The tension can be characterized at a point of manufacture or can be preset or adjusted by a user, and can be correlated to a monitored or measured drive current level.

At operation 1050, the example includes determining whether a foot location has changed in the footwear. If no change in foot location is detected by the foot presence sensor 310 and the processor circuit 320, then the example can continue with a delay at operation 1052. After a specified delay interval at operation 1052, the example can return to operation 1040 to re-sample information from the foot presence sensor 310 to again determine whether a foot position has changed. The delay at operation 1052 can be in the range of about a millisecond to several seconds, and can optionally be specified by a user.

In an example, the delay at operation 1052 can be determined automatically by the processor circuit 320, such as in response to determining a footwear use characteristic. For example, if the processor circuit 320 determines that a wearer is engaged in strenuous activity (e.g., running, jumping, etc.), then the processor circuit 320 can decrease a delay duration provided at operation 1052. If the processor circuit determines that the wearer is engaged in non-strenuous activity (e.g., walking or sitting), then the processor circuit can increase the delay duration provided at operation 1052. By increasing a delay duration, battery life can be preserved by deferring sensor sampling events and corresponding consumption of power by the processor circuit 320 and/or by the foot presence sensor 310. In an example, if a location change is detected at operation 1050, then the example can continue by returning to operation 1030, for example, to actuate the drive mechanism 340 to tighten or loosen the footwear about the foot. In an example, the processor circuit 320 includes or incorporates a hysteretic controller for the drive mechanism 340 to help avoid unwanted lace spooling in the event of, e.g., minor detected changes in foot position.

Figure 11:
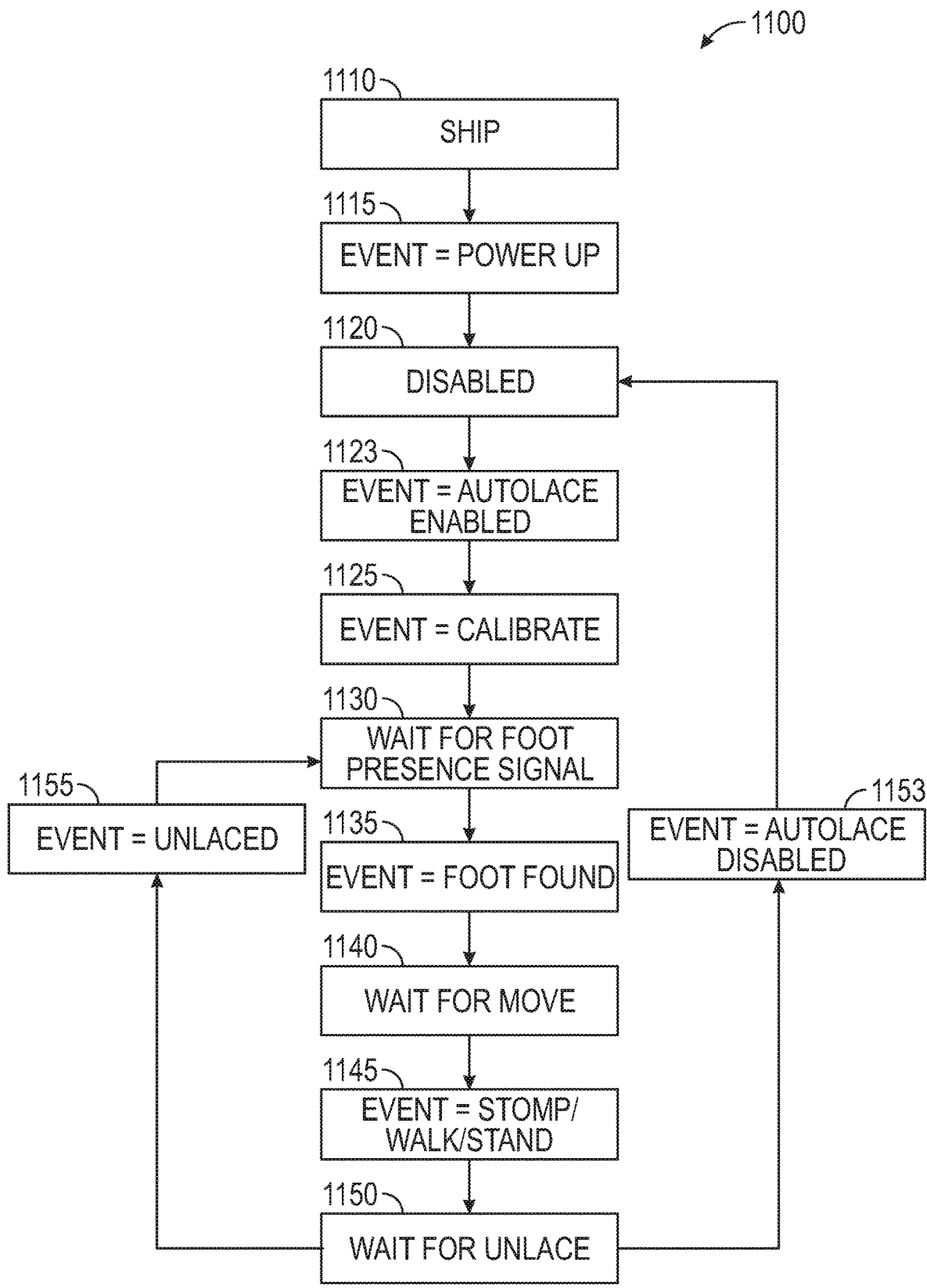
FIG. 11 illustrates a flowchart showing a second example of using foot presence information from a footwear sensor.

FIG. 11 illustrates a flowchart showing an example of a method 1100 of using foot presence information from a footwear sensor. The example of FIG. 11 can, in an example, refer to operations of a state machine, such as can be implemented using the processor circuit 320 and the foot presence sensor 310.

State 1110 can include a "Ship" state that represents a default or baseline state for an active footwear article, the article including one or more features that can be influenced by information from the foot presence sensor 310. In the Ship state 1110, various active components of the footwear can be switched off or deactivated to preserve the footwear's battery life.

In response to a "Power Up" event 1115, the example can transition to a "Disabled" or inactive state 1120. The drive mechanism 340, or other features of the active footwear, can remain on standby in the Disabled state 1120. Various inputs can be used as triggering events to exit the Disabled state 1120. For example, a user input from one of the buttons 121 can be used to indicate a transition out of the Disabled state 1120. In an example, information from the motion sensor 324 can be used as a wake-up signal. Information from the motion sensor 324 can include information about movement of the footwear, such as can correspond to a user placing the shoes in a ready position, or a user beginning to insert a foot into the footwear.

The state machine can remain in the Disabled state 1120 following the Power Up event 1115 until an Autolace enabled event 1123 is encountered or received. The Autolace enabled event 1123 can be triggered manually by a user (e.g., using a user input or interface device to the drive mechanism 340), or can be triggered automatically in response to, e.g., gesture information received from the motion sensor 324. Following the Autolace enabled event 1123, a Calibrate event 1125 can occur. The Calibrate event 1125 can include setting a reference or baseline value for a capacitance of the foot presence sensor 310, such as to account for environmental effects on the sensor. The calibration can be performed based on information sensed from the foot presence sensor 310 itself or can be based on programmed or specified reference information. The calibration can be postponed, for example, if a calibration result is outside of a specified range or if environmental effects are excessive.

Following the Autolace enabled event 1123, the state machine can enter a holding state 1130 to "Wait for foot presence signal". At state 1130, the state machine can wait for an interrupt signal from the foot presence sensor 310 and/or from the motion sensor 324. Upon receipt of the interrupt signal, such as indicating a foot is present, or indicating a sufficient likelihood that a foot is present, an event register can indicate "Foot found" at event 1135.

The state machine can transition to or initiate various functions when a Foot found event 1135 occurs. For example, the footwear can be configured to tighten or adjust a tension characteristic using the drive mechanism 340 in response to the Foot found event 1135. In an example, the processor circuit 320 actuates the drive mechanism 340 to a adjust lace tension by an initial amount in response to the Foot found event 1135, and the processor circuit 320 delays further tensioning the footwear unless or until a further control gesture is detected or user input is received. That is, the state machine can transition to a "Wait for move" state 1140. In an example, the processor circuit 320 enables the drive mechanism 340 but does not actuate the drive mechanism following the Foot found event 1135. At state 1140, the state machine can hold or pause for additional sensed footwear motion information before initiating any initial or further tension adjustment. Following the Wait for move state 1140, a Stomp/Walk/Stand event 1145 can be detected and, in response, the processor circuit 320 can further adjust a tension characteristic for the footwear.

The Stomp/Walk/Stand event 1145 can include various discrete, sensed inputs, such as from one or more sensors in the active footwear. For example, a Stomp event can include information from the motion sensor 324 that indicates an affirmative acceleration (e.g., in a specified or generic direction) and an "up" or "upright" orientation. In an example, a Stomp event includes a "high knee" or kick type event where a user raises one knee substantially vertically and forward. An acceleration characteristic from the motion sensor 324 can be analyzed, such as to determine whether the acceleration meets or exceeds a specified threshold. For example, a slow knee-raise event may not trigger a Stomp event response, whereas a rapid or quick knee-raise event may trigger a Stomp event response.

A Walk event can include information from the motion sensor 324 that indicates an affirmative step pattern and an "up" or "upright" orientation. In an example, the motion sensor 324 and/or the processor circuit 320 is configured to identify a step event, and the Walk event can be recognized when the step event is identified and when an accelerometer (e.g., included with or separate from the motion sensor 324) indicates that the footwear is upright.

A Stand event can include information from the motion sensor that indicates an "up" or "upright" orientation, such as without further information about an acceleration or direction change of the footwear from the motion sensor. In an example, the Stand event can be discerned using information about a change in a capacitance signal from the capacitive foot presence sensor 310, such as further described below. That is, a capacitance signal from the foot presence sensor 310 can include signal variations that can indicate whether a user is standing, such as when the user's foot applies downward pressure on the footwear.

The specific examples of the Stomp/Walk/Stand event 1145 are not to be considered limiting and various other gestures, time-based inputs, or user-input controls can be provided to further control or influence behavior of the footwear, such as after a foot is detected at the Foot found event 1135.

Following the Stomp/Walk/Stand event 1145, the state machine can include a "Wait for unlace" state 1150. The Wait for unlace state 1150 can include monitoring user inputs and/or gesture information (e.g., using the motion sensor 324) for instructions to relax, de-tension, or unlace the footwear. In the Wait for unlace state 1150, a state manager such as the processor circuit 320 can indicate that the lacing engine or drive mechanism 340 is unlaced and should return to the Wait for foot presence signal state 1130. That is, in a first example, an Unlaced event 1155 can occur (e.g., in response to a user input), the state machine can transition the footwear to an unlaced state, and the state machine can return to the Wait for foot presence signal state 1130. In a second example, an Autolace disabled event 1153 can occur and transition the footwear to the Disabled state 1120.

Figure 12:
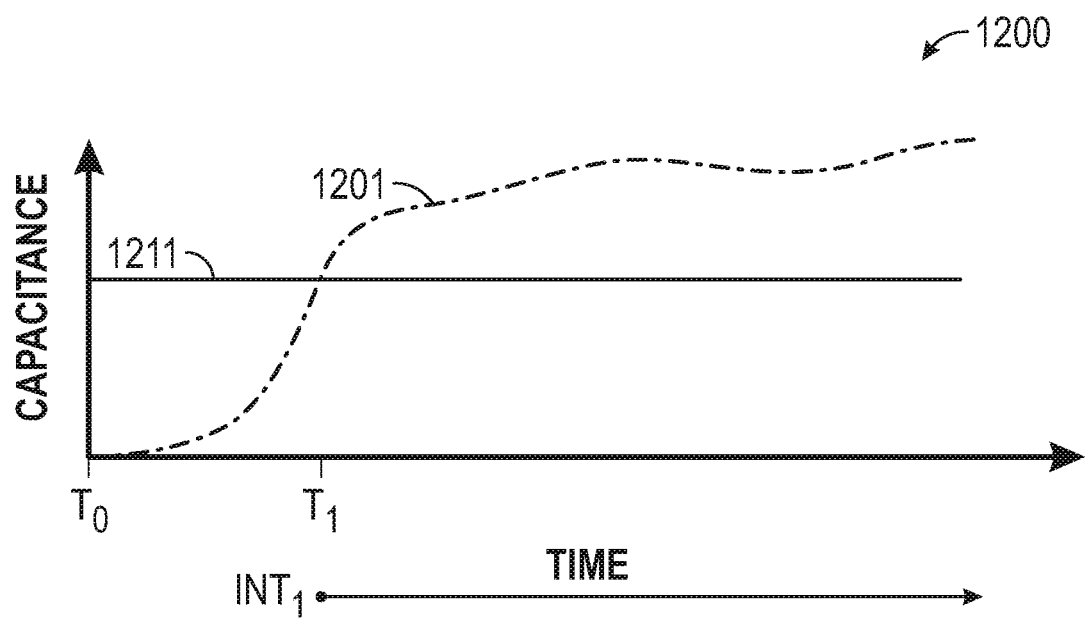
FIG. 12 illustrates generally a chart of first time-varying information from a capacitive foot presence sensor.

FIG. 12 illustrates generally a chart 1200 of first time-varying information from a capacitive foot presence sensor. The example of FIG. 12 includes a capacitance vs. time chart and a first time-varying capacitance signal 1201 plotted on the chart. In an example, the first time-varying capacitance signal 1201 can be obtained using the foot presence sensor 310 described herein. The first time-varying capacitance signal 1201 can correspond to a measured capacitance, or an indication of an influence of a body on an electric field, between multiple electrodes in the foot presence sensor 310, as described above. In an example, the first time-varying capacitance signal 1201 represents an absolute or relative capacitance signal value, and in another example, the signal represents a difference between the signal value and a reference capacitance signal value.

In an example, the first capacitance signal 1201 can be compared with a specified first threshold capacitance value 1211. The foot presence sensor 310 can be configured to perform the comparison, or the processor circuit 320 can be configured to receive capacitance information from the foot presence sensor 310 and perform the comparison. In the example of FIG. 12, the first threshold capacitance value 1211 is indicated to be a constant non-zero value. When the first capacitance signal 1201 meets or exceeds the first threshold capacitance value 1211, such as at time $T_1$, the foot presence sensor 310 and/or the processor circuit 320 can provide a first interrupt signal $INT_1$. The first interrupt signal $INT_1$ can remain high as long as the capacitance value indicated by the foot presence sensor 310 meets or exceeds the first threshold capacitance value 1211.

In an example, the first interrupt signal $INT_1$ can be used in the example of FIG. 10, such as at operations 1010 or 1020. At operation 1010, receiving foot presence information from the foot presence sensor 310 can include receiving the first interrupt signal $INT_1$, such as at the processor circuit 320. In an example, operation 1020 can include using interrupt signal information to determine whether a foot is, or is likely to be, fully seated in footwear. For example, the processor circuit 320 can monitor a duration of the first interrupt signal $INT_1$ to determine how long the foot presence sensor 310 provides a capacitance value that exceeds the first threshold capacitance value 1211. If the duration exceeds a specified reference duration, then the processor circuit 320 can determine that a foot is, or is likely to be, fully seated.

In an example, the first interrupt signal $INT_1$ can be used in the example of FIG. 11, such as at state 1130 or event 1135. At state 1130, the state machine can be configured to wait for an interrupt signal, such as $INT_1$, from the processor circuit 320 or from the foot presence sensor 310. At event 1135, the state machine can receive the first interrupt signal $INT_1$ and, in response, one or more following states can be initiated.

In an example, the first threshold capacitance value 1211 is adjustable. The threshold can change based on measured or detected changes in a capacitance baseline or reference, such as due to environment changes. In an example, the first threshold capacitance value 1211 can be specified by a user. The user's specification of the threshold value can influence a sensitivity of the footwear. In an example, the first threshold capacitance value 1211 can be adjusted automatically in response to sensed environment or material changes in or around the foot presence sensor 310.

Figure 13:
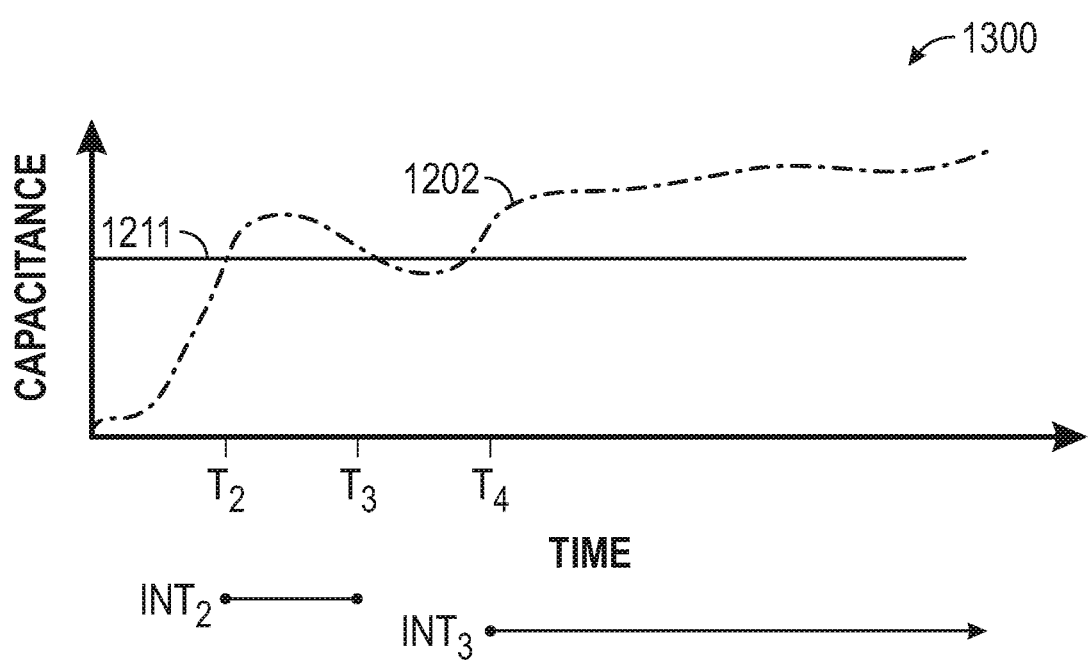
FIG. 13 illustrates generally a chart of second time-varying information from a capacitive foot presence sensor.

FIG. 13 illustrates generally a chart 1300 of second time-varying information from a capacitive foot presence sensor. The example of FIG. 13 shows how fluctuations of a second capacitance signal 1202 near the first threshold capacitance value 1211 can be handled or used to determine more information about a foot presence or orientation in footwear.

In an example, the second capacitance signal 1202 is received from the foot presence sensor 310, and the second capacitance signal 1202 is compared with the first threshold capacitance value 1211. Other threshold values can similarly be used depending on, among other things, a user, a user preference, a footwear type, or an environment or environment characteristic. In the example of FIG. 13, the second capacitance signal 1202 can cross the first threshold capacitance value 1211 at times $T_2$, $T_3$, and $T_4$. In an example, the multiple threshold crossings can be used to positively identify a foot presence by the foot presence sensor 310, such as by indicating a travel path for a foot as it enters the footwear. For example, the time interval bounded by the first and second threshold crossings at times $T_2$ and $T_3$ can indicate a duration when a foot's toes or phalanges are positioned at or near electrodes of the foot presence sensor 310. The interval between $T_3$ and $T_4$, when the sensed capacitance is less than the first threshold capacitance value 1211, can correspond to a time when the foot's metatarsal joints or metatarsal bones travel over or near the electrodes of the foot presence sensor 310. The metatarsal joints and bones can be spaced away from the foot presence sensor 310 by a distance that is greater than a distance of the phalanges to the foot presence sensor 310 when the phalanges travel into the footwear, and therefore the resulting measured capacitance between $T_3$ and $T_4$ can be less. At time $T_4$, the heel or talus of the foot can slide into position and the arch can become seated over electrodes of the foot presence sensor 310, thereby bringing a sensed capacitance back up and exceeding the first threshold capacitance value 1211. Accordingly, the foot presence sensor 310 or the processor circuit 320 can be configured to render a second interrupt signal $INT_2$ between times $T_2$ and $T_3$, and to render a third interrupt signal $INT_3$ following time $T_4$.

In an example, the processor circuit 320 can be configured to positively identify a foot presence based on a sequence of interrupt signals. For example, the processor circuit 320 can use information about received interrupt signals and about one or more intervals or durations between the received interrupt signals. For example, the processor circuit can be configured to look for a pair of interrupt signals separated by a specified duration to provide a positive indication of a foot presence. In FIG. 13, for example, a duration between $T_3$ and $T_4$ can be used to provide an indication of a foot presence, such as with some adjustable or specified margin of error. In an example, the processor circuit 320 can receive interrupt signals as data and process the data together with other user input signals, for example as part of a gesture-based user input. In an example, information about a presence or absence of an interrupt signal can be used to validate or dismiss one or more other signals. For example, an accelerometer signal can be validated and processed by the processor circuit 320 when an interrupt signal is or was recently received, or the accelerometer signal can be dismissed by the processor circuit 320 when an interrupt signal corresponding to the foot presence sensor is absent.

The examples of FIG. 12 and FIG. 13 show embodiments wherein measured capacitance values from the foot presence sensor 310 are reliably constant or reproducible over time, including in the presence of changes in environmental conditions. In many footwear use cases, however, ambient capacitance changes in embedded electronics can occur constantly or unpredictably, such as due to changes in temperature, humidity, or other environmental factors. Significant changes in ambient capacitance can adversely affect activation of the foot presence sensor 310, such as by changing a baseline or reference capacitance characteristic of the sensor.

Figure 14:
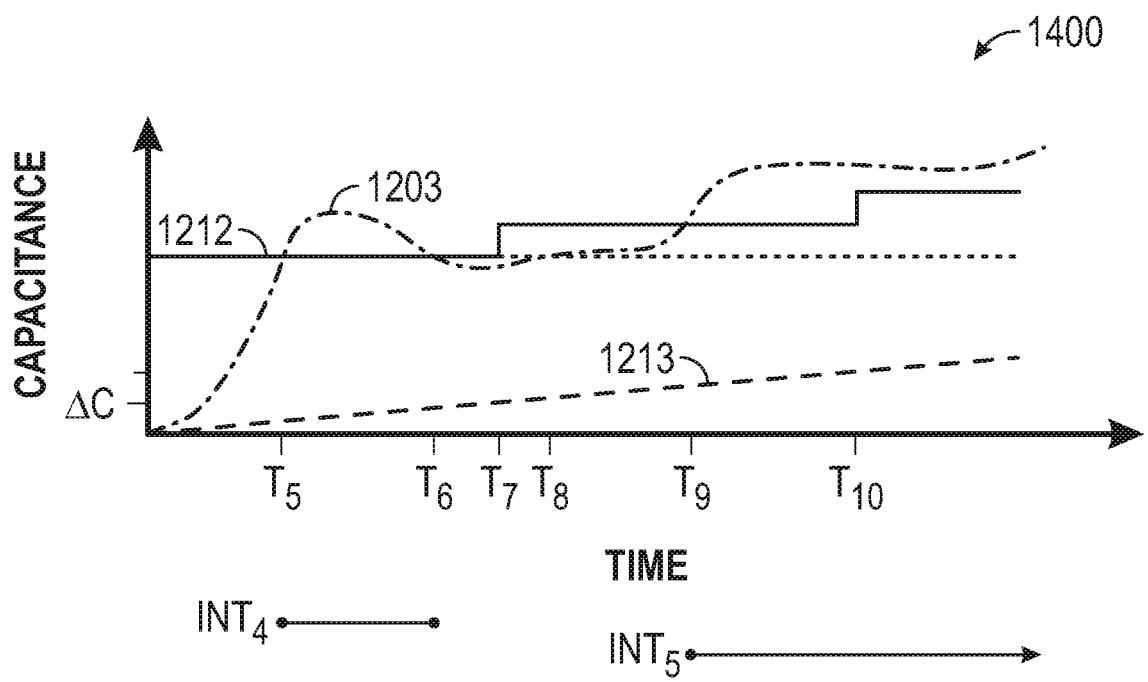
FIG. 14 illustrates generally a chart of third time-varying information from a capacitive foot presence sensor.

FIG. 14 illustrates generally a chart 1400 of third time-varying information from a capacitive foot presence sensor. The example of FIG. 14 shows how reference capacitance changes, such as due to changes in various ambient conditions, changes in use scenarios, or changes due to wear and tear or degradation of footwear components, can be accounted for. The example includes a third capacitance signal 1203 plotted on the chart 1400 with a second threshold capacitance 1212 and a time-varying reference capacitance 1213. In the example of FIG. 14, the time-varying reference capacitance 1213 increases over time. In other examples, a reference capacitance can decrease over time, or can fluctuate, such as over the course of a footwear usage event (e.g., over the course of one day, one game played, one user's settings or preferences, etc.). In an example, a reference capacitance can change over a life cycle of various components of the footwear itself, such as an insole, outsole, sock liner, orthotic insert, or other component of the footwear.

In an example, the third capacitance signal 1203 is received from the foot presence sensor 310, and the third capacitance signal 1203 is compared with the second threshold capacitance 1212, such as using processing circuitry on the foot presence sensor 310 or using the processor circuit 320. In an example that does not consider or use the time-varying reference capacitance 1213, threshold crossings for the third capacitance signal 1203 can be observed at times $T_5$, $T_6$, and $T_8$. The second threshold capacitance 1212 can be adjusted, however, such as in real-time with the sensed information from the foot presence sensor 310. Adjustments to the second threshold capacitance 1212 can be based on the time-varying reference capacitance 1213.

In an example, the second threshold capacitance 1212 is adjusted continuously and by amounts that correspond to changes in the time-varying reference capacitance 1213. In an alternative example, the second threshold capacitance 1212 is adjusted in stepped increments, such as in response to specified threshold change amounts of the time-varying reference capacitance 1213. The stepped-adjustment technique is illustrated in FIG. 14 by the stepped increase in the second threshold capacitance 1212 over the interval shown. For example, the second threshold capacitance 1212 is increased at times $T_7$ and $T_{10}$ in response to specified threshold increases in capacitance, $\Delta C$, in the time-varying reference capacitance 1213. In the example of FIG. 14, the third capacitance signal 1203 crosses the reference-compensated second threshold capacitance 1212 at times $T_5$, $T_6$, and $T_9$. Thus different interrupt signals or interrupt signal timings can be provided depending on whether the threshold is reference-compensated. For example, a fourth interrupt signal $INT_4$ can be generated and provided between times $T_5$ and $T_6$. If the second threshold capacitance 1212 is used without reference compensation, then a fifth interrupt signal $INT_5$ can be generated and provided at time $T_8$. However, if the reference-compensated second threshold capacitance 1212 is used, then the fifth interrupt signal $INT_5$ is generated and provided at time $T_9$ as illustrated when the third capacitance signal 1203 crosses the compensated second threshold capacitance 1212.

Logic circuits can be used to monitor and update threshold capacitance values. Such logic circuits can be incorporated with the foot presence sensor 310 or with the processor circuit 320. Updated threshold levels can be provided automatically and stored in the on-chip RAM. In an example, no input or confirmation from a user is needed to perform a threshold update.

Figure 15:
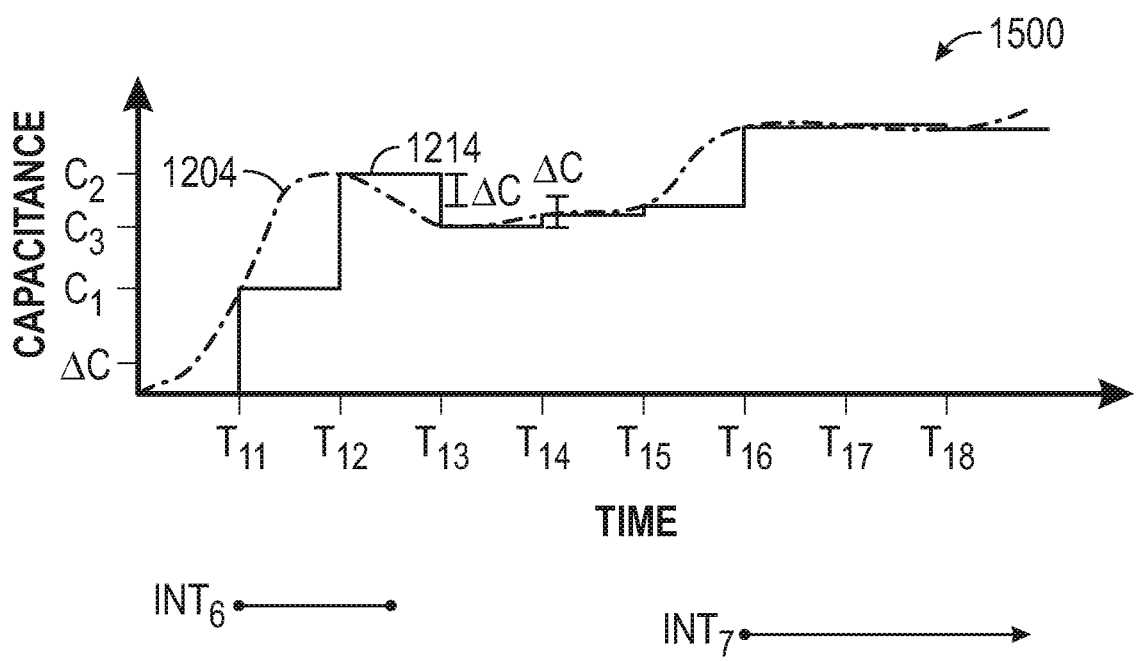
FIG. 15 illustrates generally a chart of fourth time-varying information from a capacitive foot presence sensor.

FIG. 15 illustrates generally a chart 1500 of fourth time-varying information from a capacitive foot presence sensor. The example of FIG. 15 shows how reference capacitance changes, such as due to changes in various ambient conditions, changes in use scenarios, or changes due to wear and tear or degradation of footwear components, can be accounted for. The example includes a fourth capacitance signal 1204 plotted on the chart 1500 with an adaptive threshold capacitance 1214. The fourth capacitance signal 1204 can be provided by the foot presence sensor 310. The adaptive threshold capacitance 1214 can be used to help compensate for environment or use-case-related changes in capacitance measured by the foot presence sensor 310.

In an example, the foot presence sensor 310 or processor circuit 320 is configured to monitor the fourth capacitance signal 1204 for signal magnitude changes, such as for changes greater than a specified threshold magnitude amount. That is, when the fourth capacitance signal 1204 includes a magnitude change that meets or exceeds a specified threshold capacitance magnitude, $\Delta C$, then the foot presence sensor 310 or processor circuit 320 can provide an interrupt signal.

In an example, sensed or measured capacitance values of the fourth capacitance signal 1204 are compared with a reference capacitance or baseline, and that reference or baseline can be updated at specified or time-varying intervals. In the example of FIG. 15, a reference update occurs periodically at times $T_{11}$, $T_{12}$, $T_{13}$, etc., as shown. Other intervals, or updates in response to other triggering events, can additionally or alternatively be used.

In the example of FIG. 15, an initial reference capacitance can be 0, or can be represented by the x-axis. A sixth interrupt signal $INT_6$ can be provided at time $T_{11}$ after the fourth capacitance signal 1204 increases by greater than the specified threshold capacitance magnitude $\Delta C$ relative to a previously specified reference. In the example of FIG. 15, interrupts can be provided at periodic intervals, however, in other examples an interrupt can be provided contemporaneously with identifying the threshold change in capacitance.

Following the identified threshold change, such as at time $T_{11}$, a reference or baseline capacitance can be updated to a first capacitance reference $C_1$. Following time $T_{11}$, the foot presence sensor 310 or processor circuit 320 can be configured to monitor the fourth capacitance signal 1204 for a subsequent change by at least $\Delta C$ in the signal, that is, to look for a capacitance value of $C_1+\Delta C$ or $C_1-\Delta C$.

In an example that includes identifying a capacitance increase at a first time, the interrupt signal status can be changed in response to identifying a capacitance decrease at a subsequent time. However, if a further capacitance increase is identified at the subsequent time, then the reference capacitance can be updated and subsequent comparisons can be made based on the updated reference capacitance. This scenario is illustrated in FIG. 15. For example, at time $T_{12}$, a capacitance increase in the fourth capacitance signal 1204 is detected, and the reference can be updated to a second capacitance reference $C_2$. Since the first and subsequent second capacitance changes represent increases, the status of the sixth interrupt signal $INT_6$ can be unchanged. At time $T_{13}$, a capacitance decrease in the fourth capacitance signal 1204 is detected, and the reference can be updated to a third capacitance reference $C_3$. Since the capacitance change at time $T_{13}$ is a decrease that is greater than the specified threshold capacitance magnitude $\Delta C$, the status of the sixth interrupt signal $INT_6$ can be changed (e.g., from an interrupt asserted state to an unasserted state).

In an example, the first detected change at time $T_{11}$ and corresponding interrupt signal $INT_6$ represents a foot that is sensed by the foot presence sensor 310 and determined to be present in footwear. Subsequent increases in the reference capacitance represent changes to a baseline capacitance measured by the foot presence sensor 310, such as due to environment changes at or near the sensor. The detected change at time $T_{13}$ can represent a foot being removed from the footwear and being no longer sensed proximal to the foot presence sensor 310. A subsequent capacitance change (e.g., at time $T_{16}$) can represent the foot being re-inserted into the footwear.

Figure 16:
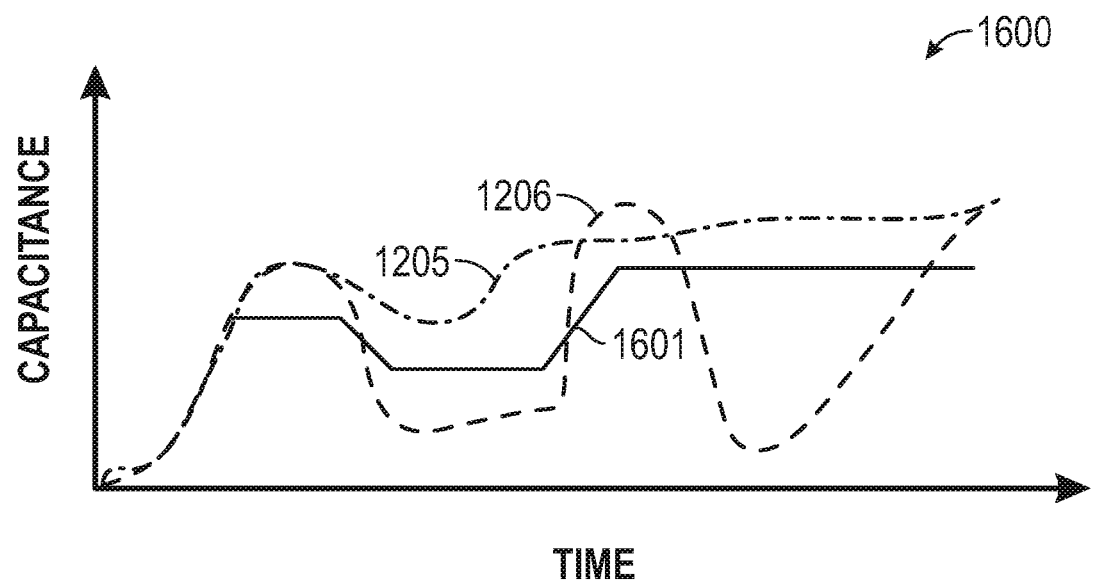
FIG. 16 illustrates generally a chart of time-varying information from a capacitive foot presence sensor and a signal morphology limit, according to an example embodiment.

FIG. 16 illustrates generally a chart 1600 of time-varying information from a capacitive foot presence sensor and a signal morphology limit, according to an example embodiment. The example includes fifth and sixth capacitance signals 1205 and 1206 plotted on the chart 1600. The chart 1600 further includes a morphology limit 1601. The morphology limit 1601 can be compared to sampled segments of a capacitance signal from the foot presence sensor 310. The comparison can be performed using the foot presence sensor 310 or processor circuit 320 to determine whether a particular sampled segment conforms to the morphology limit 1601. In the example of FIG. 16, the morphology limit defines a lower limit that, if exceeded, indicates that the capacitance signal segment does not represent, or is unlikely to represent, a foot presence proximal to the foot presence sensor 310.

The illustrated sampled portion of the fifth capacitance signal 1205 conforms to the morphology limit 1601. In the example of FIG. 16, the morphology limit 1601 defines a morphology that includes a capacitance signal magnitude change, or dip, dwell, and recovery. Following identification that the fifth capacitance signal 1205 conforms to all or a portion of the morphology limit 1601, an interrupt signal can be provided to indicate a foot presence or successful detection.

The illustrated sampled portion of the sixth capacitance signal 1206 does not conform to the morphology limit 1601. For example, the steep decrease and long dwell time of the sixth capacitance signal 1206 falls outside of the bounds defined by the morphology limit 1601, and therefore an interrupt signal can be withheld, such as to indicate that a foot is not detected by the foot presence sensor 310.

The morphology limit 1601 can be fixed or variable. For example, the morphology limit can be adjusted based on information about a reference capacitance, environment, footwear use case, user, sensitivity preference, or other information. For example, the morphology limit 1601 can be different depending on a type of footwear used. That is, a basketball shoe can have a different morphology limit 1601 than a running shoe, at least in part because of the different geometry or materials of the shoes or an amount of time that a user is expected to take to put on or take off a particular footwear article. In an example, the morphology limit 1601 can be programmed by a user, such as to correspond to a user's unique footwear donning or doffing preferences or procedures.

As explained above, the foot presence sensor 310 can have an associated fixed or variable baseline or reference capacitance value. The reference capacitance value can be a function of an electrode surface area, or of an electrode placement relative to other footwear components, or of a footwear orientation, or of an environment in which the sensor or footwear itself it used. That is, a sensor can have some associated capacitance value without a foot present in the footwear, and that value can be a function of a dielectric effect of one or more materials or environmental factors at or near the sensor. In an example, an orthotic insert (e.g., insole) in footwear can change a dielectric characteristic of the footwear at or near a capacitive sensor. The processor circuit 320 can optionally be configured to calibrate the foot presence sensor 310 when a baseline or reference characteristic changes, such as when an insole is changed. In an example, the processor circuit 320 can be configured to automatically detect baseline or reference capacitance changes, or can be configured to update a baseline or reference capacitance in response to a user input or command.

Figure 17:
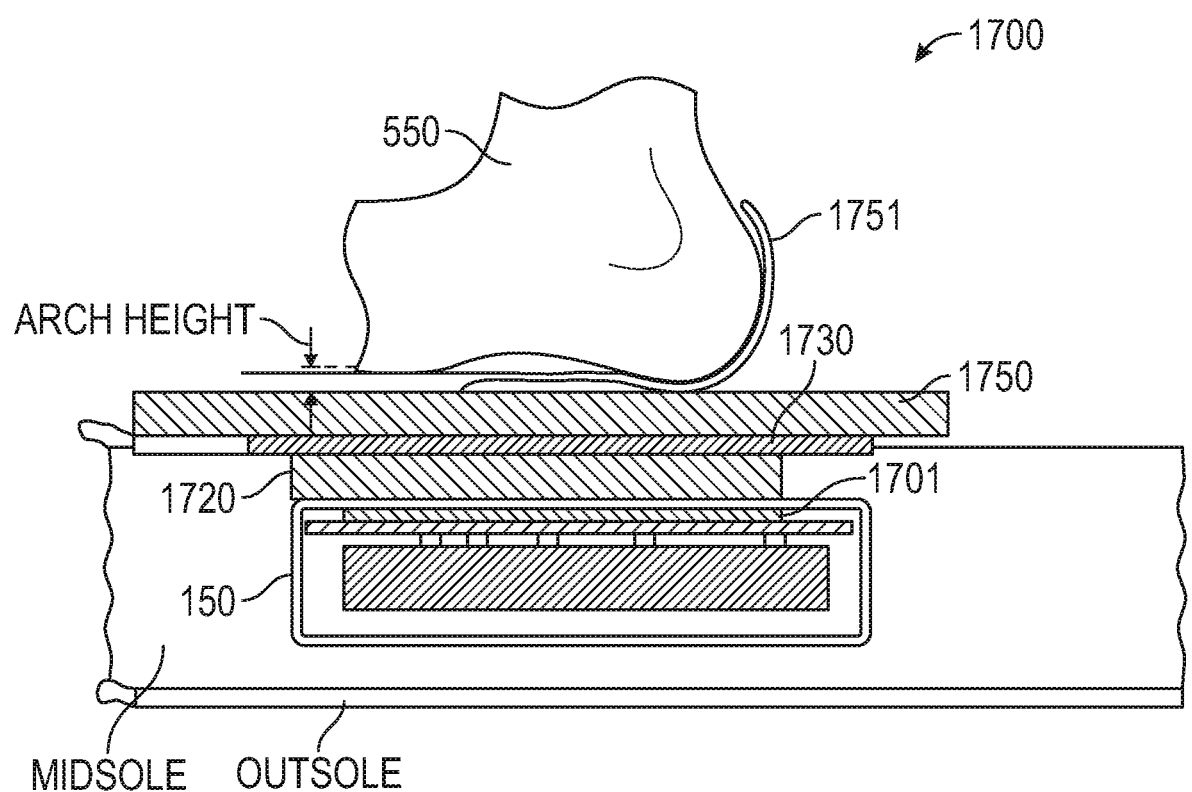
FIG. 17 illustrates generally an example of a diagram of a capacitance-based foot presence sensor in a midsole of a footwear article and located under a dielectric stack.

FIG. 17 illustrates generally an example 1700 of a diagram of a capacitance-based foot presence sensor in a midsole of a footwear article and located under a dielectric stack. The example 1700 includes the housing structure 150, such as can include or use a lacing engine or drive mechanism 340 that is actuated at least in part based on information from a capacitive foot presence sensor 1701. The capacitive foot presence sensor 1701 can be configured to provide a capacitance or capacitance-indicating signal based on a presence or absence of the body 550 proximal to the sensor.

One or more materials can be provided between the body 550 and the capacitive foot presence sensor 1701, and the one or more materials can influence the sensitivity of the sensor, or can influence a signal-to-noise ratio of a signal from the sensor. In an example, the one or more materials form a dielectric stack. The one or more materials can include, among other things, a sock 1751, an airgap such as due to an arch height of the body 550 at or near the sensor, a sock liner 1750, a fastener 1730 such as Velcro, or a dielectric filler 1720. In an example, when the capacitive foot presence sensor 1701 is provided inside of the housing structure 150 the top wall of the housing structure 150 itself is a portion of the dielectric stack. In an example, an orthotic insert can be a portion of the dielectric stack.

The present inventors have recognized that providing a dielectric stack with a high relative permittivity, or a high k-value, can enhance the input sensitivity of the capacitive foot presence sensor 1701. Various high k-value materials were tested and evaluated for effectiveness and suitability in footwear. The dielectric stack can include one or more members specified to have a hardness or durometer characteristic that is comfortable to use underfoot in footwear and that provides a sufficient dielectric effect to increase the sensitivity of the capacitive foot presence sensor 1701, such as relative to having an airgap or other low k-value material in its place. In an example, a suitable material includes one with good weathering or durability, with low and high temperature tolerance, and stress-crack resistance.

In an example, the dielectric filler 1720 can include a neoprene member. The neoprene member includes a closed-cell foam material with about a 30 shore A hardness value. In an example, the dielectric filler 1720 can include a rubber, plastic, or other polymer-based member. For example, the dielectric filler 1720 can include an ethylene-vinyl acetate (EVA) member. The EVA member can have a weight percent of vinyl acetate from about 10 to 40 percent, with the remainder being ethylene. Other proportions can be used. In an example, the dielectric filler 1720 can include a material with enhanced conductivity characteristics, such as including a doped plastic or rubber. In an example, the dielectric filler 1720 includes an EVA member doped with carbon, such as having a greater k-value than a non-doped EVA member having the same or similar ethylene to vinyl acetate percentage.

Figure 18:
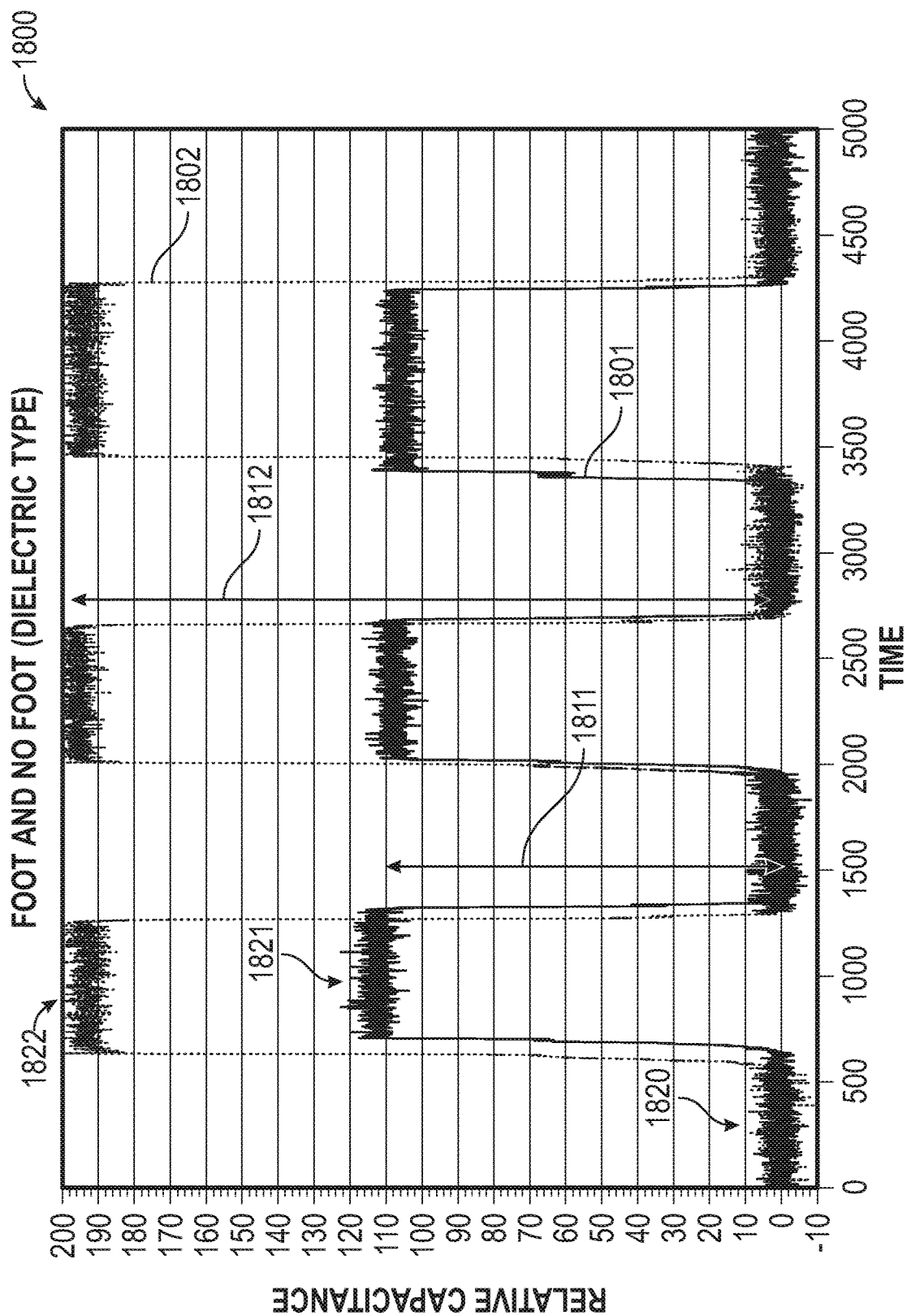
FIG. 18 illustrates generally an example that includes a chart showing an effect of the dielectric filler on a capacitance-indicating signal from the capacitive foot presence sensor.

FIG. 18 illustrates generally an example that includes a chart 1800 showing an effect of the dielectric filler 1720 on a capacitance-indicating signal from the capacitive foot presence sensor 1701. In the chart 1800, the x axis indicates a number of digital samples and corresponds to time elapsed, and the y axis indicates a relative measure of capacitance detected by the capacitive foot presence sensor 1701. The chart 1800 includes a time-aligned overlay of a capacitance-indicating first signal 1801 corresponding to a first type of the dielectric filler 1720 material and a capacitance-indicating second signal 1802 corresponding to a different second type of the dielectric filter 1720.

In the example, the first signal 1801 corresponds to footwear with a first dielectric member provided as the dielectric filler 1720. The first dielectric member can include, for example, a polyurethane foam having a first dielectric k-value. The chart 1800 shows multiple instances of the body 550 being inserted into and then removed from an article of footwear that includes the first dielectric member and the foot presence sensor 1701. For example, a first portion 1820 of the first signal 1801 indicates a reference or baseline capacitance measured by the capacitive foot presence sensor 1701. In the example of FIG. 18, the reference or baseline is normalized to a value of zero. The reference or baseline condition can correspond to no foot present in the footwear. That is, the first portion 1820 of the first signal 1801 indicates that a foot is absent from the footwear. At a time corresponding to approximately sample 600, the body 550 can be inserted into the footwear and can be situated at or near the capacitive foot presence sensor 1701 and the first dielectric member. Following insertion, a magnitude of the first signal 1801 changes, such as by a first amount 1811, and indicates that a foot (or other body) is present in the footwear. In the example of FIG. 18, the body 550 is present in the footwear for a duration corresponding to a second portion 1821 of the first signal 1801, such as corresponding to approximately samples 600 through 1400. At a time corresponding to approximately sample 1400, the body 550 can be removed from the footwear. When the body 550 is removed, the first signal 1801 can return to its reference or baseline value.

In the example of FIG. 18, the second signal 1802 corresponds to footwear with a second dielectric member provided as the dielectric filler 1720. The second dielectric member can include various materials other than the first dielectric member. In an example, the second dielectric member includes a neoprene foam having a second dielectric k-value that exceeds the first dielectric k-value of the first dielectric member discussed above. In an example, the second dielectric member includes an EVA member (e.g., doped with carbon or other material to enhance a dielectric characteristic or k-value of the member) having a third dielectric k-value that exceeds the first dielectric k-value of the first dielectric member.

The chart 1800 shows multiple instances of the body 550 being inserted into and then removed from an article of footwear that includes the second dielectric member and the foot presence sensor 1701. The first portion 1820 of the second signal 1802 indicates a reference or baseline capacitance measured by the capacitive foot presence sensor 1701 and, in the example of FIG. 18, the first portion 1820 of the second signal 1802 indicates that a foot is absent from the footwear. At a time corresponding to approximately sample 600, the body 550 can be inserted into the footwear and can be situated at or near the capacitive foot presence sensor 1701 and the second dielectric member. Following insertion, a magnitude of the second signal 1802 changes, such as by a second amount 1812, and indicates that a foot (or other body) is present in the footwear. In the example, the second amount 1812 exceeds the first amount 1811. The difference in magnitude change is attributed to the type of material used for the dielectric filler 1720. That is, a magnitude of the capacitance-indicating first and second signals 1801 and 1802 can be different when a different dielectric stack is used. When the dielectric stack includes a high k-value dielectric filler 1720, then the difference in magnitude, or difference from baseline, is greater than when a dielectric stack includes a low k-value dielectric filter 1720.

In an example, an orthotic insert comprises a portion of a dielectric stack in footwear. The present inventors performed a variety of tests to evaluate an effect of various orthotic inserts on capacitive foot sensing techniques. Some results of the testing are illustrated generally at FIG. 23 and discussed below. Full and partial length orthotic insoles were tested. The addition of a regular (partial length) orthotic to the footwear increased an overall dielectric effect of the stack and decreased an electric field sensitivity to the presence of a foot. A sensed signal amplitude (e.g., corresponding to a sensed change in capacitance) also decreased in the presence of the orthotic. An RMS amplitude of a noise floor, however, was similar with or without the orthotic. The response under loading and unloading conditions was also similar.

Based on results of the orthotics tests, using capacitive sensing for detection of foot presence with regular or full-length orthotics is feasible with respect to signal to noise resolution. Using partial or full length orthotics, a SNR exceeding a desired minimum of about 6 dB can be used to resolve foot presence, and can be used under both light duty and high duty loading conditions. In an example, the foot presence sensor 310 can include or use a capacitance offset range to compensate for added dielectric effects of orthotics.

Variations in an air gap between a full-length orthotic and electrodes of the foot presence sensor 310 can correspond to measurable variations in SNR as a function of an applied load. For example, as demonstrated in the example of FIG. 18, when a high k-value dielectric material is provided at or near a capacitive foot presence sensor, then the SNR can be improved over examples that include or use a low k-value dielectric material.

Various foot zones were found to behave similarly under low loading conditions, such as showing no significant deformation of the gap distance under the orthotic. Under high loading conditions, however, such as when a user is standing, an arch region of an orthotic can be compressed and an air gap can be substantially minimized or eliminated. Thus under sensing conditions, measured electric fields in the presence of an orthotic can be similar in magnitude to electric fields measured using a production or OEM insole. In an example of an orthotic or OEM production insole that creates an airgap between the foot presence sensor 310 and a body to be detected, various materials can be provided or added to compensate for or fill in the airgap. For example, a gap-filling foam such as neoprene or doped EVA can be provided at an underside of a full-length orthotic.

In an example, including an orthotic in an insole increases an overall dielectric thickness of a dielectric stack, and decreases an electric field sensitivity of a capacitive sensor to the presence of the foot. In other words, a resulting signal amplitude from the capacitive sensor generally decreases when an orthotic insert is used. An RMS amplitude of a noise characteristic was observed to be generally similar with or without the orthotic. It was also determined that a dielectric member that occupies a volume between a sense electrode of a capacitive sensor and a lower surface of an orthotic can have a large influence on a sensitivity of the capacitive sensor. A polyurethane foam, for example having a k-value of 1.28, can have about 700/% less signal amplitude than that measured when using a neoprene foam with a dielectric constant or k-value of about 5.6. With noise amplitude being equal, this equates to an SNR difference of about 4.6 dB. Using capacitive sensing for detection of foot presence with carbon fiber orthotics is thus feasible with respect to signal to noise. For example, the SNR exceeds the minimum of 6 dB desired to resolve foot presence.

Figure 19:
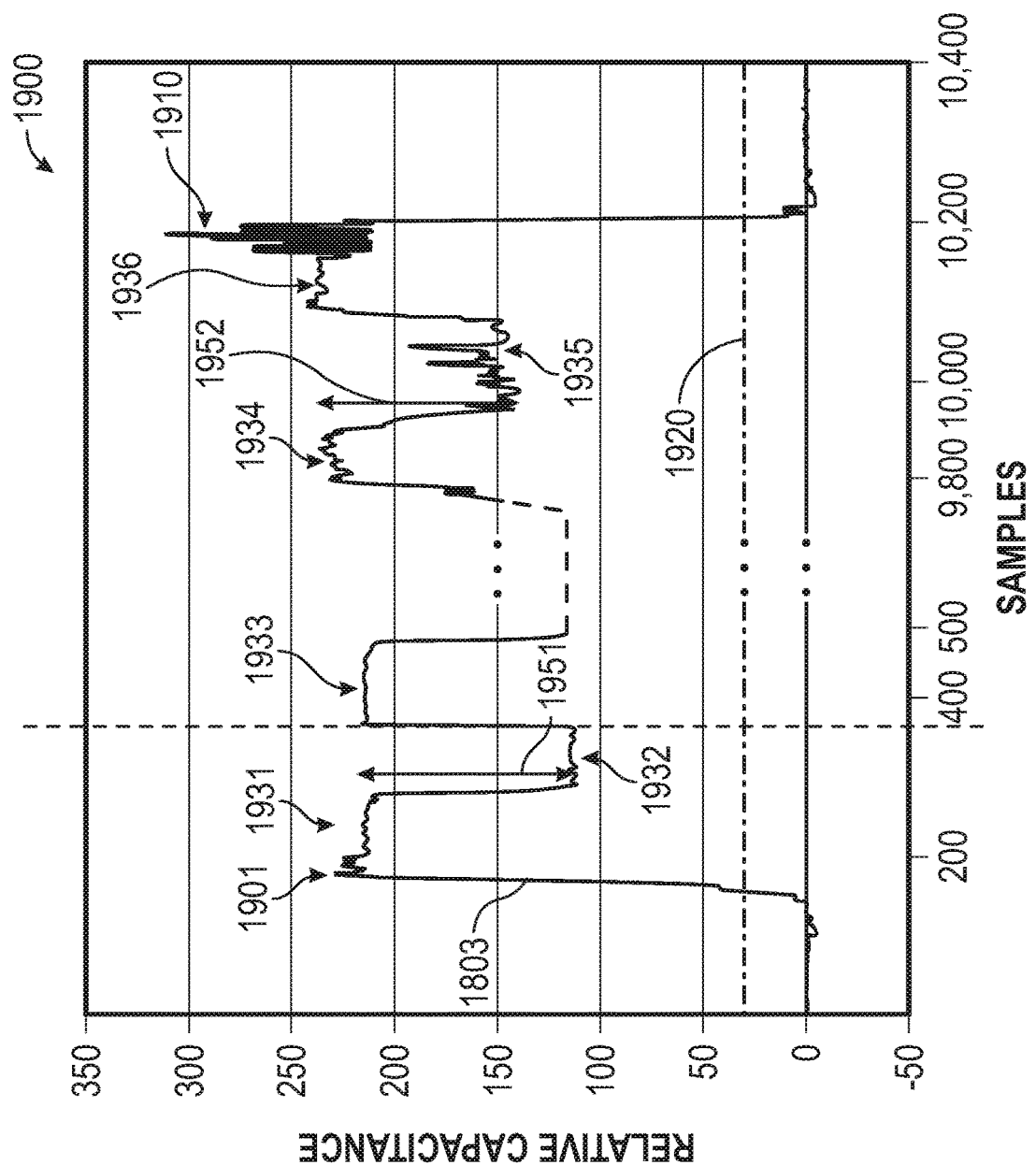
FIG. 19 illustrates generally an example of a chart that shows a portion of a capacitance-indicating third signal from a capacitance-based foot presence sensor in footwear.

FIG. 19 illustrates generally an example of a chart 1900 that shows a portion of a capacitance-indicating third signal 1803 from a capacitance-based foot presence sensor in footwear. In the chart 1900, the x axis indicates a number of digital samples and corresponds to time elapsed, and the y axis indicates a relative measure of capacitance detected by the capacitive foot presence sensor 1701. Information from the third signal 1803 can be used to determine whether a user is applying a downward force on the footwear, such as can be used to discern whether the user is sitting or standing, or to determine a step count, or to determine a user gait characteristic, among other things. In the example of FIG. 19, a mutual capacitance sensing mode was used. In the mutual capacitance sensing mode, increased capacitance as detected by the sensor corresponds to a decrease in the signal as illustrated. In another example, a self capacitance sensing mode can be used. In a self capacitance mode, increased capacitance as detected by the sensor (e.g., corresponding to compression of a foam insert over the sensor) would correspond to an increase in the signal.

In the example of FIG. 19, at an initial time, such as corresponding to sample "0" on the x axis, the third signal 1803 can have a reference or baseline value of about 0 on the relative capacitance scale. At 1901, or at about sample 175 on the x axis, the third signal 1803 includes a footwear donning event corresponding to, e.g., the body 550 being inserted into the footwear. The third signal 1803 includes a footwear doffing event at 1910, or at about sample 10000, after which the third signal 1803 returns to the baseline value.

The example of FIG. 19 further includes a specified threshold 1920. The threshold 1920 can correspond to a relative capacitance value that indicates the body 550 is present in the footwear. For example, when a foot or the body 550 is present in the footwear, the relative capacitance indicated by the third signal 1803 exceeds the threshold 1920, and when the foot or body 550 is absent from the footwear, the 30 relative capacitance can fall below the threshold 1920. Various methods or techniques can be used to dynamically adjust the threshold 1920, such as further described herein, such as to account for environmental changes or footwear material changes.

Between the footwear donning and doffing events at 1901 and 1910, respectively, such as corresponding to an interval between samples 175 and 10250, the wearer of the footwear article can transition multiple times between sitting and standing positions. Transitions between sitting and standing can correspond to fluctuations in the third signal 1803 for example due to compression and relaxation of footwear materials that form a dielectric stack over a capacitive sensor that provides the third signal 1803. That is, when a user stands and exerts a downward force on the dielectric stack, one or more materials in the dielectric stack can compress and the user's foot can move closer to the capacitive sensor, thereby changing a relative capacitance measured using the sensor. When a user sits and the downward force on the dielectric stack is reduced, then the dielectric stack materials can relax or extend, and the user's foot can move away from the capacitive sensor.

The donning event 1901 includes a turbulent portion of the third signal 1803. That is, instead of showing a smooth or gentle transition, the third signal 1803 fluctuates rapidly and erratically as the user seats his or her foot into position within the footwear. In an example, the donning event 1901 includes lacing, such as automatic or manual lacing, which can correspond to a user exerting various forces on the footwear materials, including on the dielectric stack, and the user adjusting the footwear's tension about the user's foot and thus correspondingly adjusting a position of the user's foot with respect to the capacitive sensor. In the example of FIG. 19, following the donning event at 1901, a user can be seated for a first duration 1931, such as corresponding to samples 200 through 275. For the first duration 1931, the third signal 1803 can have an average value of about 220 relative capacitance units.

Following the first duration 1931, the user can stand, causing the material(s) of the dielectric stack to compress and thereby permitting the user's foot to approach the capacitive sensor under the stack. When the user is fully standing and compressing the dielectric stack, the third signal 1803 can have an average value of about 120 relative capacitance units for a second duration 1932. That is, a magnitude of the third signal 1803 can change by a first magnitude change amount 1951 as the user transitions from sitting to standing, or as the user transitions from exerting minimal force on the dielectric stack to exerting a greater or maximum force on the dielectric stack, and thereby changing a dielectric characteristic of the dielectric stack itself. In an example, the first magnitude change amount 1951 can correspond to a magnitude of the force exerted on the dielectric stack. That is, the first magnitude change amount 1951 can be used to determine, among other things, a user's weight or whether the user is running or walking, for example because the user is expected to exert a greater force on the dielectric stack when running as compared to walking.

In the example of FIG. 19, at about sample 375, the third signal 1803 returns to a value of about 220 relative capacitance units when the user returns to a seated posture. The user sits for a third duration 1933 before the next relative capacitance change.

A dashed-line portion of the third signal 1803 (following about sample 500 in the example of FIG. 19) indicates a time passage and a change in scale of the x axis. In an example, the samples 0 through 500 correspond to a time when footwear incorporating the capacitive sensor is new, or when a new dielectric stack is used with the footwear. The samples following about sample 9,800 can correspond to a time when the footwear is older or partially worn out, or when a portion of the dielectric stack is compressed and fails to fully recoil or expand under relaxed or non-use conditions.

In the example of FIG. 19, the third signal 1803 indicates several user transitions between sitting and standing postures. In the example, a fourth duration 1934 and a sixth duration 1936 correspond to a sitting posture with minimal force or pressure applied to a dielectric stack in the footwear. A fifth duration 1935 corresponds to a standing posture with elevated force applied on the dielectric stack. In the example, the fourth and sixth durations 1934 and 1936 can correspond to an average value of about 240 relative capacitance units. That is, the average of the fourth and sixth durations 1934 and 1936 can exceed the average of the first and third durations 1931 and 1933, which was about 220 units. In an example, the difference between the average values can be attributed to wear and tear of one or more portions of the dielectric stack or other footwear materials that change over time with use of the footwear. In the example, the fifth duration 1935 can correspond to an average value of about 150 relative capacitance units, which exceeds the average value of about 120 units for the third duration 1933. Furthermore, the difference between sitting and standing postures, that is between force applied or not applied to the dielectric stack, can differ for the case of the new footwear and the used footwear. The first magnitude change amount 1951 indicates about a 200 unit change in relative capacitance for new footwear between standing and seated postures, and a second magnitude change amount 1952 indicates about a 150 unit change in relative capacitance for older or used footwear between standing and seated postures. In the example of FIG. 19, the fourth through sixth durations 1934-1936 further indicate a relatively noisy signal as compared to the first through third durations 1931-1933, which can additionally be attributed to wear and tear of footwear or sensor components.

FIG. 19 thus illustrates that information from the third signal 1803 can be used to indicate, among other things, a footwear lifecycle status or footwear usage characteristic. The information can be used, for example, to help prevent user injury by reporting to or warning a user that one or more footwear components are worn or exhausted, and may no longer be available to provide optimal or sufficient cushioning or foot retention. For example, information from the third signal 1803 can be used to determine a lifecycle status of a footwear component such as an insole component, orthotic insert, or other component of the footwear.

In an example, information from a capacitive foot sensor can be used to derive or determine step frequency information, which can in turn be used as a step counter or pedometer, such as when a user's stride is known or determinable. Referring again to FIG. 19, fluctuations in the third signal 1803 can correspond to different step events. For example, the second duration 1932 can correspond to an interval that includes a first portion of a user step, such as when a user's first foot is on the ground and the user's body weight applies a force on the user's footwear, and the footwear includes a capacitance-based foot presence sensor that provides the third signal 1803. Following the second duration 1932, the user can shift his or her weight from the user's first foot to his or her second foot. As a result, pressure or force applied by the user to the footwear can be reduced, and a corresponding change in the third signal 1803 can be observed. For example, a magnitude of the third signal 1803 can increase, such as by the first magnitude change amount 1951. When the user steps again and returns to the first foot, then the magnitude of the third signal 1803 can decrease, such as by the same or similar first magnitude change amount 1951. In an example, the magnitude change can depend on, or can be related to, a force applied by the user on the footwear, which can in turn correspond to how quickly the user is walking or running. For example, a greater magnitude change amount can correspond to a running pace, while a lesser change amount can correspond to a walking pace. Thus a user's pace can be determined using one or both of a magnitude change amount and a frequency or rate of magnitude change events.

In an example, a duration, interval, or sample count of a specified portion of the third signal 1803 can be used to determine a step interval or step count. For example, the first duration 1931 can have a sample count of about 75 samples, and the second duration 1932 can have a sample count of about 50 samples. If the first duration 1931 corresponds to a first portion of a user's walking or stepping cycle when a first foot is off the ground, and the second duration 1932 corresponds to a later second portion of the user's walking or stepping cycle when the first foot is on the ground, then the user can have a step interval of about 125 samples. Depending on the sample rate, the step interval can be correlated with a walking or running pace, such as using the processor circuit 320 to process the sample count information.

In an example, a duration, interval, or sample count between signal magnitude changes in the third signal 1803 can be used to determine a step interval or step count. Magnitude changes, such as greater than a specified threshold magnitude change amount, can be identified by the processor circuit 320, and then the processor circuit 320 can calculate or identify interval lengths between the identified magnitude changes. For example, an onset of the second duration 1932 can be identified by the processor circuit 320 to be at about sample 325, such as corresponding to a magnitude change observed in the third signal 1803 that is greater than a specified threshold change. An end of the second duration 1932 can be identified by the processor circuit 320 to be at about sample 375, such as corresponding to a subsequent magnitude change observed in the third signal 1803 and is greater than the specified threshold change. The processor circuit 320 can calculate a difference between the sample counts and determine that the second duration 1932 is about 50 samples in duration. The processor circuit 320 can similarly determine a duration or sample length for any one or more segments of the third signal 1803. The processor circuit 320 can then determine a step interval, and a step interval can be used to determine a distance traveled or a rate at which the user is moving. In an example, information about a user's stride length can be used together with the step interval information to determine the distance traveled.

In an example, a user's stride length is not specified or known. The user's stride length can optionally be determined using information from one or more other sensors, such as an accelerometer or position sensor (e.g., a GPS sensor) in coordination with the foot sensor information. For example, information from a position sensor can indicate a total distance traveled by a user over a specified duration. The processor circuit 320, or other processor appurtenant to the footwear, can receive the third signal 1803 and correlate a number of signal magnitude change events with steps and distance traveled to determine an average user step or stride length. For example, if a user travels 100 meters in 30 seconds, and a capacitance-indicating signal from a foot presence sensor indicates 100 signal magnitude change events within the same 30 second interval, then the processor circuit 320 or other processor can determine the user's stride is about 100 meters/100 magnitude change events=1 meter per magnitude change event.

In an example, information from the third signal 1803 can be used to determine a user gait characteristic, or a change in a user's gait. The processor circuit 320 can, for example, be configured to monitor the capacitance-indicating signal over time, such as to identify changes in the signal. For example, the processor circuit 320 can monitor a first (or other) duration or first step event after a detected donning event. Generally, users can be expected to begin walking or running in a similar manner, such as using a similar gait, each time the user dons the footwear. If the processor circuit 320 detects a deviation from an established baseline or average signal characteristic following footwear donning, then the user can be alerted. Similarly, the processor circuit 320 can be configured to detect usage characteristics or deviations that can be associated with user fatigue or mood, which can in turn lead to injury. For example, a deviation from an established baseline or reference signal characteristic can indicate a foot or ankle has rotated or slid within the footwear, such as because a foot position change can correspondingly change a dielectric characteristic at or above a capacitance-based foot presence sensor. In an example that includes an automatic lacing engine, information about the foot position change can be used to automatically tighten the footwear about the user's foot to help prevent injury to the user.

Figure 20:
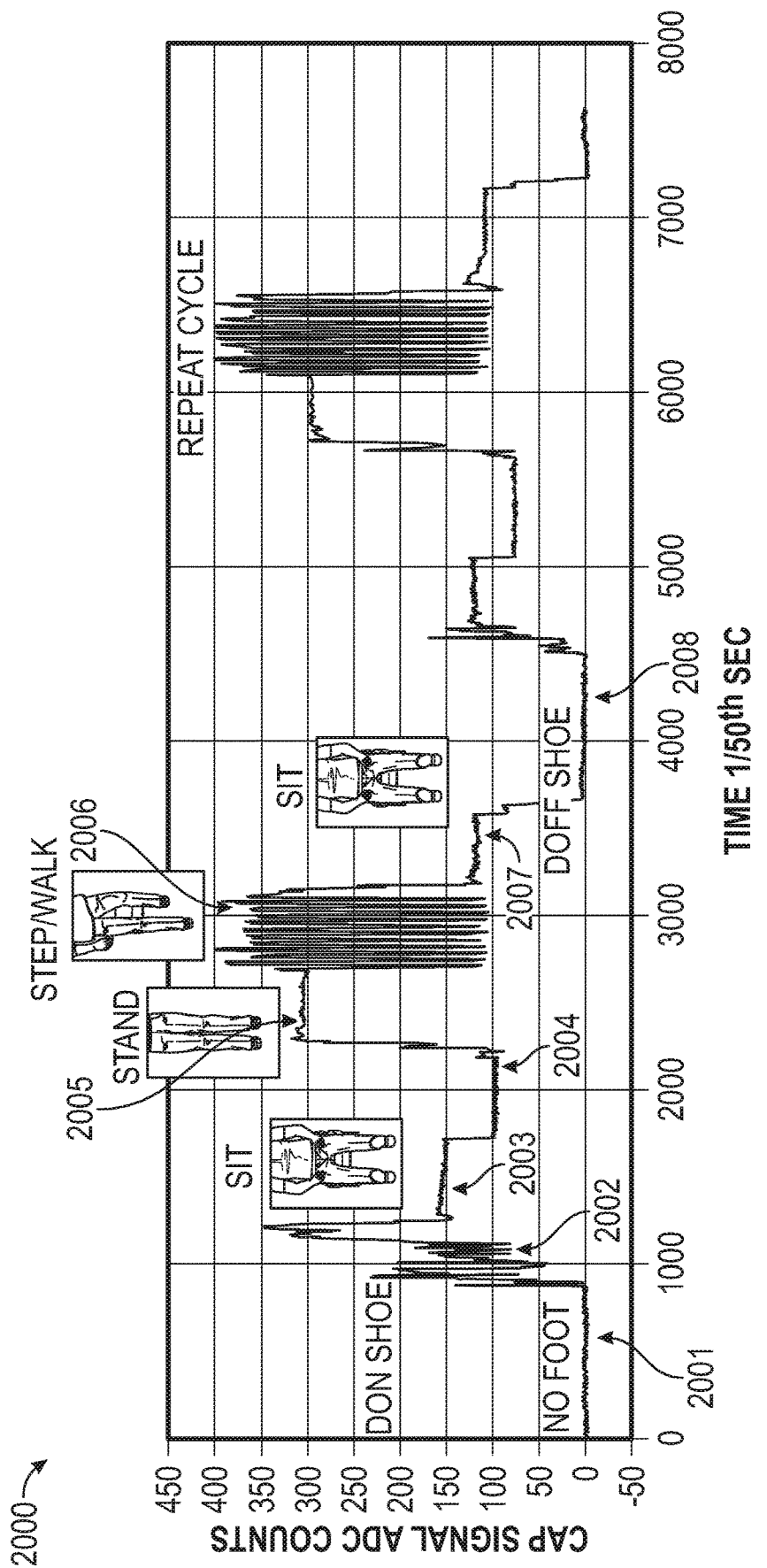
FIG. 20 illustrates generally an example of foot presence signal information over multiple sit-stand cycles.

FIG. 20 illustrates generally an example of foot presence signal information over multiple sit-stand cycles. The example includes a chart 2000 that shows a relationship between time (x-axis) and "counts" (y-axis). The counts correspond to an output of a capacitive foot presence sensor. For example, the counts can correspond to a digital signal from an analog to digital converter that receives an analog output from a capacitive sensor.

In the example of FIG. 20, zero counts indicates a reference condition, such as corresponding to no foot being present in footwear that includes the sensor. Greater than zero counts indicates that the capacitive foot presence sensor senses something other than a no-foot condition, such as a foot or other body or object that is present in or proximal to the sensor and therefore the footwear. A magnitude of the counts corresponds to a location of the sensor's target, such as a foot, relative to the sensor's electrodes. In some examples, the magnitude of the counts corresponds to a force applied by a foot to the footwear's sole, such as described above in the example of FIG. 19. For example, when a foot is present in the footwear and the wearer is sitting, and therefore not applying significant force to the sole of the footwear, then a first, lesser number of counts can be registered by the sensor. When the foot is present in the footwear and the wearer is standing, and therefore is applying a relatively significant force to the sole of the footwear, then a second, greater number of counts can be registered by the sensor. These and other count magnitude change conditions are illustrated generally in FIG. 20. In the example of FIG. 20, a self capacitance sensing mode is used. Accordingly, increases in detected capacitance correspond to increases in the signal as illustrated.

In the example of FIG. 20, a no-foot condition interval is indicated at a first interval 2001 from time zero to about time 900. During the no-foot condition of the first interval 2001, the sensor registers about zero counts. Following the no-foot condition first interval 2001, a first donning interval 2002 is indicated from about time 900 to about time 1250. During the first donning interval 2002, the counts fluctuate as a wearer's foot enters the shoe and is seated against the footbed, and as the wearer adjusts the footwear, such as including flattening any folds in an insert which bears upon the foot.

Following the first donning interval 2002, a first sit interval 2003 is indicated from about time 1250 to time 1750. During the first sit interval 2003, the counts settle to a baseline value of about 150 counts. During the first sit interval 2003, the wearer is substantially stationary and maintains a relaxed posture. The counts magnitude is maintained at a substantially constant value as long as the wearer remains stationary. Following the first sit interval 2003, a first raised-foot interval 2004 is indicated from about time 1750 to time 2200. During the first raised-foot interval 2004, the wearer remains seated but raises his or her feet off the floor to thereby remove any downward force applied to the footwear with the sensor. Since the wearer's foot is still physically present in the footwear during the first raised-foot interval 2004, the counts magnitude remains greater than zero but is less than the magnitude observed during the first sit interval 2003 because less force is applied on the sensor. In the example of FIG. 20, the sensor registers about 100 counts during the first raised-foot interval 2004.

Following the first raised-foot interval 2004, a first stand interval 2005 is indicated from about time 2200 to time 2750. During the first stand interval 2005, the wearer places his or her feet on the floor and stands upright to thereby exert a downward force on the footwear and the sensor. As observed from FIG. 20, the counts magnitude increases to about 300 counts during the first stand interval 2005. The counts magnitude can be greater than the magnitude as observed during the first sit interval 2003 and the first raised-foot interval 2004 because of a greater relative force applied by the wearer on the footwear during the first stand interval 2005, which compresses a dielectric member above the capacitive sensor's electrode(s) and thereby increases the capacitance as detected by the sensor. Following the first stand interval 2005, a first step/walk interval 2006 is indicated from about time 2750 to time 3200. During the first step/walk interval 2006, the wearer takes steps or walks while wearing the footwear. The counts magnitude fluctuates during the first step/walk interval 2006, and the fluctuations correspond to step cycles of the wearer. For example, count magnitude peaks or maxima during the first step/walk interval 2006 correspond to instances when the wearer applies force to the footwear that includes the sensor, such as when the wearer's foot contacts the ground. Count magnitude valleys or minima during the first step/walk interval 2006 correspond to instances when the wearer lifts the foot. The peak magnitude values generally exceed the magnitude of the count values observed during the first stand interval 2005, and the minimum magnitude values generally correspond to the values observed during the first raised-foot interval 2004. In an example, count plateau regions correspond to a duration of time that the foot is provided on the ground (e.g., corresponding to a step event) or to a duration of time that the foot is lifted off of the ground. Accordingly a user's rate of travel can be discerned or determined based on a relative length of each plateau region.

Following the first step/walk interval 2006, a second sit interval 2007 is indicated from about time 3200 to time 3600. The counts magnitude during the second sit interval 2007 is, in the example of FIG. 20, less than the counts magnitude observed during the first sit interval 2003. The change can be attributed to, among other things, changes in a baseline or reference capacitance of the sensor, environmental effects, or the wearer's posture following the first step/walk interval 2006.

Following the second sit interval 2007, a first doffing interval 2008 is indicated from about time 3600 to about time 3750. During the first doffing interval 2008, the counts fluctuate as a wearer's foot exits and is removed from the footwear. Following the first doffing interval 2008, the counts magnitude returns to its baseline value of about zero counts, corresponding to a no-foot condition.

Following the return to zero counts at about time 3750, the example of FIG. includes a second cycle beginning at about time 4500 that includes another donning interval, sit interval, raised-foot interval, stand interval, step/walk interval, second sit interval, and doffing interval, in that order.

In an example, a foot presence threshold can be used to determine whether a foot is present in, or absent from, footwear that includes a capacitive foot presence sensor. For the sensor configuration used to generate the example of FIG. 20, for example, a foot presence threshold can be chosen to be about 30 signal counts from the sensor. The foot presence threshold can indicate that a foot is present in the footwear (or that there is a strong likelihood that a foot is present in the footwear) when greater than a specified number of counts is observed. Similarly, the foot presence threshold can indicate that a foot is absent from the footwear (or that there is a strong likelihood that a foot is absent from the footwear) when less than a specified number of counts is observed.

In an example, the foot presence threshold can be adapted or changed, such as in response to changes in sensor characteristics, changes in environmental influences on the sensor, and changes in user preferences. For example, if a sensor electrode is damaged or altered, then a baseline capacitance value of the sensor can be changed, and accordingly a reference measurement from the sensor can be altered. In an example, various electric and/or magnetic fields can influence behavior of the sensor, which can cause a baseline capacitance value of the sensor to be changed. In an example, a user can adjust foot presence sensing sensitivity of the sensor, such as to make the sensor (and the function(s) it triggers) more responsive or less response to a foot detection event. The foot presence threshold can be adjusted to accommodate any one or more of these or other changes without a loss of its foot presence sensing functionality.

FIGS. 21A-21D illustrate generally examples of different planar electrode assembly configurations. The shape or profile of each of the assemblies conforms generally to a shape of the lacing engine enclosure or housing configured to house the electrode assembly, however, other shapes can similarly be used. In the examples of FIGS. 21A-21D, the electrode assemblies are generally planar and include a first conductive region or electrode about the perimeter (illustrated generally as a shaded region) and a second non-conductive region located generally centrally and encircled by the first conductive region. Other examples can have multiple conductive and non-conductive regions, such as can be arranged side-by-side or concentrically.

Figures 21A, 21B, 21C:
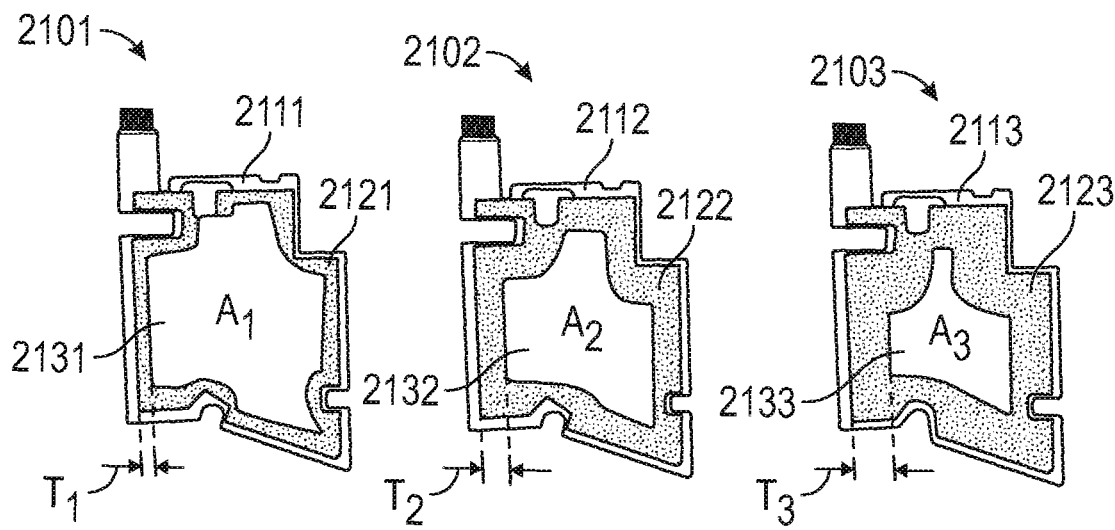
FIGS. 21A-21D illustrate generally examples of different planar electrode configurations.

FIG. 21A includes a first electrode assembly 2101 that includes a central first non-conductive region 2131 having a first surface area $A_1$, and a first electrode region 2121 having an average first thickness $T_1$. In an example, the average first thickness $T_1$ is about 2 millimeters, and includes an approximately 2 mm wide conductive strip or loop that extends substantially about the perimeter of the first electrode assembly 2101. In an example, the assembly includes a first non-conductive border 2111 outside of the first electrode region 2121.

FIG. 21B includes a second electrode assembly 2102 that includes a central second non-conductive region 2132 having a second surface area $A_2$ that is less than $A_1$. The second electrode assembly 2102 includes a second electrode region 2122 having an average second thickness $T_2$ that is greater than $T_1$. In an example, the average second thickness $T_2$ is about 4 millimeters, and includes an approximately 4 mm wide conductive strip or loop that extends substantially about the perimeter of the second electrode assembly 2102. In an example, the assembly includes a second non-conductive border 2112 outside of the second electrode region 2122.

FIG. 21C includes a third electrode assembly 2103 that includes a central third non-conductive region 2133 having a third surface area $A_3$ that is less than $A_2$. The third electrode assembly 2103 includes a third electrode region 2123 having an average third thickness $T_3$ that is greater than $T_2$. In an example, the average third thickness $T_3$ is about 6 millimeters, and includes an approximately 6 mm wide conductive strip or loop that extends substantially about the perimeter of the third electrode assembly 2103. In an example, the assembly includes a third non-conductive border 2113 outside of the third electrode region 2123.

Figure 21D:
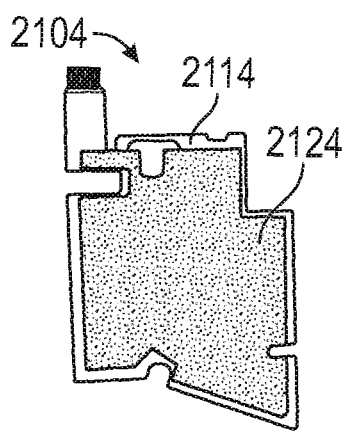

FIG. 21D includes a fourth electrode assembly 2104 that includes a central flood electrode region 2124 having a surface area that is greater than that of any of the first through third electrode regions 2121-2123 in the examples of FIGS. 21A-21C. In an example, the assembly includes a fourth non-conductive border 2114 outside of the central flood electrode region 2124. That is, the fourth electrode assembly 2104 includes an electrode that occupies substantially all of the available surface area and does not include a central non-conductive region.

FIG. 22 illustrates generally an example of a chart that shows a relationship between capacitive sensor sensitivity and sensor shape. Each of the illustrated curves corresponds to data obtained using a different one of the electrode assemblies from the examples of FIGS. 21A-21D. For example, the first curve 2201 corresponds to the first electrode assembly 2101 (e.g., with a 2 mm wide first electrode region 2121), the second curve 2202 corresponds to the second electrode assembly 2102 (e.g., with a 4 mm wide second electrode region 2122), the third curve 2203 corresponds to the third electrode assembly 2103 (e.g., with a 6 mm wide third electrode region 2123), and the fourth curve 2204 corresponds to the fourth electrode assembly 2104 (e.g., with a flood electrode region 2124).

In the example of FIG. 22, the first through fourth curves 2201-2204 indicate relationships between a foot strike force on a particular one of the capacitive sensors and a number of resulting counts from the sensor (see discussion above regarding "counts" as an output from a capacitive sensor, or from a processor such as an ADC circuit coupled to a capacitive sensor). For example, the first curve 2201 indicates that when a weight of about 20 pounds is applied atop a capacitive sensor that includes the first electrode assembly 2101, then the resulting number of counts from the sensor is about 20. The first curve 2201 further indicates that when a weight of about 100 pounds is applied atop the same capacitive sensor, then the resulting number of counts from the sensor is about 70. Over the illustrated interval from 20 to 80 pounds of force, a sensor that includes the first electrode assembly 2101 thus indicates a difference of about 50 counts.

In the example of FIG. 22, the second curve 2202 indicates that when a weight of about 20 pounds is applied atop a capacitive sensor that includes the second electrode assembly 2102, then the resulting number of counts from the sensor is about 60. The second curve 2202 further indicates that when a weight of about 100 pounds is applied atop the same capacitive sensor, then the resulting number of counts from the sensor is about 170. Over the illustrated interval from 20 to 80 pounds of force, a sensor that includes the second electrode assembly 2102 thus indicates a difference of about 110 counts.

In the example of FIG. 22, the third curve 2203 indicates that when a weight of about 20 pounds is applied atop a capacitive sensor that includes the third electrode assembly 2103, then the resulting number of counts from the sensor is about 75. The third curve 2203 further indicates that when a weight of about 100 pounds is applied atop the same capacitive sensor, then the resulting number of counts from the sensor is about 190. Over the illustrated interval from 20 to 80 pounds of force, a sensor that includes the third electrode assembly 2103 thus indicates a difference of about 115 counts.

In the example of FIG. 22, the fourth curve 2204 indicates that when a weight of about 20 pounds is applied atop a capacitive sensor that includes the fourth electrode assembly 2104, then the resulting number of counts from the sensor is about 80. The fourth curve 2204 further indicates that when a weight of about 100 pounds is applied atop the same capacitive sensor, then the resulting number of counts from the sensor is about 255. Over the illustrated interval from 20 to 80 pounds of force, a sensor that includes the fourth electrode assembly 2104 thus indicates a difference of about 175 counts.

Each of the different sensor electrode assemblies or configurations indicates a substantially linear relationship over the illustrated weight interval. However, the different slopes of the first through fourth curves 2201-2204 indicates different sensor sensitivities to weight changes. For example, the first curve 2201 indicates that the first electrode assembly 2101 is relatively less sensitive to weight changes, showing only about a 50 count difference over a swing of 60 pounds of force. In contrast, the fourth curve 2204 indicates that the fourth electrode assembly 2104 is relatively more sensitive to weight changes, and shows about a 175 count difference over the same swing of 60 pounds of force. Thus a sensor that includes or uses the fourth electrode assembly 2104 can, in some examples, provide greater resolution and more information about weight-change related events, such as standing, sitting, or step/walk events.

Figure 23:
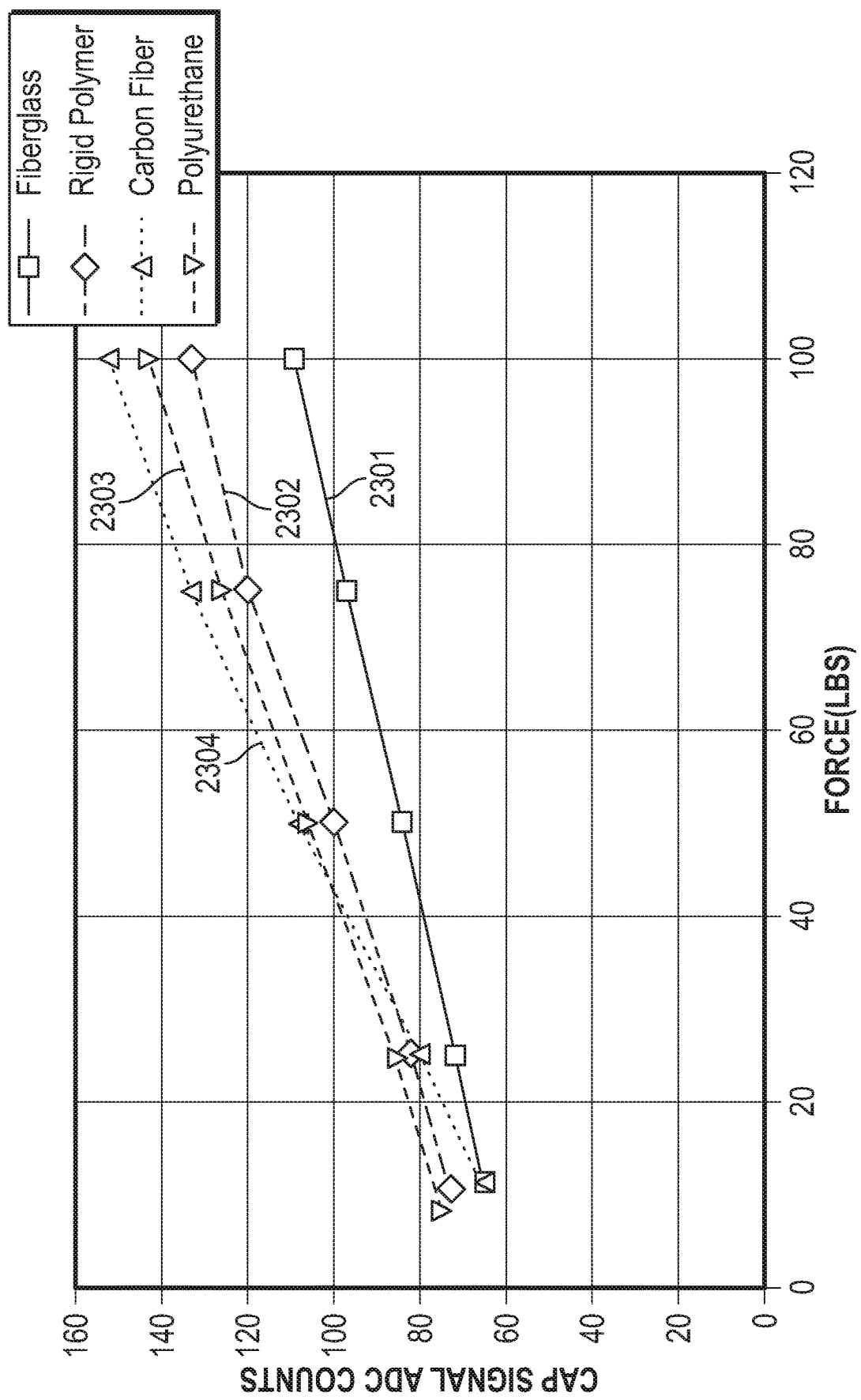
FIG. 23 illustrates generally an example of a chart that shows a relationship between sensor sensitivity and types of orthotic inserts.

FIG. 23 illustrates generally an example of a chart that shows a relationship between sensor sensitivity and various types of orthotic inserts. As explained above, an orthotic insert can comprise a portion of a dielectric stack in footwear. The present inventors performed a variety of tests to evaluate an effect of various orthotic inserts on capacitive foot sensing using the planar electrode configurations discussed above. In the example of FIG. 23, the third electrode assembly 2103 (e.g., with a 6 mm wide conductor) was used during testing. Full and partial length orthotic insoles were tested. The addition of a regular (partial length) orthotic to the footwear increased an overall dielectric effect of the stack and decreased an electric field sensitivity to the presence of a foot. A sensed signal amplitude (e.g., corresponding to a sensed change in capacitance) also decreased in the presence of the orthotic. An RMS amplitude of a noise floor, however, was similar with or without the orthotic. The response under loading and unloading conditions was also similar. In the example of FIG. 23, a baseline or reference capacitance or offset was established for each insert tested so as to zero the test system.

In the example of FIG. 23, a first orthotic curve 2301 corresponds to a fiberglass insert, a second orthotic curve 2302 corresponds to a rigid polymer insert, a third orthotic curve 2303 corresponds to a polyurethane insert (e.g., a "standard" or factory-supplied insole material), and a fourth orthotic curve 2304 corresponds to a carbon fiber insert. Each of the first through fourth orthotic curves 2301-2304 indicates that the generally linear relationship (see, e.g., FIG. 22) between force and sensor output, or counts, is substantially preserved when an orthotic insert is used.

In the example of FIG. 23, a baseline or reference capacitance value can be different for each insert. In the example, the carbon fiber insert has a greater sensor capacitance relative to the others. In the example of FIG. 23, the sensor response (as indicated by the slope) for a given insert decreases with an increasing stiffness, as long as the insert is non-conductive. In other words, a more stiff or rigid insert generally corresponds to a flatter response curve. Since carbon fiber is conductive, the curve is instead the steepest among those tested. This capacitance increase with compression is greatest because the conductive insert directs the e-field from the sensor back to signal ground via a shorter, higher-capacitance path than is provided when the other inserts are used.

Figure 24:
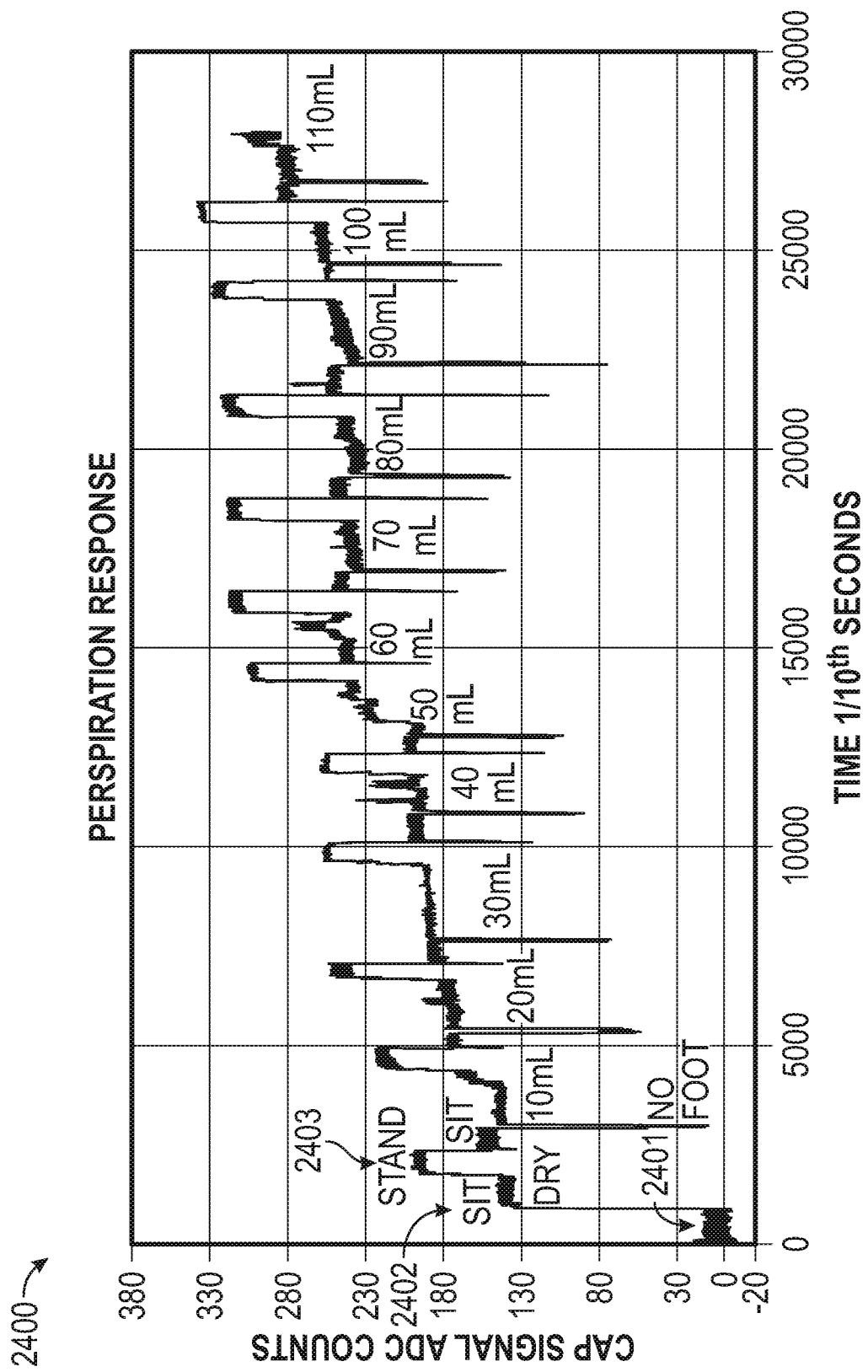
FIG. 24 illustrates generally an example of a chart that shows a relationship between sensor responses and simulated perspiration.

FIG. 24 illustrates generally an example of a chart 2400 that shows a relationship between a capacitive sensor response and changes in a fluid saturation of one or more components of footwear that includes the capacitive sensor. The example of chart 2400 illustrates the effects of simulated perspiration applied to an ankle of a foot wearing a sock and disposed inside of an article of footwear that includes a capacitive sensor. The example corresponds to a test performed wherein the output of the capacitive sensor was monitored over time, and over multiple sit/stand cycles, as a perspiration proxy is added to the test assembly.

The test assembly included a foot outfitted with a sock and footwear that includes a foot presence sensor according to one or more embodiments discussed herein. Perspiration was simulated by introducing a saline solution to the ankle area of the foot. Approximately 10 milliliters of saline solution was added at each test interval, such as at the intervals indicated in the chart 2400 of FIG. 24. The volumetric labels indicate a cumulative total amount of solution added.

The example of FIG. 24 begins with a brief first interval 2401 wherein no foot is present in the footwear. During the first interval 2401, the capacitive sensor output is substantially zero counts. During a second interval 2402, a foot is present in the footwear and is substantially dry, and the count output from the sensor registers a non-zero baseline or reference value (e.g., about 140 counts). During a third interval 2403, the wearer stands, thereby further increasing the count output from the sensor (e.g., to about 200 counts). Following the third interval 2403, multiple sit/stand cycles are performed in series, with an addition of simulated perspiration or saline at each cycle.

The example of FIG. 24 indicates generally that perspiration or moisture can have affect an output count from a capacitive sensor. For example, a baseline or reference count value when the test assembly is dry and the test subject is seated (e.g., corresponding to the second interval 2402) can be less than a baseline or reference count value when the test assembly is damp (e.g., partially saturated) and the test subject is seated. In the example of FIG. 24, the test assembly was substantially saturated after about 60 milliliters of simulated perspiration was added. Accordingly there can be observed a relative incline of baseline or reference count values between about zero and 60 milliliters of fluid added, however, the baseline or reference count is relatively unchanged as more liquid is added over 60 milliliters.

Although the baseline or reference condition changes for sit and stand configurations over different levels of fluid saturation, a count difference between adjacent sit durations (e.g., shown as plateaued valleys) and stand durations (e.g., shown as plateaued peaks) is substantially the same for any amount of simulated perspiration or saturation. For example, a first count difference between the second and third intervals 2402 and 2403, or under dry conditions, is observed from FIG. 24 to be about 60 counts. A count difference between sit and stand intervals under saturated conditions, such as at the indication of 70 mL on the chart 2400, is observed to be about 75 counts, or only about 15 counts different than is observed under dry or non-saturated conditions. Thus in the presence of changing baseline or reference capacitance conditions, information about footwear usage can be determined from the sensor, including information about a presence or absence of a foot, or information about a force exerted on the sensor such as a foot strike force, which information can be used to discriminate between sitting and standing postures.

Figure 25:
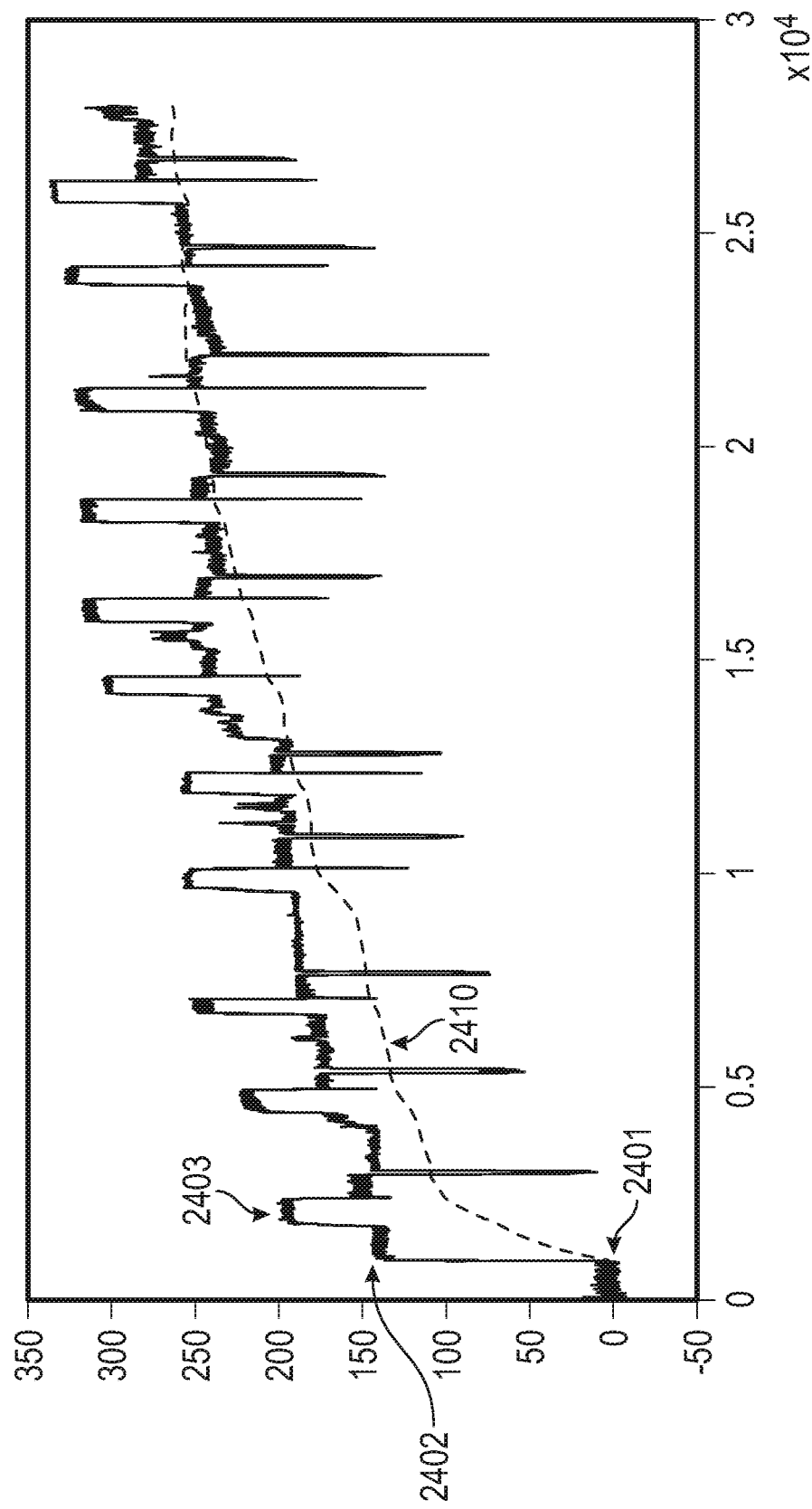
FIG. 25 illustrates generally an example of a chart that shows a relationship between sensor responses and simulated perspiration with an averaged signal.

FIG. 25 illustrates generally an example of the chart from FIG. 24 that shows a relationship between sensor responses and simulated perspiration with an averaged signal. In the example of FIG. 25, an average curve 2410, calculated as a slow-moving average of the sensor count, is imposed on the chart 2400 from the example of FIG. 24. The average curve 2410 can correspond to a changing reference capacitance value over time, and can be used as a reference in identifying foot presence in or absence from the footwear. For example, if a wearer removes his or her foot from the footwear, then a subsequent sensor output comparison can be performed using the absolute reference indicated by the average curve 2410, such as instead of relying on or using relative sensor information, such as from a prior footwear occupancy by the same or different wearer. That is, information about a changing reference condition for a capacitive sensor, such as corresponding to changes in moisture in or around the sensor or its target, can be used to adjust a threshold for use in determining, among other things, whether a foot is present in, or absent from, footwear.

Figure 26:
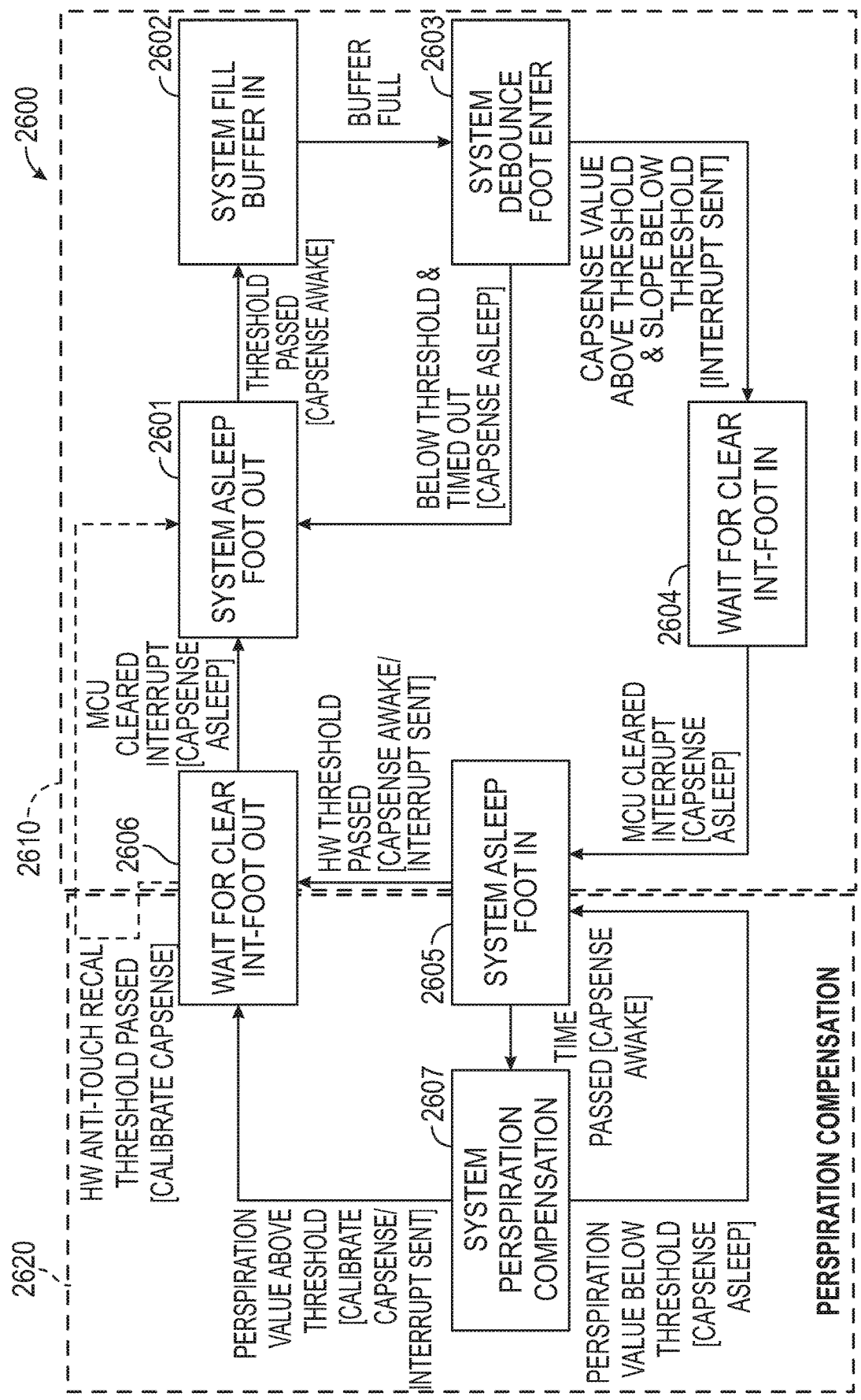
FIG. 26 illustrates generally an example of a state diagram for a perspiration compensation method.

FIG. 26 illustrates generally an example of a state diagram 2600 for a perspiration compensation method. The state diagram 2600 includes a first block 2610 of states and a second block 2620 of states. The first block 2610 represents basic foot presence detection functions of the system. The second block 2620 represents a compensation function that can optionally be used to augment automated footwear operations, such as by updating a baseline or reference characteristic for a foot presence sensor in the footwear.

The example can begin at state 2601 wherein a footwear system that includes a foot presence sensor can be in a resting, asleep, or inactive state, such as when a foot is not present in the footwear or a foot is not near the foot presence sensor in the footwear. Sensor activity can be monitored by a processor circuit, for example according to a specified duty cycle or in response to a command from a user. When the sensor indicates a nonzero or non-baseline response, then the processor circuit can wake other circuitry to determine whether the nonzero response indicates a foot presence or noise. For example, as the footwear is donned and a capacitive sensor registers other than a reference or baseline capacitance, a specified capacitance threshold can be met or exceeded, thereby awakening further processing to validate whether a foot is present in the footwear or not.

At state 2602, the example includes filling a memory buffer with sensor data. The data collected can be sufficient to make a determination about a presence or absence of a foot, or about discrimination of a foot presence signal from noise. When the buffer has a specified amount of data (e.g., corresponding to a specified number of samples, or counts, or a specified duration), then at state 2603 the system can perform a "debounce" analysis to determine whether a foot is present or not. The debounce analysis can include, among other things, signal smoothing, averaging, time delay, or other processing to help discriminate signal noise from usable foot presence information.

The debounce analysis can include monitoring capacitance-indicating signal changes and discerning a velocity characteristic from the capacitance-indicating signal. In an example, the debounce analysis includes monitoring the velocity characteristic to ascertain when a foot is partially or fully seated with respect to the footwear's footbed. When the capacitance-indicating signal settles to a substantially constant value or steady-state value, then the foot can be considered to be sufficiently seated and thereby the system can trigger one or more other functions of the automated footwear, such as an automatic lacing function or a data collection function.

In the example of FIG. 26, the debounce analysis includes "capsense value above threshold and slope below threshold". "Capsense value above threshold" indicates that a capacitance-indicating signal from a capacitive foot presence sensor registers a value that exceeds a references or baseline capacitance value. "Slope below threshold" indicates that a rate of change of the capacitance-indicating signal from the sensor is less than a specified reference or baseline rate of change value, for example indicating that the foot is present in the footwear but is substantially still relative to the sensor. When both conditions are met, an interrupt can be provided to one or more other processors or devices to thereby trigger the one or more other functions of the footwear.

That is, from state 2603, the system can determine one of (1) the nonzero response represents noise or times out before a positive foot presence indication, and (2) the nonzero response indicates a valid foot presence signal. For (1), the system returns to state 2601 and resumes a low power monitoring state. For (2), the system proceeds to state 2604. In proceeding to state 2604, the system verified that the sensor response exceeds a specified threshold value and, in some examples, that a signal slope characteristic meets or exceeds a specified slope criteria. As indicated in FIG. 26, an interrupt based on a foot presence determination can be sent to one or more processors, circuits, or devices, such as to initiate another activity or process when the foot is determined to be present. For example, the interrupt can be used by a lacing engine to initiate an automated lacing procedure or hardware process. At state 2604, the system maintains a state that includes a positive foot presence indication, and the system can be configured to wait for another signal or interrupt to initiate or perform a subsequent process.

From state 2604, the system can enter a relatively low power or sleep state 2605, wherein the system can hold for further data or detected changes in the sensor signal. In an example, state 2605 represents a state wherein a foot is present in the shoe and the shoe is actively used or worn. For example, if footwear is automatically laced and secured to a foot based on a foot presence determination from the debounce analysis at state 2603, then at state 2605 the footwear can be maintained in a secured state about the foot, while periodically monitoring the sensor status or waiting for another interrupt to change a state of the footwear. In an example, monitoring a capacitance-indicating signal from a foot presence sensor at state 2605 includes monitoring the signal at a relatively low frequency, such as 1-2 Hz or less, to identify whether the capacitance-indicating signal changes by more than a threshold amount.

In an example, if the signal indicates more than a threshold change amount, then the state machine proceeds to state 2606 where a foot presence-indicating interrupt can be cleared. In an example, proceeding to state 2606 can include a hardware or software check to determine whether a baseline or reference characteristic of the sensor should be updated. For example, the notation "HW Anti-touch Recal Threshold Passed" indicates an automated recalibration process. If a foot is removed and, in state 2606, the capacitance-indicating foot presence signal is below a specified threshold, then a new reference or baseline can be established. The new reference or baseline can be used for further detection activities such as from state 2601.

Various changes in the footwear itself, such as during a course of footwear use, can cause the sensor signal to indicate a foot presence when a foot is in fact absent from the footwear. For example, fluid saturation or wetness of one or more components of the footwear, such as due to perspiration, can influence a capacitance-indicating signal from a capacitive sensor and can cause a false indication that a foot is present in the footwear. Accordingly, at state 2605, the system can be configured to periodically wake or perform an analysis and compensation routine to verify whether a foot is present in the footwear.

In the example of FIG. 26, the compensation routine can include a timed data collection and analysis from the capacitive sensor. For example, following state 2605, a compensation routine at state 2607 can be triggered periodically or intermittently. In some examples, the compensation routine is performed on the order of every several minutes or hours. The compensation routine collects sensor signal data and monitors the signal for changes. If the signal includes variations that meet or exceed a specified threshold variation or change amount, then the system can determine that a foot is likely to be present in the footwear and state 2605 can be maintained. The compensation routine can be repeated after a specified duration. However, if the sensor signal is determined to be relatively silent or unchanging over the monitored interval, then the system can determine that a foot is likely to be absent from the footwear and the system can return to state 2601. In this example, the return to state 2601 includes a recalibration to determine whether a baseline or reference capacitance-indicating signal requires an update.

In an example, foot displacement information, such as relative to a sensor inside of footwear, can be determined using count information from a capacitive sensor in footwear. The slope of the displacement information can represent a velocity characteristic of the foot inside of the footwear, and in turn, can represent velocity of the footwear itself in some use cases. In an example, information about a velocity characteristic of a foot can be used to trigger one or more features of footwear. For example, a velocity profile can be used to identify a footwear donning or doffing event, which can trigger automated lacing or unlacing procedures, respectively.

Figure 27:
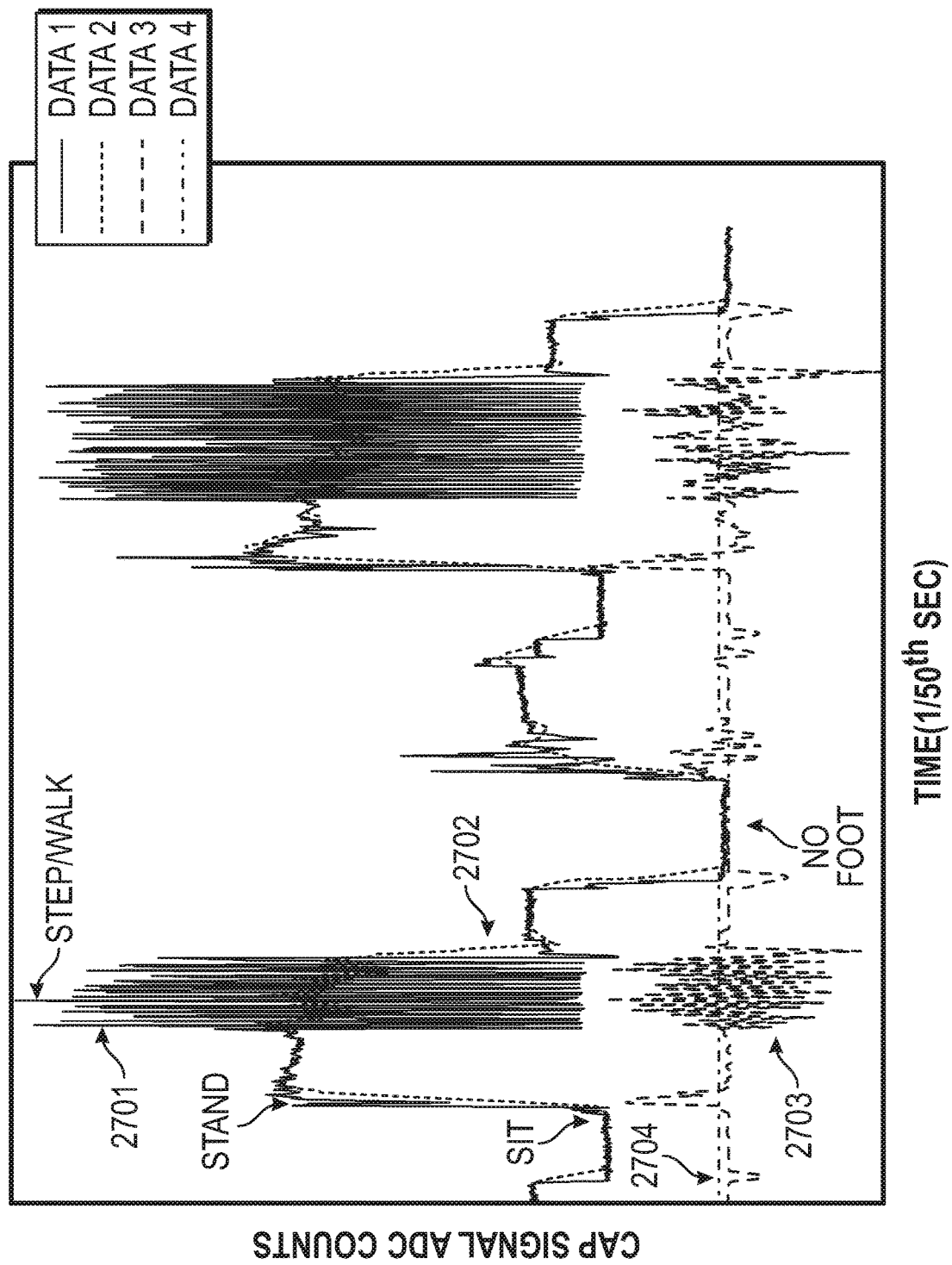
FIG. 27 illustrates generally an example of a chart that shows foot presence sensor data.

FIG. 27 illustrates generally an example of a chart that shows foot presence sensor data. The example of FIG. 27 includes a first curve 2701 (shown as a solid line) that indicates raw data sampled from a capacitive foot presence sensor. The example of FIG. 27 further includes a second curve 2702 (shown as a short-dash line) that is a filtered version of the first curve 2701. In an example, the second curve 2702 is used for foot presence detection by comparing its magnitude to a specified threshold magnitude. A foot can be indicated to be present in footwear for values of the second curve 2702 that exceed the specified threshold, and a foot can be indicated to be absent from the footwear for values of the second curve 2702 that do not exceed the specified threshold. The threshold and/or a baseline capacitance value from the sensor can be updated or changed as discussed herein.

The example of FIG. 27 includes a third curve 2703 (shown as a long-dash line). The third curve 2703 can indicate a slope of the first curve 2701, such as a slope of the first curve 2701 over a specified preceding duration. A length of the preceding duration can be adjusted or tuned based on desired performance characteristics of the sensor or system (e.g., attack time or sensitivity or immunity to noise or to rapid signal changes or signal bounce).

In an example, a magnitude of the third curve 2703 can indicate a relative velocity of the footwear that includes the sensor, or of a relative velocity of the foot inside of the footwear when the footwear is worn by the foot. A large magnitude of the third curve 2703 can correspond to a large velocity or displacement of a foot relative to the sensor in vertical (z) and horizontal (x/y) directions, and a small magnitude of the third curve 2703 can correspond to a small velocity.

The example of FIG. 27 further includes a fourth curve 2704 (shown as an alternating short/long dash line). The fourth curve 2704 indicates whether a foot is present in or is absent from the footwear. The fourth curve 2704 is thus a binary signal in the example of FIG. 27 and has two states, high and low.

In an example, a decision about whether a foot is present in or absent from the footwear can be made (e.g., by a processor circuit) using information from both the second and third curves 2702 and 2703. For example, if signal information from the second curve 2702 is less than a specified threshold signal (e.g., less than 30 counts) and is followed by a detected velocity change, then a foot presence can be indicated. In an example, the detected velocity change can be a velocity change by greater than a specified threshold velocity amount. In another example, the detected velocity change can include a velocity profile comparison, such as to compare a velocity change or waveform morphology with a known velocity change or morphology that corresponds to a foot presence.

In an example, footwear velocity or displacement information can be obtained from a separate sensor, such as an accelerometer or gyroscope that is mounted in or on the footwear. Such velocity or displacement information can optionally be used together with the information about the foot velocity relative to the sensor inside the footwear. For example, the foot velocity information can be used to determine an optimum footwear tension characteristic during footwear use, such as during sport or activity. In an example, the foot velocity information can be used to optimize the tension characteristic to be a specified tightness, such as just tight enough to stop relative movement between foot and footwear (as detected by the capacitive sensor) during a hard stop or sprint (as detected by the accelerometer or gyroscope). Conversely if no foot or footwear velocity or acceleration is detected, a tension characteristic may be determined to be excessive or unnecessary, and the footwear tension can be relaxed. For example, if a foot swells during the course of activity, then the footwear can be relaxed (e.g., laces can be loosened) until there is some specified minor velocity detected.

In an example, footwear that includes an automated lacing feature can be removed from a foot in multiple ways. For example, the footwear can include a button that can be pressed by a wearer to reduce tension in the laces and thereby make the footwear easier to remove. In some examples, a baseline or reference value of one or more sensors can be changed or updated during footwear use (e.g., due to moisture retained in the wearer's sock or due to other environmental conditions). When the button is pressed, the one or more sensors or baselines or reference values for the footwear can be reset or zeroed, such as to facilitate subsequent foot presence sensing.

In another example, footwear can be pried off. The automated lacing systems described herein can be configured to detect when footwear is pried off, for example, by detecting a foot absence using sub-threshold counts from a capacitive foot presence sensor. In an example, a foot absence can be detected in part using the count information from the capacitive sensor together with velocity information that indicates a velocity change and/or a velocity profile or morphology that corresponds to a known shoe doffing velocity profile.

FIGS. 28A-30D illustrate generally examples of a footbed assembly with a lacing engine assembly 2803, and various techniques or examples for installing or retaining the lacing engine assembly 2803 in a lacing engine cavity 2801 in the footbed. FIGS. 28A, 29A, 29B, 29C, 30B, 30C, and 30D illustrate generally examples of a user accessing the lacing engine assembly 2803 and/or the lacing engine cavity 2801, from the perspective of the user. The user's hand depicted in the figures is not essential, is not required for any embodiments, and forms no part of the present invention.

Figure 28A:
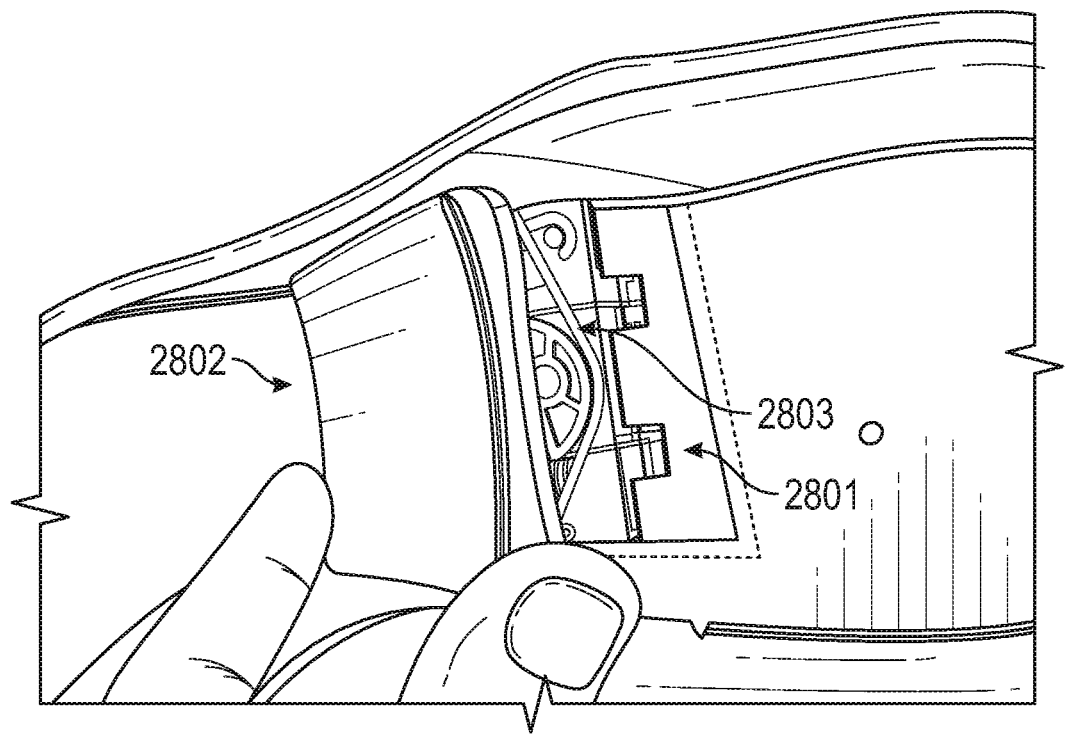
FIGS. 28A and 28B illustrate generally an example of a footbed assembly with a tonneau cover.
Figure 28B:
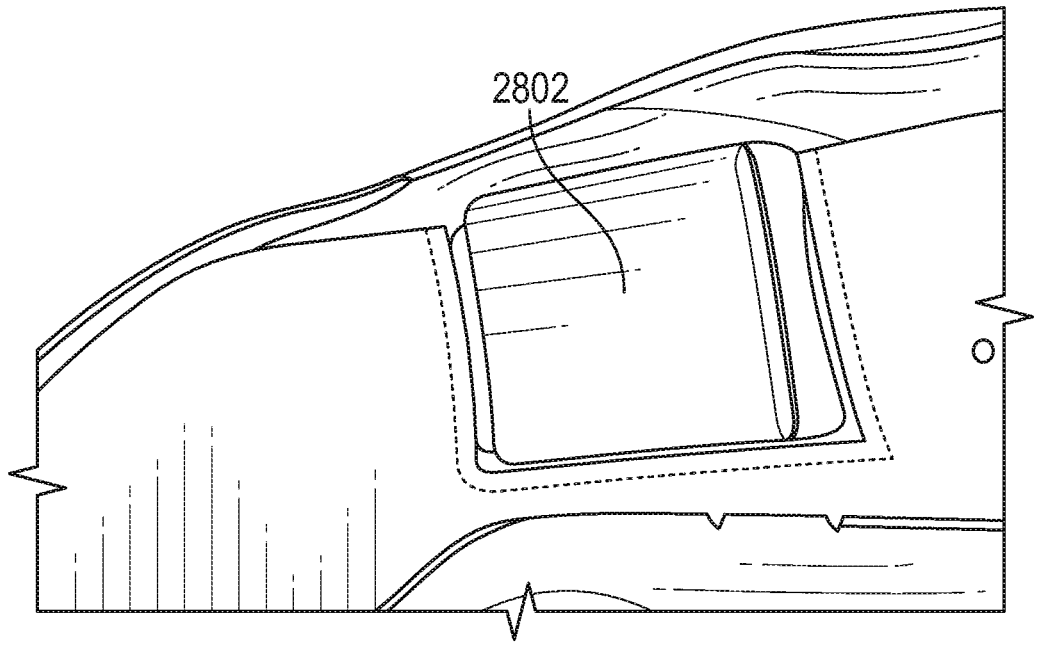

FIGS. 28A and 28B illustrate generally an example of a footbed assembly with a tonneau cover 2802. The footbed assembly can include a lacing engine cavity 2801 in which a lacing engine assembly 2803 can be installed. In the example of FIG. 28A, the tonneau cover 2802 is shown in a raised position to provide a view of the lacing engine cavity 2801 with a lacing engine assembly disposed therein. In FIG. 28B, the tonneau cover 2802 is installed and covers substantially all of the lacing engine cavity 2801.

In an example, the lacing engine assembly 2803 can include an electrode for a capacitive sensor (see, e.g., the examples of electrode assemblies in FIGS. 21A-21D, among others discussed herein). In an example, a dielectric member (e.g., neoprene or other closed or open-cell rubber or foam, EVA, or other material) can be disposed over the lacing engine assembly, and the tonneau cover 2802 can be provided over the dielectric member. In an example, the tonneau cover 2802 can be contoured to an arch of a wearer's foot. In an example, the tonneau cover 2802 is arched or umbrella-shaped to help divert moisture away from the lacing engine assembly 2803. The tonneau cover 2802 can comprise various rigid or compliant materials, such as including carbon fiber, EVA, or neoprene rubber, and can be configured to be relatively conducting to thereby enhance body sensing sensitivity of an underlying capacitive sensor. Thus the tonneau cover 2802 can provide a protective covering for a lacing engine assembly 2803 and in some examples can augment a foot sensing capability.

FIGS. 29A-29D illustrate generally an example of a footbed assembly with a first hook and loop cover for the lacing engine cavity 2801. The cover is provided between the lacing engine assembly 2803 and a foot-receiving surface of the footwear. The cover provides various functions such as retention of the lacing engine assembly 2803 in the lacing engine cavity 2801, and mechanical biasing of one or more other materials in, or adjacent to, a portion of a dielectric stack above the lacing engine assembly 2803 to an uncompressed or less-compressed state, particularly when the footwear is vacant. In an example, the hook and loop cover provides a suspension mechanism that can be used to reduce stress on or decompress a dielectric stack provided over the lacing engine assembly 2803. That is, the cover can bias the dielectric stack toward an uncompressed state.

Figure 29A:
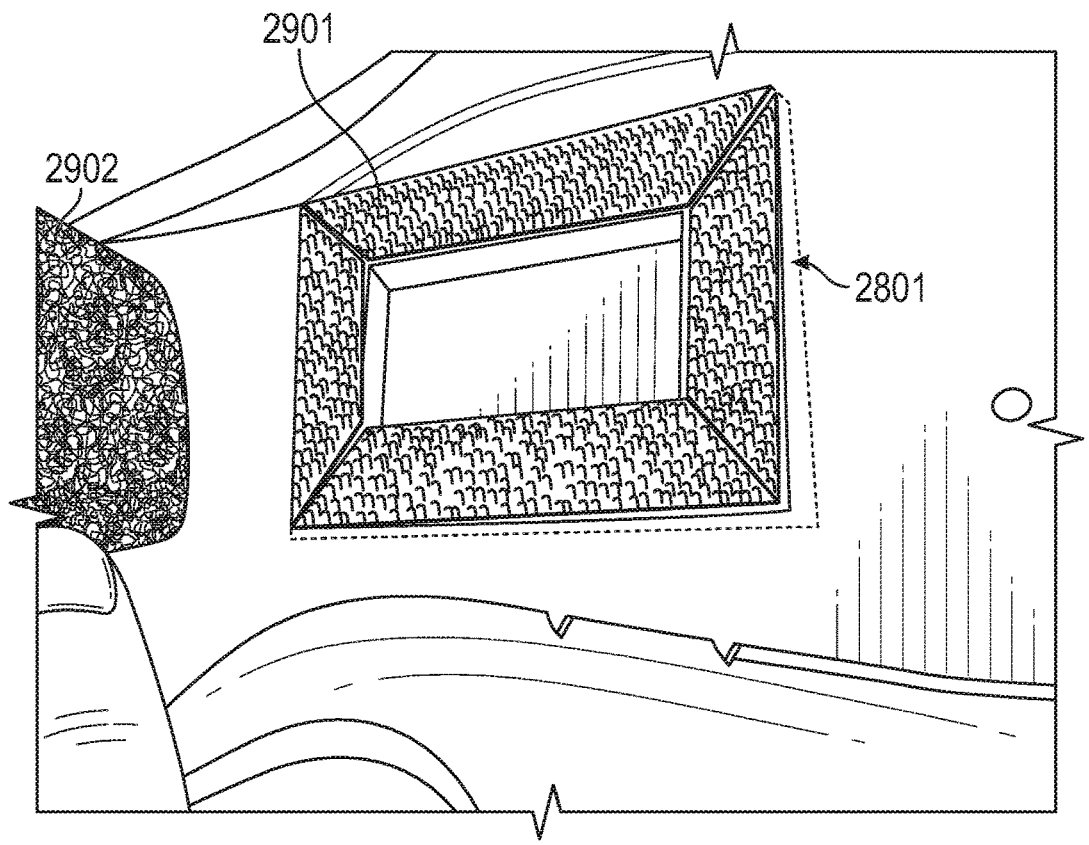
FIGS. 29A-29D illustrate generally an example of a footbed assembly with a first hook and loop cover for a lacing engine.
Figure 29B:
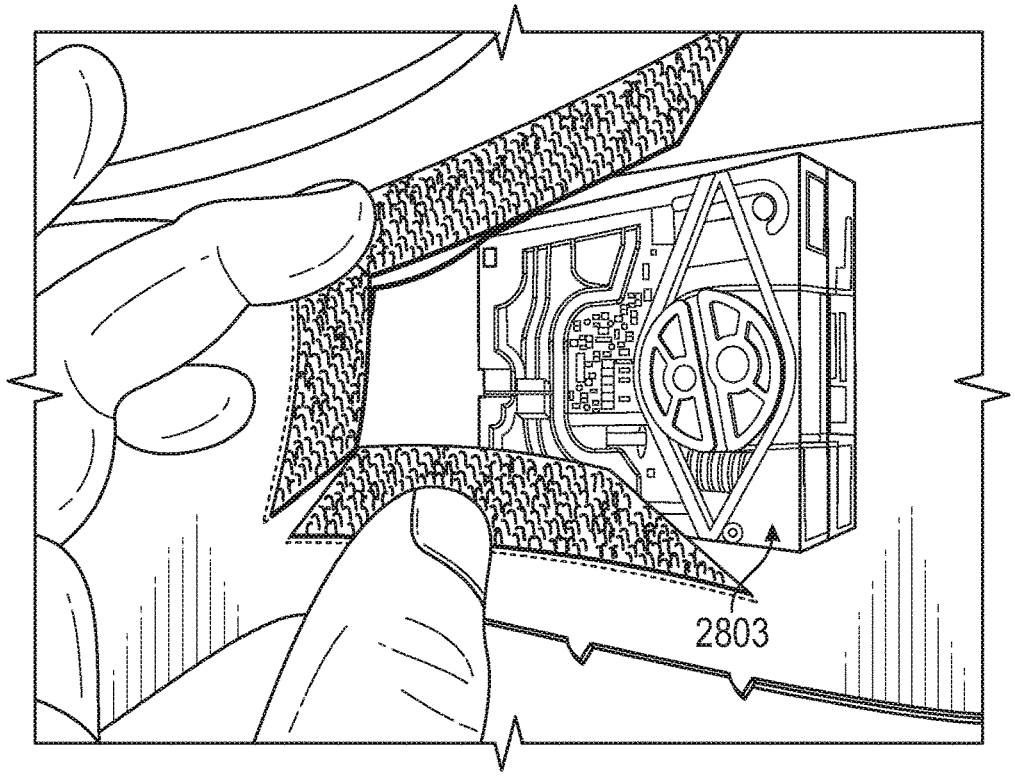
Figure 29C:
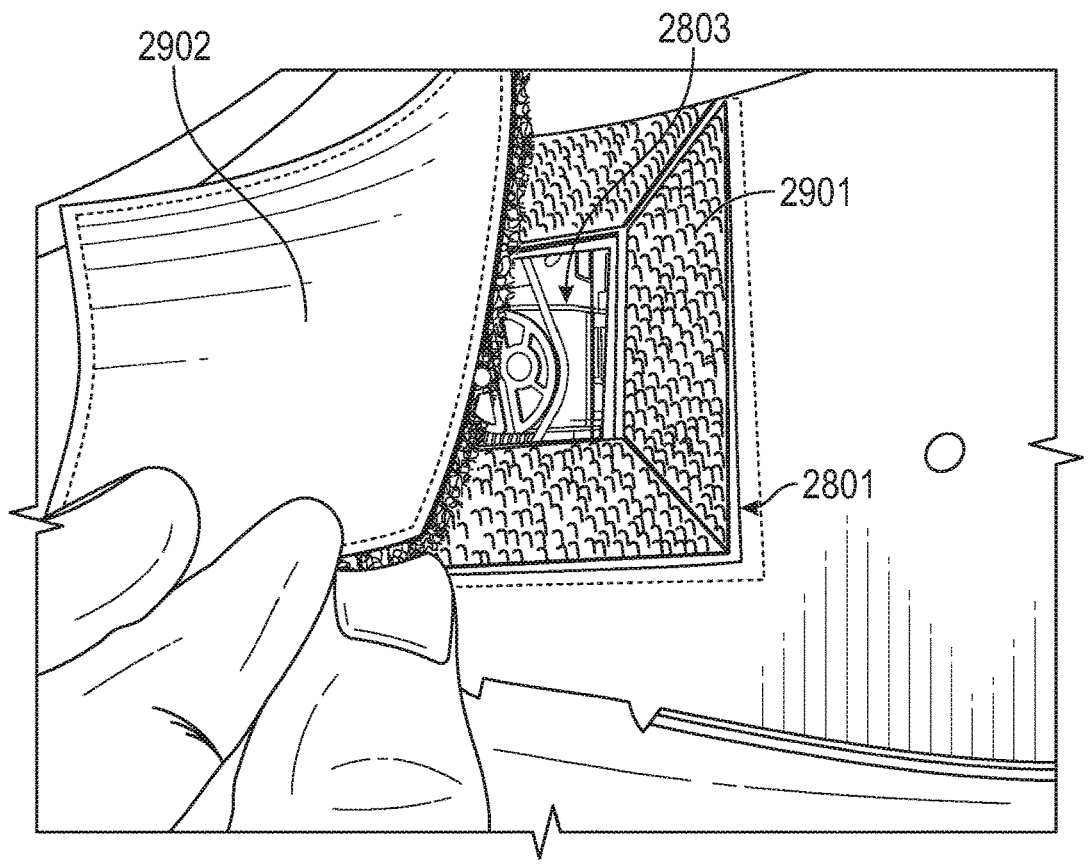
Figure 29D:
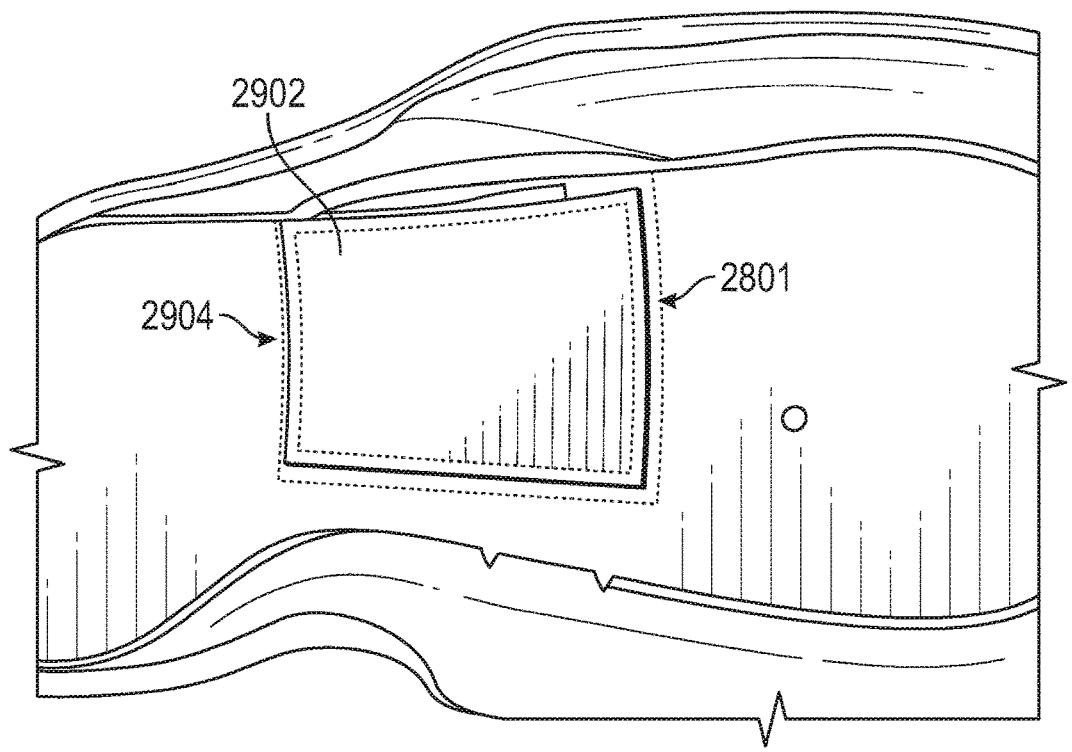

In the example of FIG. 29A, the first hook and loop cover includes a hook perimeter portion 2901 that follows a perimeter of a lacing engine cavity 2801 in the footbed. Outer side edges of the hook perimeter portion 2901 can be secured to one or more edges of the lacing engine cavity 2801, and inner side edges of the hook perimeter portion 2901 can be flexible and can be manually raised to accommodate insertion of a lacing engine assembly 2803 into the cavity. The lacing engine assembly 2803 can be covered using a loop material cover 2902. The loop material cover 2902 can help retain the lacing engine assembly 2803 inside of the lacing engine cavity 2801 in the footbed. In some examples, the loop material cover 2902 includes an outer facing side that is hydrophobic and is configured to help divert moisture away from the lacing engine.

Figure 30A:
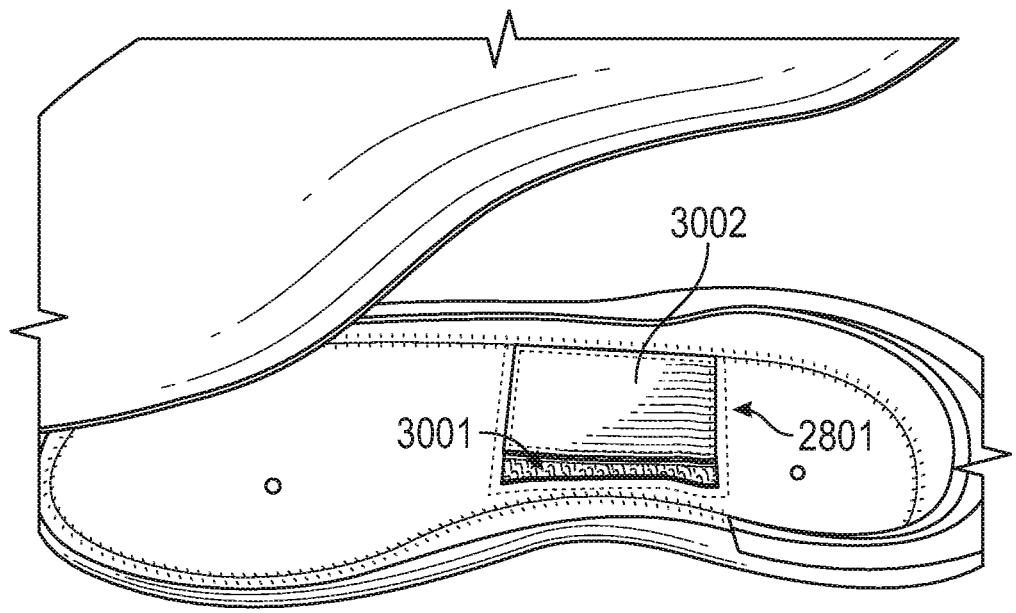
FIGS. 30A-30D illustrate generally an example of a footbed assembly with a second hook and loop cover for a lacing engine.
Figure 30B:
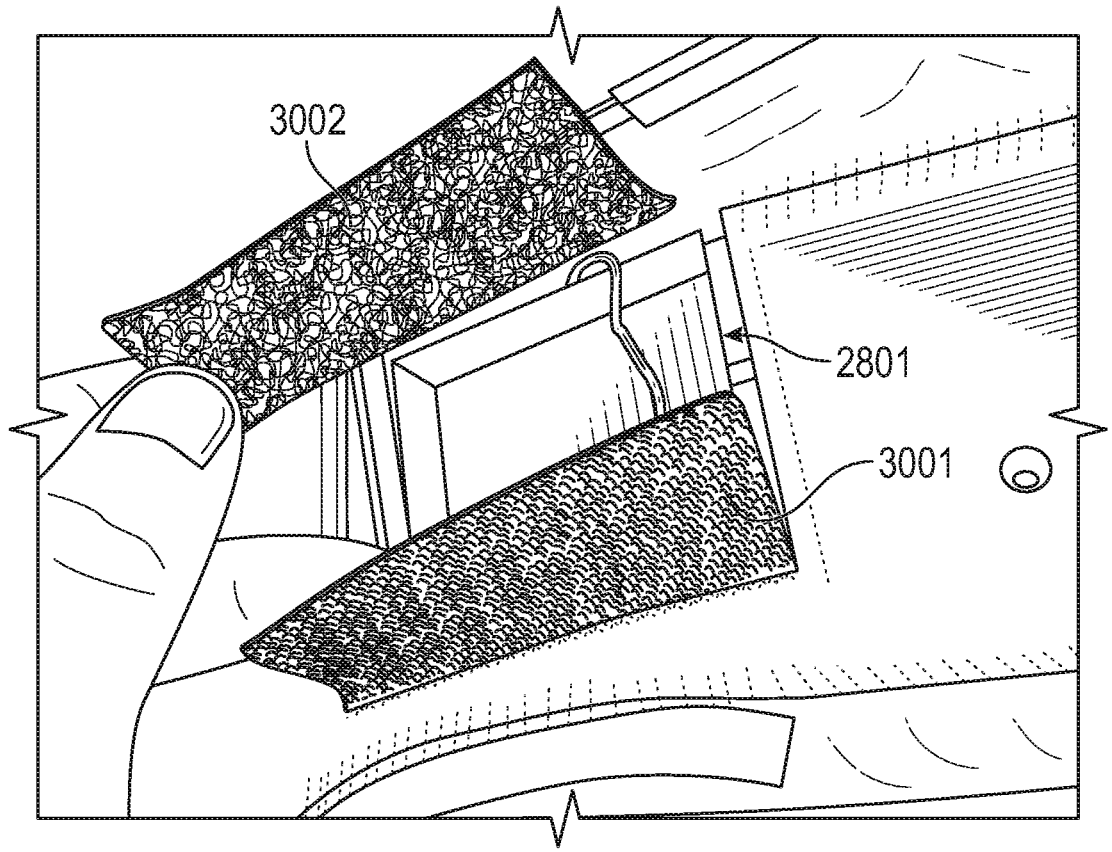
Figure 30C:
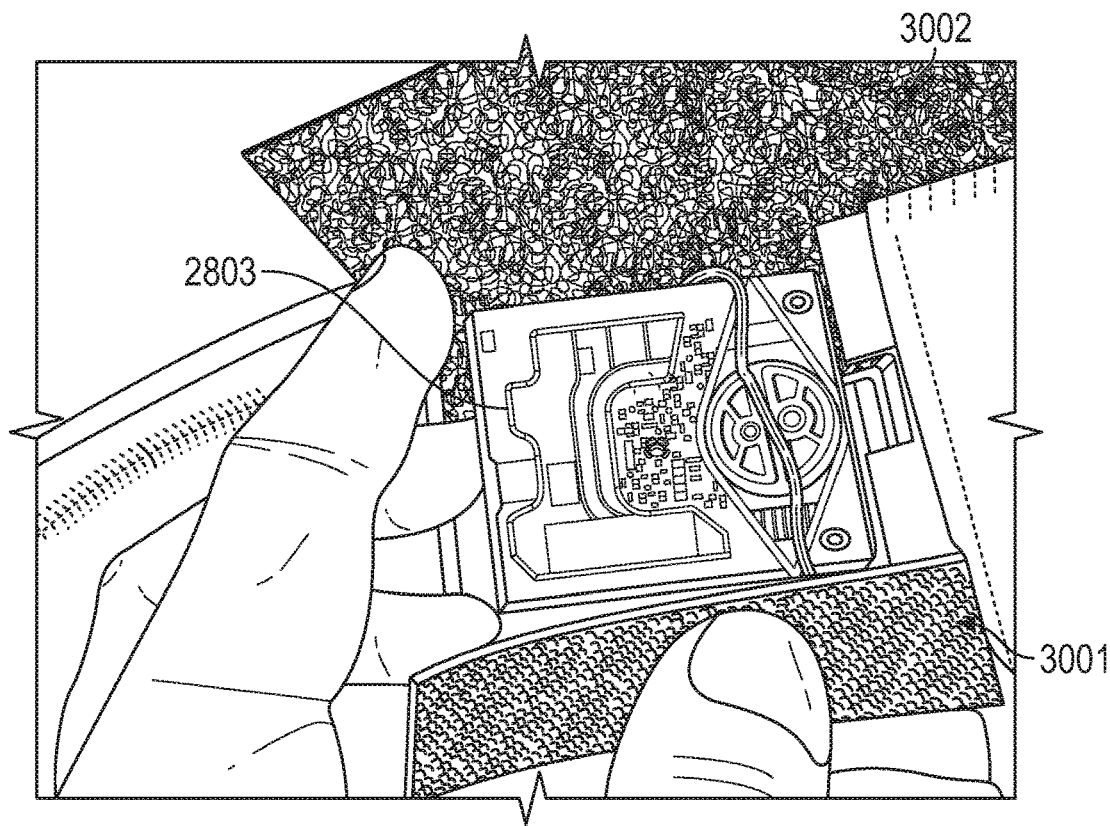

FIGS. 30A-30D illustrate generally an example of a footbed assembly with a second hook and loop cover for a lacing engine assembly. In the example of FIG. 30A, hook and loop material covers 3001 and 3002 cover the lacing engine cavity 2801 in the footbed. In FIG. 30B, the hook cover 3001 follows first side edges of the lacing engine cavity 2801 in the footbed. A side edge of the hook material cover 3001 can be coupled to the footbed at a first side of the lacing engine cavity 2801, and can be flexible and can be manually raised to accommodate insertion of the lacing engine assembly 2803 into the lacing engine cavity 2801 (see, e.g., FIG. 30C). A side edge of the loop material cover 3002 can be coupled to the footbed at an opposite second side of the lacing engine cavity 2801 such that the hook and loop material covers 3001 and 3002 at least partially overlap and couple with each other.

Figure 30D:
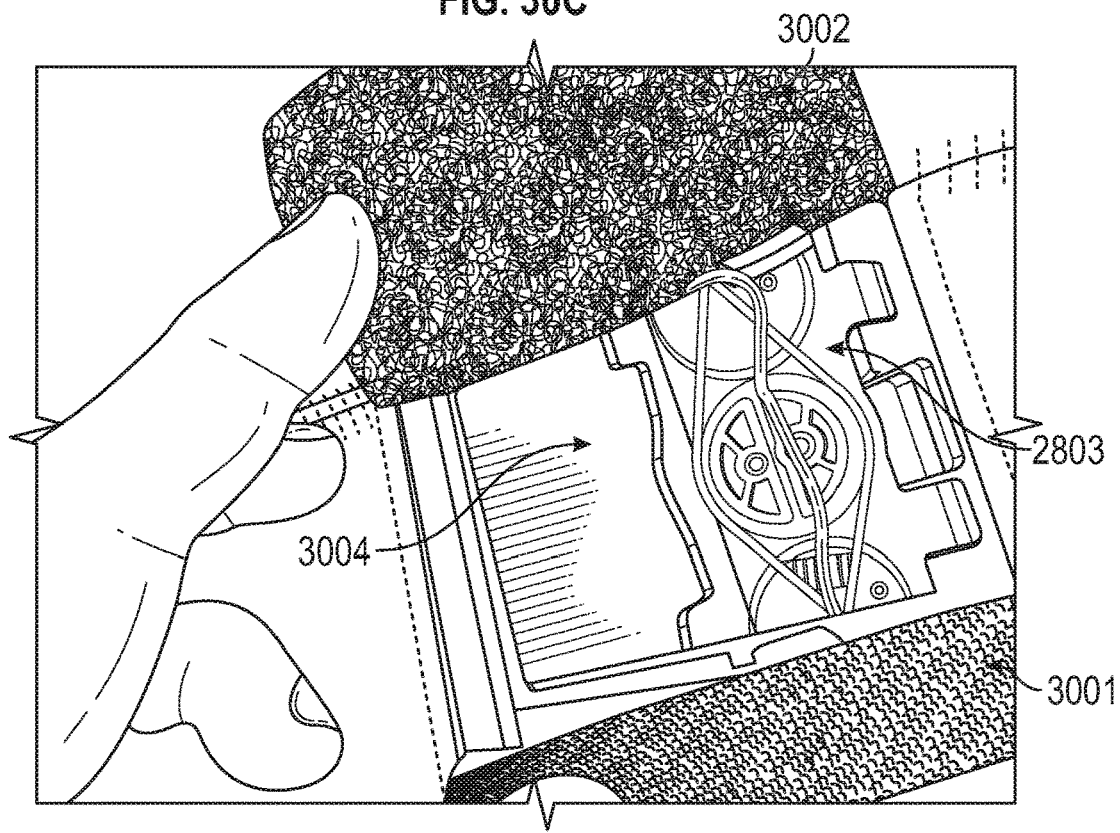

One or more members of a dielectric stack 3004 can be provided adjacent to or on top of a portion of the lacing engine assembly 2803. In the example of FIG. 30D, the dielectric stack 3004 includes a neoprene layer or doped EVA layer provided adjacent to an electrode assembly inside of the housing of the lacing engine assembly 2803. The lacing engine assembly 2803 with dielectric stack 3004 can be covered using the hook and loop material covers 3001 and 3002, as shown in FIG. 30A. The hook and loop material covers 3001 and 3002 can be configured to retain the lacing engine assembly 2803 inside of the lacing engine cavity 2801 in the footbed. In some examples, an upper one of the hook and loop material covers 3001 and 3002 includes an outer (foot-facing) side that is hydrophobic and is configured to help divert moisture away from the lacing engine assembly 2803.

In the example of FIG. 30D, the dielectric stack 3004 overlies a portion of the housing of the lacing engine assembly 2803. A gap filler, such as a polyurethane or other foam or compressible member can be inserted to cover a remaining or other portion of the housing so as to provide a relatively seamless and comfortable surface underfoot for the user. The gap filler can be substantially transparent to electric fields monitored by a capacitive foot presence sensor in the lacing engine assembly 2803. In other words, the gap filler material can be selected to minimize an impact or influence on a foot presence-indicating signal from a capacitive foot presence sensor that is in or coupled to the lacing engine assembly 2803.

The hook and loop assemblies in the examples of FIGS. 29A-29D and FIGS. 30A-30D can be configured to help absorb and distribute foot impact forces, such as away from the lacing engine assembly 2803, and yet can be substantially transparent to fields used by a capacitive sensor inside (or adjacent to) the lacing engine assembly 2803 to monitor or detect a foot presence in or absence from the footwear. In an example, the various hook and loop assemblies or tonneau covers discussed herein can be configured to provide an outward or upward mechanical bias away from the dielectric stack 3004, such as to reduce effects of repeated compression of the dielectric stack 3004 due to footwear use, and thereby maintain foot presence sensing signal sensitivity, fidelity and dynamic range over the course of repeated or prolonged footwear use.

The following aspects provide a non-limiting overview of the footwear, capacitive sensors, capacitive sensor signal processing, and velocity-related signal processing discussed herein.

Aspect 1 can include or use subject matter (such as an apparatus, a system, a device, a method, a means for performing acts, or a device readable medium including instructions that, when performed by the device, can cause the device to perform acts), such as can include or use a method comprising receiving a time-varying sensor signal from a sensor that is coupled to an article of footwear, wherein the sensor is configured to sense information about a proximity of a foot to the sensor, and using a processor circuit, identifying a velocity characteristic of the foot relative to the sensor using the time-varying sensor signal. In an example, Aspect 1 can include, based on the velocity characteristic as identified, initiating data collection about the footwear or about the proximity of the foot to the sensor using the same or different sensor coupled to the footwear. In an example, Aspect 1 can include, based on the velocity characteristic as identified, updating an automated function of the footwear. Updating the automated function of the footwear can include initiating or inhibiting an automated lacing function of the footwear, such as to secure the footwear to a foot or to release the footwear from the foot.

Aspect 2 can include or use, or can optionally be combined with the subject matter of Aspect 1, to optionally include identifying the velocity characteristic of the time-varying sensor signal, including using displacement information about a location of the foot relative to the sensor.

Aspect 3 can include or use, or can optionally be combined with the subject matter of Aspect 2, to optionally include using the processor circuit, determining whether a foot is present in the article of footwear based on the velocity characteristic as identified.

Aspect 4 can include or use, or can optionally be combined with the subject matter of one or any combination of Aspects 2 or 3 to optionally include using the processor circuit, determining a step count using the velocity characteristic as identified.

Aspect 5 can include or use, or can optionally be combined with the subject matter of one or any combination of Aspects 2 through 4 to optionally include using the processor circuit, determining a foot strike force characteristic using the velocity characteristic as identified.

Aspect 6 can include or use, or can optionally be combined with the subject matter of Aspect 1, to optionally include the identifying the velocity characteristic using the time-varying sensor signal includes, using the processor circuit (1) identifying first portions of the time-varying sensor signal corresponding to a foot strike and identifying other second portions of the time-varying sensor signal corresponding to a foot lift, and (2) determining a step count, a rate of travel, or a distance of travel, using information about timings of the first and second portions of the time-varying sensor signal.

Aspect 7 can include or use, or can optionally be combined with the subject matter of Aspect 1, to optionally include the identifying the velocity characteristic using the time-varying sensor signal includes, using the processor circuit (1) identifying first portions of the time-varying sensor signal corresponding to a foot strike and identifying other second portions of the time-varying sensor signal corresponding to a foot lift, and (2) determining a lifecycle status of an insole component of the footwear using at least the first portions of the time-varying sensor signal.

Aspect 8 can include or use, or can optionally be combined with the subject matter of Aspect 7, to optionally include the determining the lifecycle status of the insole component includes identifying a peak-to-peak excursion characteristic of the time-varying sensor signal.

Aspect 9 can include or use, or can optionally be combined with the subject matter of one or any combination of Aspects 7 or 8 to optionally include reporting a footwear status indication to a user when the lifecycle status as determined indicates the insole provides insufficient cushioning to the user.

Aspect 10 can include or use, or can optionally be combined with the subject matter of one or any combination of Aspects 1 through 9 to optionally include the updating an automated function of the footwear includes initiating or inhibiting operation of an automatic lacing engine, wherein the lacing engine is configured to tighten or loosen the footwear about the foot.

Aspect 11 can include or use, or can optionally be combined with the subject matter of one or any combination of Aspects 1 through 10 to optionally include the receiving the time-varying sensor signal from the sensor includes receiving a time-varying capacitance-indicating signal from a capacitive sensor.

Aspect 12 can include or use, or can optionally be combined with the subject matter of Aspect 11, to optionally include the receiving the time-varying capacitance-indicating signal from the capacitive sensor includes providing a drive signal to a driven shield that is configured for use with the capacitive sensor.

Aspect 13 can include or use, or can optionally be combined with the subject matter of one or any combination of Aspects 11 or 12 to optionally include using the processor circuit, intermittently monitoring the time-varying capacitance-indicating signal from the capacitive sensor over a specified duration and, when the signal indicates less than a specified threshold signal change over the specified duration, updating a reference capacitance characteristic of the capacitive sensor.

Aspect 14 can include or use, or can optionally be combined with the subject matter of Aspect 13, to optionally include or use updating the reference capacitance characteristic includes using a moving average of an output from the capacitive sensor.

Aspect 15 can include or use, or can optionally be combined with the subject matter of Aspect 13, to optionally include identifying a later subsequent velocity characteristic of the foot relative to the sensor using the time-varying sensor signal and the reference capacitance characteristic as updated.

Aspect 16 can include or use, or can optionally be combined with the subject matter of one or any combination of Aspects 1 through 15 to optionally include adjusting the velocity characteristic as identified based on a detected lifecycle status change of one or more components of the footwear.

Aspect 17 can include or use, or can optionally be combined with the subject matter of one or any combination of Aspects 1 through 16 to optionally include the receiving the time-varying sensor signal includes while a foot is inserted or removed from the footwear, and wherein the identifying the velocity characteristic of the time-varying sensor signal includes identifying a changing proximity characteristic of the foot as toe, arch, and heel portions of the foot approach the sensor in the footwear.

Aspect 18 can include or use subject matter (such as an apparatus, a system, a device, a method, a means for performing acts, or a device readable medium including instructions that, when performed by the device, can cause the device to perform acts), such as can include or use a foot proximity sensor system for footwear, the system comprising a capacitive proximity sensor coupled to an article of footwear and configured to provide a time-varying sensor signal indicating a proximity of a foot to the sensor, and a processor circuit coupled to the proximity sensor. In Aspect 18, the processor circuit can be configured to identify a velocity characteristic using the time-varying sensor signal and, based on the velocity characteristic as identified, at least one of (1) initiate data collection about the footwear or about a location of the foot relative to the sensor, using the same proximity sensor or using a different sensor coupled to the footwear, and (2) update an automated function of the footwear. In an example, updating the automated function of the footwear includes initiating or inhibiting an automated lacing function of the footwear.

Aspect 19 can include or use, or can optionally be combined with the subject matter of Aspect 18, to optionally include or use the capacitive proximity sensor comprises a planar electrode and a driven shield provided at or near an insole of the footwear.

Aspect 20 can include or use, or can optionally be combined with the subject matter of Aspect 19, to optionally include the processor circuit configured to determine one or more of a step count, a foot strike force, and a rate of travel using the velocity characteristic as identified.

Aspect 21 can include or use, or can optionally be combined with the subject matter of one or any combination of Aspects 18 through 20 to optionally include the processor circuit configured to update a reference characteristic of the capacitive proximity sensor to accommodate a change in a fluid saturation of one or more components of the footwear.

Aspect 22 can include or use, or can optionally be combined with the subject matter of one or any combination of Aspects 18 through 21 to optionally include or use a dielectric stack provided between the capacitive proximity sensor and a foot-receiving surface of the footwear.

Aspect 23 can include or use, or can optionally be combined with the subject matter of Aspect 22, to optionally include or use a cover, such as a hook and loop cover, provided between the capacitive proximity sensor and a foot-receiving surface of the footwear, and the hook and loop cover is configured to bias the dielectric stack toward an uncompressed state.

Aspect 24 can include or use subject matter (such as an apparatus, a system, a device, a method, a means for performing acts, or a device readable medium including instructions that, when performed by the device, can cause the device to perform acts), such as can include or use an automated footwear system for use in a footwear article, the system comprising a lacing engine and a lacing engine housing configured to be disposed in the article, a processor circuit provided in the housing, and a capacitive sensor, including at least one electrode and corresponding driven shield provided at least partially inside of the housing, wherein the capacitive sensor is configured to sense changes in proximity of a body to the at least one electrode and provide a time-varying sensor signal indicative of the proximity of the body to the electrodes. In an example, in Aspect 24, the processor circuit is configured to identify a velocity characteristic using the time-varying sensor signal, and based on the velocity characteristic as identified, at least one of (1) initiate data collection about the footwear or about the proximity of the body to the electrodes, using the same capacitive sensor or using a different sensor coupled to the footwear, and (2) update an automated function of the lacing engine, such as to initiate or inhibit an automated lacing function of the footwear.

Aspect 25 can include or use, or can optionally be combined with the subject matter of Aspect 24, to optionally include the processor circuit is configured determine one or more of a step count, a foot strike force, or a rate of travel using the velocity characteristic as identified.

Aspect 26 can include or use, or can optionally be combined with the subject matter of one or any combination of Aspects 24 or 25 to optionally include the processor circuit is configured to update a reference characteristic of the capacitive sensor based on a detected change in a fluid saturation of one or more components disposed in or coupled to the footwear.

Aspect 27 can include or use, or can optionally be combined with the subject matter of one or any combination of Aspects 24 through 26 to optionally include or use a dielectric stack provided on a foot-facing side of the capacitive sensor and configured to augment a sensitivity of the capacitive sensor to the body. In an example, the dielectric stack comprises a neoprene or doped EVA material.

Aspect 28 can include or use, or can optionally be combined with the subject matter of one or any combination of Aspects 24 through 27 to optionally include or use a suspension member configured to bias the dielectric stack away from a compressed state.

Aspect 29 can include or use, or can optionally be combined with the subject matter of one or any combination of Aspects 24 through 28 to optionally include or use the processor circuit configured to update the automated function of the lacing engine, including to activate an automatic lacing function of the footwear based on the velocity characteristic as identified.

Various Notes

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method comprising:
receiving a time-varying sensor signal from a sensor that is coupled to an article of footwear, wherein the sensor is configured to generate an electric field in the footwear and sense information about a change in the electric field in response to a change in proximity of a foot to the sensor; and
using a processor circuit:
identifying a velocity characteristic of the foot relative to the sensor using the time-varying sensor signal; and
based on the velocity characteristic as identified, at least one of:
initiating data collection about the footwear or about the proximity of the foot to the sensor using the same or different sensor coupled to the footwear, and
updating an automated function of the footwear.

2. The method of claim 1, wherein the identifying the velocity characteristic of the time-varying sensor signal includes using displacement information about a location of the foot relative to the sensor.

3. The method of claim 1, wherein the identifying the velocity characteristic using the time-varying sensor signal includes, using the processor circuit:
identifying first portions of the time-varying sensor signal corresponding to a foot strike and identifying other second portions of the time-varying sensor signal corresponding to a foot lift; and
determining a step count, a rate of travel, or a distance of travel, using information about timings of the first and second portions of the time-varying sensor signal.

4. The method of claim 1, wherein the identifying the velocity characteristic using the time-varying sensor signal includes, using the processor circuit:
identifying first portions of the time-varying sensor signal corresponding to a foot strike and identifying other second portions of the time-varying sensor signal corresponding to a foot lift; and
determining a lifecycle status of an insole component of the footwear using at least the first portions of the time-varying sensor signal.

5. The method of claim 2, further comprising using the processor circuit, determining whether a foot is present in the article of footwear based on the velocity characteristic as identified.

6. The method of claim 2, further comprising using the processor circuit, determining a step count using the velocity characteristic as identified.

7. The method of claim 4, wherein the determining the lifecycle status of the insole component includes identifying a peak-to-peak excursion characteristic of the time-varying sensor signal.

8. The method of claim 4, further comprising reporting a footwear status indication to a user when the lifecycle status as determined indicates the insole provides insufficient cushioning to the user.

9. A foot proximity sensor system for footwear, the system comprising:
a capacitive proximity sensor coupled to an article of footwear and configured to provide a Lime-varying sensor signal indicating a proximity of a foot to the sensor; and
a processor circuit coupled to the proximity sensor, the processor circuit configured to:
identify a velocity characteristic using the time-varying sensor signal; and
based on the velocity characteristic as identified, at least one of:
initiate data collection about the footwear or about a location of the foot relative to the sensor, using the same proximity sensor or using a different sensor coupled to the footwear, and
update an automated function of the footwear.

10. The system of claim 9, wherein the capacitive proximity sensor comprises a planar electrode and a driven shield provided at or near an insole of the footwear.

11. The system of claim 9, wherein the processor circuit is configured to update a reference characteristic of the capacitive proximity sensor to accommodate a change in a fluid saturation of one or more components of the footwear.

12. The system of claim 10, wherein the processor circuit is configured to determine one or more of a step count, a foot strike force, and a rate of travel using the velocity characteristic as identified.

13. An automated footwear system for use in a footwear article, the system comprising:
a lacing engine and a lacing engine housing configured to be disposed in the article;
a processor circuit provided in the housing; and
a capacitive sensor, including at least one electrode and corresponding driven shield provided at least partially inside of the housing, wherein the capacitive sensor is configured to sense changes in proximity of a body to the at least one electrode and provide a time-varying sensor signal indicative of the proximity of the body to the electrodes;
wherein the processor circuit is configured to:
identify a velocity characteristic using the time-varying sensor signal; and
based on the velocity characteristic as identified, at least one of:
initiate data collection about the footwear or about the proximity of the body to the electrodes, using the same capacitive sensor or using a different sensor coupled to the footwear, and
update an automated function of the lacing engine.

14. The automated footwear system of claim 13, wherein the processor circuit is configured determine one or more of a step count, a foot strike force, or a rate of travel using the velocity characteristic as identified.

15. The automated footwear system of claim 13, wherein the processor circuit is configured to update a reference characteristic of the capacitive sensor based on a detected change in a fluid saturation of one or more components disposed in or coupled to the footwear.

* * * * *

UNITED STATES PATENT AND TRADEMARK OFFICE
CERTIFICATE OF CORRECTION

| | |
|---|---|
| PATENT NO. | : 11,026,481 B2 |
| APPLICATION NO. | : 16/311813 |
| DATED | : June 8, 2021 |
| INVENTOR(S) | : Walker et al. |

It is certified that error appears in the above-identified patent and that said Letters Patent is hereby corrected as shown below:

On the Title Page

On page 5, in Column 2, Item (56) under "Other Publications", Line 29, delete "3020"," and insert --2020",-- therefor In the Claims In Column 54, Line 8, in Claim 9, delete "Lime-varying" and insert --time-varying-- therefor Signed and Sealed this
Sixth Day of September, 2022

Katherine Kelly Vidal
*Director of the United States Patent and Trademark Office*